US010329586B2

(12) United States Patent
Gallei et al.

(10) Patent No.: US 10,329,586 B2
(45) Date of Patent: Jun. 25, 2019

(54) CANINE ADENOVIRUS VECTORS

(71) Applicant: Boehringer Ingelheim Vetmedica GmbH, Ingelheim am Rhein (DE)

(72) Inventors: Andreas Gallei, Wedemark (DE); Ramesh Koukuntla, Ames, IA (US); Robert Barry Mandell, Collins, IA (US); Alice Mundt, Isernhagen (DE); Kristina Rehmet, Hannover (DE); Eric Martin Vaughn, Ames, IA (US)

(73) Assignee: Boehringer Ingelheim Vetmedica GmbH (CZ)

( * ) Notice: Subject to any disclaimer, the term of this patent is extended or adjusted under 35 U.S.C. 154(b) by 0 days.

(21) Appl. No.: 15/706,898

(22) Filed: Sep. 18, 2017

(65) Prior Publication Data

US 2018/0080045 A1 Mar. 22, 2018

Related U.S. Application Data

(60) Provisional application No. 62/397,139, filed on Sep. 20, 2016.

(51) Int. Cl.

| | |
|---|---|
| ***C12N 15/86*** | (2006.01) |
| ***A61K 39/155*** | (2006.01) |
| ***A61K 39/205*** | (2006.01) |
| ***A61K 48/00*** | (2006.01) |
| *A61K 39/00* | (2006.01) |

(52) U.S. Cl.

CPC ............ *C12N 15/86* (2013.01); *A61K 39/155* (2013.01); *A61K 39/205* (2013.01); *A61K 48/00* (2013.01); *A61K 2039/5256* (2013.01); *A61K 2039/545* (2013.01); *A61K 2039/552* (2013.01); *C12N 2710/00* (2013.01); *C12N 2710/10011* (2013.01); *C12N 2710/10041* (2013.01); *C12N 2710/10044* (2013.01); *C12N 2710/10051* (2013.01); *C12N 2710/10343* (2013.01); *C12N 2710/10371* (2013.01); *C12N 2710/16743* (2013.01); *C12N 2760/18634* (2013.01); *C12N 2760/20134* (2013.01); *C12N 2760/20171* (2013.01); *C12N 2830/60* (2013.01)

(58) Field of Classification Search

None

See application file for complete search history.

(56) References Cited

U.S. PATENT DOCUMENTS

| | | | | |
|---|---|---|---|---|
| 3,857,423 | A | 12/1974 | Ronca, Jr. | |
| 5,616,326 | A | 4/1997 | Spibey | |
| 5,820,868 | A | 10/1998 | Mittal et al. | |
| 5,851,521 | A | 12/1998 | Branellec et al. | |
| 6,090,393 | A * | 7/2000 | Fischer ................ C07K 14/005 | 424/204.1 |
| 6,110,735 | A | 8/2000 | Chartier et al. | |
| 6,127,175 | A | 10/2000 | Vigne et al. | |
| 6,156,567 | A | 12/2000 | Fischer | |
| 6,193,983 | B1 | 2/2001 | Crabb et al. | |
| 6,261,807 | B1 | 7/2001 | Crouzet et al. | |
| 6,294,377 | B1 | 9/2001 | Haddada et al. | |
| 6,420,170 | B1 | 7/2002 | Perricaudet et al. | |
| 6,669,942 | B2 | 12/2003 | Perricaudet et al. | |
| 7,037,723 | B1 | 5/2006 | Helibronn | |
| 7,744,900 | B2 | 6/2010 | Dubensky, Jr. et al. | |
| 8,119,396 | B2 | 2/2012 | Eloit et al. | |
| 2001/0014319 | A1 | 8/2001 | Denefle et al. | |
| 2002/0006395 | A1 | 1/2002 | Perricaudet et al. | |
| 2003/0096787 | A1 | 5/2003 | Perricaudet et al. | |
| 2003/0100116 | A1 | 5/2003 | Kremer et al. | |
| 2004/0109873 | A1 | 6/2004 | Neubauer et al. | |
| 2011/0091490 | A1 | 4/2011 | Okazaki et al. | |
| 2011/0110892 | A1 | 5/2011 | Desrosiers | |
| 2011/0236419 | A1 | 9/2011 | Audonnet et al. | |
| 2018/0080043 | A1 | 3/2018 | Mundt et al. | |
| 2018/0080044 | A1 | 3/2018 | Gallei et al. | |
| 2018/0080045 | A1 * | 3/2018 | Gallei ................. A61K 39/155 | |
| 2018/0080047 | A1 | 3/2018 | Mundt et al. | |

FOREIGN PATENT DOCUMENTS

| | | | |
|---|---|---|---|
| EP | 0512017 | B1 | 6/1997 |
| EP | 1118670 | A1 | 7/2001 |
| EP | 0736100 | B1 | 3/2002 |
| EP | 0979101 | B1 | 10/2010 |
| WO | 199111525 | A2 | 8/1991 |
| WO | 199522607 | A1 | 8/1995 |

(Continued)

OTHER PUBLICATIONS

Ho et al. (Biotechnology Letters. 2014; 36: 1569-1579).*
Alignment of SEQ ID 29 with Geneseq database access No. ADP74214 Jun. 2004 by Neubauer et al in USPgPub 2004109873.*
Alignment of SEQ ID 29 with Geneseq database access No. BFD85073 Mar. 2018 by Gallei et al in USPgPub 2018080043.*
Alignment of SEQ ID 30 with Geneseq database access No. ADP74214 Jun. 2004 by Neubauer et al in USPgPub 2004109873.*
Alignment of SEQ ID 31 with Geneseq database access No. BFD85073 Mar. 2018 by Gallei et al in USPgPub 2018080043.*
Greenspan et al (Nature Biotechnology 17:936-937 (1999)).*

(Continued)

*Primary Examiner* — Shanon A. Foley
(74) *Attorney, Agent, or Firm* — Judy Jarecki-Black

(57) ABSTRACT

The present invention relates to the field of CAdV vector vaccines, and especially to promoters suitable to express target antigens from such vector vaccines. Disclosed and claimed are recombinant canine adenoviruses, methods of making them, uses for them (including in immunological, immunogenic, vaccine or therapeutic compositions, or, as a vector for cloning, replicating or expressing DNA and methods of using the compositions and vector), expression products from them, and uses for the expression products. Additionally, disclosed and claimed are truncated EHV4 promoters, expression cassettes containing the promoters, and recombinant viruses and plasmids containing the promoters or expression cassettes.

27 Claims, 19 Drawing Sheets

Specification includes a Sequence Listing.

(56) References Cited

FOREIGN PATENT DOCUMENTS

| | | | |
|---|---|---|---|
| WO | 199800166 | A1 | 1/1998 |
| WO | 200008165 | A1 | 2/2000 |
| WO | 0142481 | A2 | 6/2001 |
| WO | 2007081336 | A1 | 7/2007 |
| WO | 2007115059 | A2 | 10/2007 |
| WO | 2018054822 | A1 | 3/2018 |
| WO | 2018054837 | A1 | 3/2018 |
| WO | 2018054840 | A1 | 3/2018 |
| WO | 2018057441 | A1 | 3/2018 |

OTHER PUBLICATIONS

Alignment of SEQ ID No. 32 with Geneseq database access No. BFD85071 Mar. 2018 by Gallei et al in USPgPub 2018080043.*

Van Olphen et al., "Generation of infectious genome of bovine adenovirus type 3 by homologous recombination in bacteria." Journal of Virological Methods, vol. 77, 1999, pp. 125-129.

Von Einem et al. "In vitro and in vivo characterization of equine herpesvirus type 1 (EHV-1) mutants devoid of the viral chemokine-binding glycoprotein G (gG)." Virology, vol. 362, 2007, pp. 151-162.

Xue et al., "Vaccination with a modified-live bovine viral diarrhea virus (BVDV) type 1a vaccine completely protected calves against challenge with BVDV type 1b strains." Vaccine, vol. 29, 2011, pp. 70-76.

Yang et al., "Complete protection of cats against feline panleukopenia virus challenge by a recombinant canine adenovirus type 2 expressing VP2 from FPV." Vaccine, vol. 26, 2008, pp. 1482-1487.

Zhang et al., "Oral vaccination of dogs (*Canis familiaris*) with baits containing the recombinant rabies-canine adenovirus type-2 vaccine confers long-lasting immunity against rabies." Vaccine, vol. 26, 2008, pp. 345-350.

Babiuk et al, "Adenoviruses as vectors for delivering vaccines to mucosal surfaces." Journal of Biotechnology, vol. 83, 2000, pp. 105-113.

Bangari et al. "Development of nonhuman adenoviruses as vaccine vectors." Vaccine, vol. 24, No. 7, Feb. 2006, pp. 849-862.

Bouet-Cararo et al., "Canine adenoviruses elicit both humoral and cell-mediated immune responses against rabies following immunisation of sheep." Vaccine, vol. 29, 2011, pp. 1304-1310.

Bru et al., "An Update on Canine Adenovirus Type 2 and Its Vectors." Viruses, vol. 2, 2010, pp. 2134-2153.

Brun et al., "Antigen delivery systems for veterinary vaccine development Viral-vector based delivery systems." Vaccine, vol. 26, 2008, pp. 6508-6528.

Chapman et al., "Effect of intron a human cytomegalovirus (Towne) immediate-early gene on heterologous expression in mammalian cells." Nucleic Acids Research, vol. 19, No. 14, 1991, pp. 3979-3986.

Chartier et al., "Efficient Generation of Recombinant Adenovirus Vectors by Homologous Recombination in *Escherichia coli*." Journal of Virology, vol. 70, No. 7, Jul. 1996, pp. 4805-4810.

Chengalvala et al, "Adenovirus vectors for gene expression." Current Opinion in Biotechnology, vol. 2, No. 5, Oct. 1991, pp. 718-722.

Dai et al., "Cellular and humoral immune responses to adenoviral vectors containing factor IX gene: Tolerization of factor IX and vector antigens allows for long-term expression." Proceedings of the National Academy of Sciences, vol. 92, Feb. 1995, pp. 1401-1405.

De Turiso et al., "Recombinant Vaccine for Canine Parvovirus in Dogs." Journal of Virology, vol. 66, No. 5, May 1992, pp. 2748-2753.

Dong et al., "Systematic Analysis of Repeated Gene Delivery into Animal Lungs with a Recombinant Adenovirus Vector" Human Gene Therapy, vol. 7, No. 3, Feb. 10, 1996, pp. 319-331.

Fallaux et al., "New Helper Cells and Matched Early Region 1-Deleted Adenovirus Vectors Prevent Generation of Replication-Competent Adenoviruses." Human Gene Therapy, vol. 9, Sep. 1, 1998, pp. 1909-1917.

Fischer et al., "Vaccination of puppies born to immune dams with a canine adenovirus-based vaccine protects against a canine distemper virus challenge." Vaccine, vol. 20, 2002, pp. 3485-3497.

Ghosh-Choudhury et al., "Human adenovirus cloning vectors based on infectious bacterial plasmids." Gene, vol. 50, Nos. 1-3, 1986, pp. 161-171.

Haj-Ahmad et al., "Development of a helper-independent human adenovirus vector and its use in the transfer of the herpes simplex virus thymidine kinase gene." Journal of Virology, vol. 57, No. 1, Jan. 1986, pp. 267-274.

Henderson et al., "Oral immunization of raccoons and skunks with a canine adenovirus recombinant rabies vaccine." Vaccine, vol. 27, 2009, pp. 7194-7197.

Hsu et al., "Efficacy of adenovirus-vectored respiratory syncytial virus vaccines in a new ferret model." Vaccine, vol. 12, No. 7, 1994, pp. 607-612.

Hu et al., "Experimental immunization of cats with a recombinant rabies-canine adenovirus vaccine elicits a long-lasting neutralizing antibody response against rabies." Vaccine, vol. 25, 2007, pp. 5301-5307.

Hu et al., "Prevention of rabies virus infection in dogs by a recombinant canine adenovirus type-2 encoding the rabies virus glycoprotein." Microbes and Infection, vol. 8, 2006, pp. 1090-1097.

Huang et al., "Glycoprotein G deletion mutants of equine herpesvirus 1 (EHV1; equine abortion virus) and EHV4 (equine rhinopneumonitis virus)." Archives of Virology, vol. 150, 2005, pp. 2583-2592.

Imler, Jean-Luc, "Adenovirus vectors as recombinant viral vaccines." Vaccine, vol. 13, No. 13, 1995, pp. 1143-1151.

International Search Report and Written Opinion for PCT/US2017/051964 dated Nov. 20, 2017.

Kapoor et al., "A nonessential glycoprotein is coded by early region E3 of adenovirus type 7." Virology, vol. 112, No. 2, Jul. 30, 1981, pp. 780-784.

Kelly et al., "Use of Nondefective Adenovirus-Simian Virus 40 Hybrids for Mapping the Simian Virus 40 Genome." Journal of Virology, vol. 12, No. 3, Sep. 1973, pp. 643-652.

Kremer et al., "Canine Adenovirus Vectors: an Alternative for Adenovirus-Mediated Gene Transfer." Journal of Virology, vol. 74, No. 1, 2000, pp. 505-512.

Levrero et al., "Defective and nondefective adenovirus vectors for expressing foreign genes in vitro and in vivo." Gene, vol. 101, No. 2, May 30, 1991, pp. 195-202.

Li et al., "A single immunization with a recombinant canine adenovirus expressing the rabies virus G protein confers protective immunity against rabies in mice." Virology, vol. 356, 2006, pp. 147-154.

Linné, Tommy, "Differences in the E3 regions of the canine adenovirus type 1 and type 2." Virus Research, vol. 23, Nos. 1-2, Apr. 1992, pp. 119-113.

Liu et al., "Efficacy and safety of a live canine adenovirus-vectored rabies virus vaccine in swine." Vaccine, vol. 26, 2008, pp. 5368-5372.

Lubeck et al., "Immunogenicity and efficacy testing in chimpanzees of an oral hepatitis B vaccine based on live recombinant adenovirus." Proceedings of the National Academy of Sciences USA, vol. 86, No. 17, Sep. 1989, pp. 6763-6767.

Ma et al., "An Equine Herpesvirus Type 1 (EHV-1) Expressing VP2 and VP5 of Serotype 8 Bluetongue Virus (BTV-8) Induces Protection in a Murine Infection Model." PLoS ONE, vol. 7, No. 4, Apr. 2012, e34425, pp. 1-9.

Massie et al., "New adenovirus vectors for protein production and gene transfer." Cytotechnology, vol. 28, 1998, pp. 53-64.

Mittal et al., "Pathology and immunogenicity in the cotton rat (*Sigmodon hispidus*) model after infection with a bovine adenovirus type 3 recombinant virus expressing the firefly luciferase gene." Journal of General Virology, vol. 77, 1996, pp. 1-9.

(56) References Cited

OTHER PUBLICATIONS

Morin et al., "Recombinant adenovirus induces antibody response to hepatitis B virus surface antigen in hamsters." Proceedings of the National Academy of Sciences, USA, vol. 84, Jul. 1987, pp. 4626-4630.
Morrison et al., "Generation of E3-Deleted Canine Adenoviruses Expressing Canine Parvovirus Capsid by Homologous Recombination in Bacteria." Virology, vol. 293, 2002, pp. 26-30.
Nagesha et al., "Analysis of the nucleotide sequence of five genese at the left end of the unique short region of the equine herpesvirus 4 genome." Archives of Virology, vol. 128, 1993, pp. 143-154.
Natuk et al., "Immunogenicity of Recombinant Human Adenovirus-Human Immunodeficiency Virus Vaccines in Chimpanzees." AIDS Research and Human Retroviruses, vol. 9, No. 5, May 1993, pp. 395-404.
Prevec et al., "Use of Human Adenovirus-based Vectors for Antigen Expression in Animals." Journal of General Virology, vol. 70, 1989, pp. 429-434.
Reddy et al., "Development of porcine adenovirus-3 as an expression vector." Journal of General Virology, vol. 80, 1999, pp. 563-570.
Said et al., "An equine herpesvirus 1 (EHV-1) vectored H1 vaccine protects against challenge with swine-origin influenza virus H1N1." Veterinary Microbiology, vol. 154, 2011, pp. 113-123.
Said et al., "Recombinant equine herpesvirus 1 (EHV-1) vaccine protects pigs against challenge with influenza A (H1N1)pmd09". Virus Research, vol. 173, 2013, pp. 371-376.
Said, Abdelrahman, "Development of a vectored equine herpesvirus type 1 (EHV-1) vaccine against pandemic influenza A virus (09/H1N1)." Inaugural-Dissertation, Berlin, 2013, Journal-Nr: 3637, pp. 1-83. [Accessed at: http://www.diss.fu-berlin.de/diss/servlets/MCRFileNodeServlet/FUDISS_derivate_000000013293/Said_online.pdf retrieved on Mar. 8, 2017].
Saito et al., "Construction of nondefective adenovirus type 5 bearing a 2.8-kilobase hepatitis B virus DNA near the right end of its genome." Journal of Virology, vol. 54, No. 3, Jun. 1985, pp. 711-719.
Shibata et al., "Nucleotide Sequence of E1 Region of Canine Adenovirus Type 2." Virology, vol. 172, 1989, pp. 460-467.
Spibey et al., "Identification and nucleotide sequence of the early region 1 from canine adenovirus types 1 and 2." Virus Research, vol. 14, No. 3, Nov. 1989, pp. 241-255.
Spibey et al., "Molecular Cloning and Restriction Endonuclease Mapping of Two Strains of Canine Adenovirus Type 2" Journal of General Virology, vol. 70, 1989, pp. 165-172.
Tartaglia et al., "Protection of Cats against Feline Leukemia Virus by Vaccination with a Canarypox Virus Recombinant, ALVAC-FL." Journal of Virology, vol. 67, N. 4, Apr. 1993, pp. 2370-2375.
Telford et al., "The DNA sequence of equine herpesvirus-4." Journal of General Virology, vol. 79, 1998, pp. 1197-1203.
Trapp et al. "Potential of Equine Herpesvirus 1 as a Vector for Immunization." Journal of Virology, vol. 79, No. 9, May 2005, pp. 5445-5454.
Van De Walle et al., "Analysis of the Herpesvirus Chemokine-binding Glycoprotein G Residues Essential for Chemokine Binding and Biological Activity." The Journal of Biological Chemistry, vol. 384, No. 9, Feb. 27, 2009, pp. 5968-5976.

* cited by examiner

E

| Reaction (lane) | Primer Set | Expected Product Size (bp) |
|---|---|---|
| 1 | H-A P VIII, VP2 | 841 |
| 2 | VP2, U-exon | 801 |
| 3 | VP2, VP2 | 709 |
| 4 | VP2, VP2 | 1200 |
| 5 | VP2, VP2 | 595 |
| 6 | H-A P VIII, U-exon | 1697 for pCAV-2 (>3Kb for pCAV2-VP2) |

anti-CPV VP2 anti-CAV2

Uninfected MDCK rCAV2-BRSV F (co) MDCK rCAV2-CPV VP2 (co) MDCK

G

| Panel | Sample | Antibody | % of positive cells | FITC-A mean |
|---|---|---|---|---|
| A | Uninfected MDCK | anti-CPV VP2 | 15.1 | 1271 |
| B | MDCK/CAV2-BRSV F (co) | anti-CPV VP2 | 12.6 | 1209 |
| C | MDCK/CAV2-CPV VP2 (co) | anti-CPV VP2 | 50.4 | 1440 |
| D | Uninfected MDCK | anti-CAV2 | 9.7 | 1260 |
| E | MDCK/CAV2-BRSV F (co) | anti-CAV2 | 98.2 | 1206 |
| F | MDCK/CAV2-CPV VP2 (co) | anti-CAV2 | 99.4 | 20498 |

FIG. 15:

| Recombinant virus | Mean CAV-2 Protein | CAV-2 Infected Cells (%) | Mean VP2 Protein | VP2 Expressing Cells (%) |
|---|---|---|---|---|
| CAV2 CMVie BRSV F | 518113 | 48.47 | n/a | 0.23 |
| CAV2 CMVie CPV VP2 (Despl) | 656218 | 62.21 | 178929 | 2.61 |
| CAV2 CMVie CPV VP2 (Gen0.95) | 697527 | 63.99 | 164591 | 2.59 |

FIG. 16:

| Recombinant virus | Mean CAV-2 Protein | CAV-2 Infected Cells (%) | Mean VP2 Protein | VP2 Expr. Cells (%) | Mean VP2 Protein | VP2 Expr. Cells (%) |
|---|---|---|---|---|---|---|
| CAV2 CMVie BRSV F | 249037 | 16.13 | 47389 | 0.80 | n/a | 0.45 |
| CAV2 gG430 CPV VP2 (Despl) | 265134 | 18.28 | 151824 | 18.20 | 260564 | 14.17 |
| CAV2 gG430 CPV VP2 (Gen0.95) | 292271 | 32.82 | 136458 | 28.31 | 221600 | 19.68 |
| CAV2 MCP455 CPV VP2 (Gen0.95) | 248349 | 24.65 | 188663 | 35.78 | 292102 | 29.73 |
| | Anti-CAV2-FITC pAb | | Anti-CPV VP2-FITC | | Anti-CPV VP2 pAb | |

A:

B:

| | | Supernatants/lysates from recombinant virus-infected cells | | | |
|---|---|---|---|---|---|
| Rec. Virus | | CAV-2 CMVie BRSV F | CAV-2 gG430 CPV VP2 (Despl) | CAV-2 gG430 CPV VP2 (Gen0.95) | CAV-2 MCP CPV VP2 (Gen0.95) |
| Dilution | 1 | - | ++++ | ++ | ++++ |
| | 0.5 | - | +++ | + | ++++ |
| | 0.25 | - | +++ | + | ++++ |
| | 0.125 | - | +++ | + | ++++ |
| | 0.0625 | - | ++ | +/- | +++ |
| | 0.0312 | - | + | - | ++ |
| | 0.0156 | - | +/- | - | + |

FIG. 18:

| Recombinant virus | Mean CAV-2 Protein | CAV-2 Infected Cells (%) | Mean RabG Protein | rabG Expressing Cells (%) |
|---|---|---|---|---|
| CAV2 gG430 CPV VP2 (Gen0.95) | 516801 | 46.22 | n/a | 0.63 |
| Original CAV2 CMVie RabG (n) | 375281 | 16.79 | 33298 | 1.58 |
| CAV2 MCP455 RabG (n) | 542598 | 54.41 | 90294 | 14.22 |
| | Anti-CAV2-FITC pAb | | Anti-RabG-FITC | |

FIG. 19A: IFA for CPV VP2 expression in infected AI-ST 2015 cells
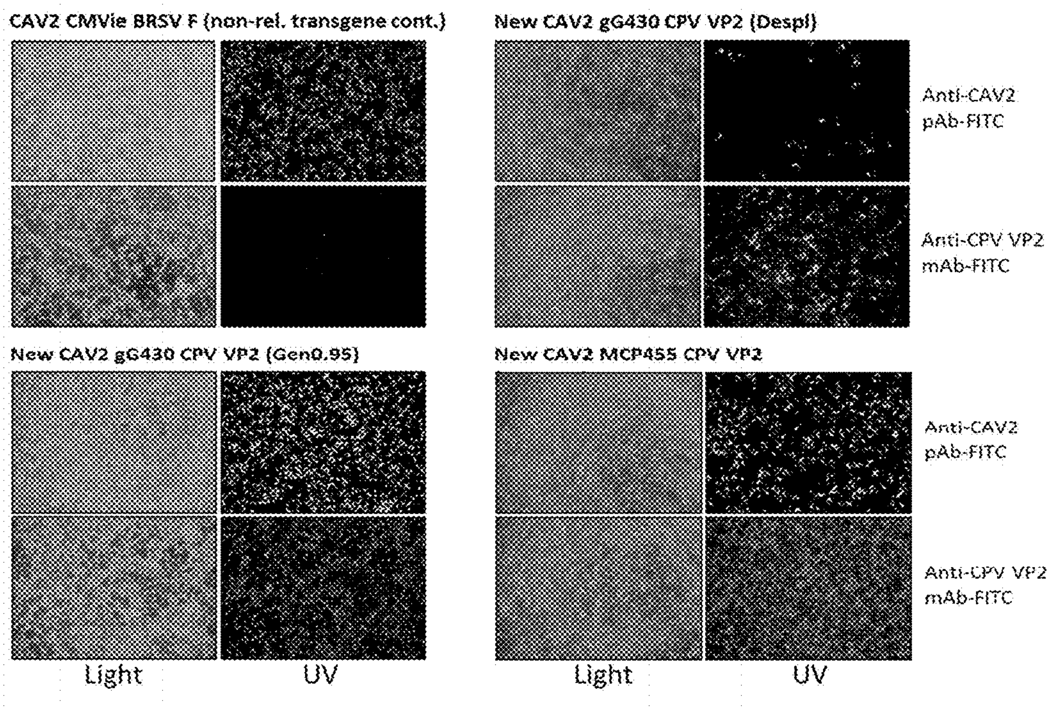
FIG. 19B: IFA for RabG expression in AI-ST 2015 cells.
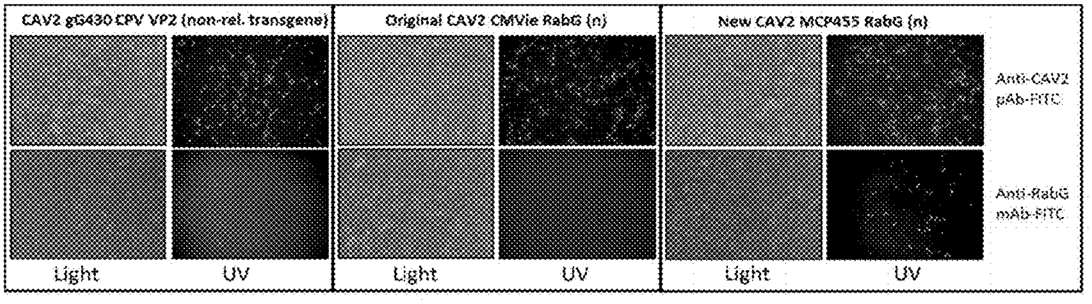
FIG. 19C: IFA for RabG expression in BIVI 2011 MDCK cells – dual stain for RabG and CAV-2
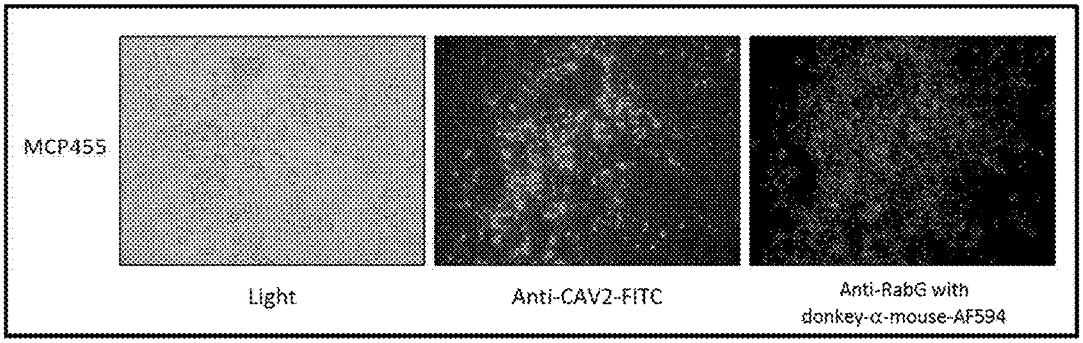

CANINE ADENOVIRUS VECTORS

CROSS-REFERENCE TO OTHER APPLICATIONS

This application claims the benefit of U.S. Patent Application No. 62/397,139, filed Sep. 20, 2016, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

A. Field of the Invention

The present invention relates to the field of (vector) vaccines, and especially to recombinant canine adenovirus type 2, particularly with improved expression cassettes suitable to express target antigens from such vector vaccines.

B. Background and Description of the Related Art

Adenoviruses have been extensively investigated as vectors for recombinant vaccines (see review Bru, T., S. Salinas, and E. J. Kremer, An update on canine adenovirus type 2 and its vectors. Viruses, 2010. 2(9): p. 2134-53). There is wealth of information accumulated on adenoviruses over the last couple of decades, specifically in the fields of gene therapy and vaccine development. Several features of adenoviruses make them attractive as gene transfer tools: (1) the structure of the adenoviral genome is well characterized; (2) large portions of viral DNA can be substituted by foreign sequences; (3) the recombinant variants are relatively stable, (4) the recombinant virus can be grown at high titer; (5) no human malignancy is associated with adenovirus; and (6) the use of attenuated wild-type adenovirus as a vaccine is safe.

Published targets for efficacious vectored CAV-2 vaccines include rabies for cats (Hu, R. L., et al., Experimental immunization of cats with a recombinant rabies-canine adenovirus vaccine elicits a long-lasting neutralizing antibody response against rabies. Vaccine, 2007. 25(29): p. 5301-7), dogs (Hu, R., et al., Prevention of rabies virus infection in dogs by a recombinant canine adenovirus type-2 encoding the rabies virus glycoprotein. Microbes Infect, 2006. 8(4): p. 1090-7), mice (Li, J., et al., A single immunization with a recombinant canine adenovirus expressing the rabies virus G protein confers protective immunity against rabies in mice. Virology, 2006. 356(1-2): p. 147-54), raccoons (Henderson, H., et al., Oral immunization of raccoons and skunks with a canine adenovirus recombinant rabies vaccine. Vaccine, 2009. 27(51): p. 7194-7), sheep (Bouet-Cararo, C., et al., Canine adenoviruses elicit both humoral and cell-mediated immune responses against rabies following immunization of sheep. Vaccine, 2011. 29(6): p. 1304-10), skunks (Henderson, H., et al., Oral immunization of raccoons and skunks with a canine adenovirus recombinant rabies vaccine. Vaccine, 2009. 27(51): p. 7194-7) and swine (Liu, Y., et al., Efficacy and safety of a live canine adenovirus-vectored rabies virus vaccine in swine. Vaccine, 2008. 26(42): p. 5368-72), canine distemper (Fischer, L., et al., Vaccination of puppies born to immune dams with a canine adenovirus-based vaccine protects against a canine distemper virus challenge. Vaccine, 2002. 20(29-30): p. 3485-97), and feline panleukopenia (Yang, S., et al., Complete protection of cats against feline panleukopenia virus challenge by a recombinant canine adenovirus type 2 expressing VP2 from FPV. Vaccine, 2008. 26(11): p. 1482-7). CAV-2 also presents the potential to be used as an oral vaccine, as indicated by efficacy by oral vaccination of dogs (Zhang, S., et al., Oral vaccination of dogs (*Canis familiaris*) with baits containing the recombinant rabies-canine adenovirus type-2 vaccine confers long-lasting immunity against rabies. Vaccine, 2008. 26(3): p. 345-50), raccoons and skunks for rabies (Henderson, H., et al., 2009, Zhao et al. 2014. Experimental Oral Immunization of Ferret Badgers (*Melogale moschata*) with a Recombinant Canine Adenovirus Vaccine CAV-2-E3A-RGP and an Attenuated Rabies Virus SRV9. J. Wildlife Diseases 50(2):374-377.). Interestingly, replication competent adenovirus-based vectors have shown efficacy in spite of passive immunity against the vector (Gallichan, W. S., et al., Mucosal immunization with a recombinant adenovirus vector induces local and systemic immunity and protection from herpes simplex virus. Adv Exp Med Biol, 1995. 371B: p. 1581-5; Lubeck, M. D., et al., Immunogenicity of recombinant adenovirus-human immunodeficiency virus vaccines in chimpanzees following intranasal administration. AIDS Res Hum Retroviruses, 1994. 10(11): p. 1443-9; Wang, Y., et al., The use of an E1-deleted, replication-defective adenovirus recombinant expressing the rabies virus glycoprotein for early vaccination of mice against rabies virus. J Virol, 1997. 71(5): p. 3677-8)., suggesting they might overcome maternal-derived immunity (Papp, Z., L. A. Babiuk, and M. E. Baca-Estrada, The effect of pre-existing adenovirus-specific immunity on immune responses induced by recombinant adenovirus expressing glycoprotein D of bovine herpesvirus type 1. Vaccine, 1999. 17(7-8): p. 933-43; Babiuk, L. A. and S. K. Tikoo, Adenoviruses as vectors for delivering vaccines to mucosal surfaces. J Biotechnol, 2000. 83(1-2): p. 105-13). This was confirmed for canine distemper by Fischer et al. (2002). However, preexisting antibodies might preclude the use of the oral route of immunization (Wright, N., et al., High prevalence of antibodies against canine adenovirus (CAV) type 2 in domestic dog populations in South Africa precludes the use of CAV-based recombinant rabies vaccines. Vaccine, 2013. 31(38): p. 4177-82).

Canine adenovirus type 2 (CAV-2) usually causes an unapparent to mild infection of the respiratory tract and is regarded as one of the causes of the common widespread infectious tracheobronchitis (Buonavoglia, C. and V. Martella, Canine respiratory viruses. Vet Res, 2007. 38(2): p. 355-73; Tham, K. M., G. W. Horner, and R. Hunter, Isolation and identification of canine adenovirus type-2 from the upper respiratory tract of a dog. N Z Vet J, 1998. 46(3): p. 102-5). CAV-2 has also been implicated in episodes of enteritis (Hamelin, C., P. Jouvenne, and R. Assaf, Association of a type-2 canine adenovirus with an outbreak of diarrheal disease among a large dog congregation. J Diarrhoeal Dis Res, 1985. 3(2): p. 84-7; Macartney, L., H. M. Cavanagh, and N. Spibey, Isolation of canine adenovirus-2 from the feces of dogs with enteric disease and its unambiguous typing by restriction endonuclease mapping. Res Vet Sci, 1988. 44(1): p. 9-14) and has been detected in the brain of dogs with neurological signs (Benetka, V., et al., Canine adenovirus type 2 infection in four puppies with neurological signs. Vet Rec, 2006. 158(3): p. 91-4.). Several CAV2-based vaccines have been developed and extensively used worldwide for the vaccination of puppies and adult dogs. Modified live CAV-2 vaccines proved to be highly effective in reducing the circulation of CAV-2 in canine populations (Buonavoglia et al., 2007). Dogs vaccinated with CAV-2 develop immunity to both CAV-1 and CAV-2 (Appel, M., et al., Pathogenicity of low-virulence strains of two canine adenovirus types. Am J Vet Res, 1973. 34(4): p. 543-50; Appel, M., L. E. Carmichael, and D. S. Robson, Canine adenovirus type 2-induced immunity to two canine adenoviruses in pups with maternal antibody. Am J Vet Res, 1975. 36(08): p. 1199-202). The use of CAV-2 for immunization of pups against both canine adenovirus types has eliminated safety-related side-effects encountered with CAV-1 vaccines (Bittle, J. L., W. A. Grant, and F. W. Scott, Canine and feline immunization guidelines—1982. J Am Vet Med Assoc, 1982. 181(4): p. 332-5; Curtis, R. and K. C. Barnett, The 'blue eye' phenomenon. Vet Rec, 1983. 112 (15): p. 347-53). The apparent safety of CAV2 as a vaccine has been well evidenced by the lack of vaccine-induced and vaccine-associated complications in dogs and other animal species including man during its 30 years of utility. Further, results from field serological surveys indicate that many wild animals (foxes, raccoons, skunks and mongooses) are asymptomatically exposed to CAV2 or to an antigenically related virus infection (Summer et al., 1988). A vaccinal strain of canine adenovirus serotype 2 (CAV2), therefore, provides a unique example of a safe replication-competent, host-restricted virus which can be considered for the derivation of effective vector-based vaccine candidate for vaccination, especially of dogs.

The canine adenovirus therefore has many ideal characteristics for the development of vectored virus vaccines. In addition to its safe and efficacious use, as detailed above, it provides important features including: humoral and cellular immune responses to vaccine, which viral pathogen targets might require for protection; it has a broad potential host range and tissue tropism; it is non-enveloped, so likely more stable than enveloped viruses; it can grow to high titers and there are well established production protocols and assays in place; it can be used as both a replication competent and deficient virus; and it can carry relatively large amounts of heterologous DNAs, particularly when the CAdV is "gutless" ~30 kb of exogenous DNA can be inserted, however the virus must then rescued in the presence of helper virus.

Fisher et al., in U.S. Pat. No. 6,090,393 (herein incorporated by reference), described the use of a recombinant CAdV2, having exogenous DNA inserted into non-essential regions or portions within the E1, E3, and/or the right end of the genome between the right ITR and the E4 transcription unit. The E3 region was employed for generation of the recombinant because part of this region was identified as non-essential both in vitro and in vivo for infectious virus formation (e.g., based on data derived from HAVs and bovine Ad3) and therefore was targeted as an insertion region. Adenovirus vectors which have a deleted E1 region are replication-incompetent and have other challenges and thus were not preferred for use.

Fisher et al. further disclosed the use of truncated promoters derived from murine cytomegalovirus or human cytomegalovirus MCMV or HCMV, e.g., HCMV-IE or MCMV-IE. The hCMV-IE promoter was elected by Fisher et al. as the state of the art and as a promising upstream regulatory region, concluding that it was associated with the highest level and the longest persistence of recombinant protein expression in tissue culture. The hCMV-IE promoter was also regarded as a clear advantage because it was found to operate in almost every cell line tested. The impetus behind the targeted deletions of portions of the promoter, such as the HCMV-IE, was to reduce the size of the promoter and thus address the packing limitations of adenoviruses. Fisher et al. specifically disclosed an active fragment of the HCMV-IE having a size of 91 bp or an active fragment of the MCMV-IE having a size of 466 bp, i.e., a truncated transcriptionally active HCMV-IE of about 91 bp or a truncated transcriptionally active MCMV-IE of about 466 bp.

While Fisher et al. describes the construction of various recombinant CAdV2 vectors, e.g., expression cassette encoding a polynucleotide for a CDV haemagluttanin (HA) or fusion (F) protein operably linked to the vaccinia virus H6 (vH6) promoter, Fisher et al. did not demonstrate robust CDV antigen expression from any of the CAdV2 vectors constructed. Instead, the Fisher '393 Patent disclosed the general nucleotide size limitations at the E3 insertion sites as variables for stable expression, never observing and/or addressing any possibility variability in the choice of promoters as contributing to viral rescue or expression of heterologous proteins in infected cells. In a follow-on study of Fisher et al. 2002 ("Vaccination of puppies born to immune dams with a canine adenovirus-based vaccine protects against a canine distemper virus challenge" Vaccine 20 (2002) 3485-3497), they reported the first construction and characterization of two recombinant CAdV2 viruses in which the CDV HA and F expression cassettes had been inserted into the E3 region of the vector driven by a 91 bp fragment of the hCMV IE promoter. They further replaced the hCMVIE 5'UTR with the hAd2 TPL to facilitate the expression of the transgene gene after the onset of CAV2 replication. Collectively, the emphasis in the cloning strategy was to minimize the size of the expression cassettes for both CDV HA and F cDNAs. Furthermore, the study detailed potential viral recovery issues due to the specific insertion site, the deletion size, the insertion size, and the insertion orientation. In that study they were able to recover stable clones demonstrating correct insertion and were able to assay for the induction of immunity following immunization. Following a single intranasal administration of the mixture of rCAdV2 encoding the entire CDV HA and vCA17 to seronegative puppies, very high systemic CDV SN titers (>2.0 log 10) and almost complete protection after challenge were observed. However, since the puppies were immunized with a mixture of the two vectors containing the HA and F antigens, the authors could not conclude as to whether one or both vectors expressed the CDV transgenes in immunized dogs, nor did they conclusively demonstrate robust expression of the transgene in individual cell populations.

Experiments described herein demonstrate that robust transgene expression from cassettes inserted at the E3 genomic locus was not observed in cells infected with replication-competent rCAdV-2 CMV5-driven transgene expression cassettes as measured by detection of proteins (IFA, flow cytometry, dot blot). In fact, experiments herein show that rCAdV-2 vectors with expression cassettes with the CMV5 promoter could not be rescued, so protein expression could not be measured in infected cells. This was despite the fact that in vitro transient transfections with the same transfer plasmids containing those expression cassettes demonstrated CMV5 promoter activity was great than CMVie promoter activity in regard to protein expression levels Thus absence of robust, reproducible, transgene expression, and/or viral rescue made the usefulness of the CMV-driven expression cassettes in the CAdV2 vector, particularly in hosts where replication does not occur, very questionable.

Therefore, while the extremely strong and non-tissue specific HCMV and MCMV (Mouse cytomegalovirus) IE promoters-enhancers may be well suited for a variety of research activities and for limited usefulness in the target species where the CAdV2 replicates, they were not considered effective and or reliable promoters for the construction of CAdV2 vector vaccines for use in other species. What was necessary was replacement of the CMV promoters with effective promoters that are capable of driving stable, robust, reproducible expression of antigenic epitopes of interest in the context of the recombinant CAdV2 virus for the production of vaccines for use in a variety of species.

SUMMARY OF THE INVENTION

In order to avoid any such obstacles the present invention provides new regulatory nucleic acid sequences/promoter sequences for transgene expression, especially within the context of vector vaccines and especially within the context of the CAdV-2 vector.

Thus, the solution to the above described technical problem is achieved by the description and the embodiments characterized in the claims and the invention in its different aspects is implemented according to the claims.

The present invention provides new regulatory nucleic acid sequences/promoter sequences for transgene expression, immunogenic compositions, vaccines, and related methods that overcome deficiencies in the art.

Established promoter sequences widely used to drive high levels of transgene expression in various vector systems including herpesviruses are the promoter sequences of immediate-early genes of HCMV (Boshart et al., 1985; Foecking and Hofstetter 1986) or the mouse cytomegalovirus (MCMV; Dorsch-Hasler et al., 1985) or strong promoters of oncogenic viruses like simian virus 40 (SV40), e.g. the SV40 large T-antigen promoter and many more (e.g., Kim et al., 1990). Such strong promoters were preferred by cell biologists because they function autonomously in various cell culture systems. In the context of viral replication an infected cell is transformed by viral functions into a virus-replicating machine.

For improved vector vaccines, however, none of the autonomous strong promoters described above is seen as an option; in particular CMV derived promoters were not effective, reproducible drivers of transgene expression in recombinant CAdV2 vector vaccines.

Thus, there is a need to provide promoters with high activity in the context of viral replication like those of EHV-1 β- and γ-genes. The present invention provides new alternative promoter sequences derived from the published genomic sequence of EHV-4 (Equine herpesvirus 4 strain NS80567, complete genome, Accession AF030027, Version AF030027.1 GI:2605950, date 21 May 1998). Sequence identity of the genes with EHV-1 genes is in the range of 55 to 84%.

The present invention provides two new promoters: 4pgG600 and 4pMCP600, and derivatives of shorter lengths thereof, which are shown to be functional after transient transfection in cell cultures or in the background of rCAdV-BAC replication in cell cultures.

The present invention provides two new promoters: p430 and p455, which are shown to be functional in the background of rCAdV2 replication in cell cultures, and, for p455, also in animals (pigs). Activity levels of the two new promoters during the viral replication cycle appear to be very similar as deduced from in vitro promoter kinetic experiments.

The new promoter sequences provided by the present invention are shown to be efficient in the canine adenovirus (CAdV) vector background.

As discussed above, the rescue of recombinant CAdV was not achieved when the CMV5 promoter sequence was present in the expression cassettes located in the E3 region. This appears to be sequence-specific as the size of the expression cassettes had not exceeded observed experimental genome size limitations. In contrast, the new EHV-4 derived promoter sequences of the present invention such as p430 and p455 not only facilitate transgene expression, but also do not interfere with the crucial step of viral rescue and are, therefore, advantageous in view of prior art promoter sequences.

DETAILED DESCRIPTION OF THE INVENTION

The present invention solves the problems inherent in the prior art and provides a distinct advance in the state of the art.

Generally, the present invention provides recombinant canine adenovirus (rCAdV) vector comprising an expression cassette encoding at least one heterologous DNA operably linked to an equine herpesvirus-4 (EHV4) promoter.

The present invention further concerns a rCAdV vector, wherein the equine herpesvirus-4 (EHV4) promoter comprises 4pgG600 (SEQ ID NO.:29) or 4pMCP600 (SEQ ID NO.:30) or the complementary nucleotide sequences thereof or a functional fragment or a functional derivative thereof or the complementary nucleotide sequences thereof, wherein said promoter sequence leads to expression of a heterologous antigen.

In a specific aspect the functional fragment or derivative of the promoter sequence has at least 80%, 85% sequence identity, preferably 90%, 91%, 92%, 93%, 94% sequence identity, more preferably 95%, 96%, 97%, 98%, 99%, 99.9% sequence identity.

In a specific aspect the functional fragment is a truncation of 4pgG600 (SEQ ID NO.:29) or the complementary nucleotide sequence thereof, preferably the sequence identity is at least 72% over entire length.

In a specific aspect the functional fragment is a truncation of 4pMCP600 (SEQ ID NO.: 30) or the complementary nucleotide sequence thereof, preferably the sequence identity is at least 78% over entire length (or higher).

In a further specific aspect the functional fragment or derivative of the promoters 4pgG600 (SEQ ID NO.:29) or 4pMCP600 (SEQ ID NO.:30) sequence have a length of 550 nucleotides, preferably 500, 490, 480, 470, 460, 455, 450, 445, 440, 435, 434, 433, 432, 431, 430 nucleotides, most preferably 455 or 430 nucleotides.

In a further specific aspect the rCAdV vector comprises the equine herpesvirus-4 (EHV4) promoter comprising 4pgG600 (SEQ ID NO.:29).

In a further specific aspect the rCAdV vector comprises the equine herpesvirus-4 (EHV4) promoter comprises 4pMCP600 (SEQ ID NO.: 30).

In a further specific aspect the rCAdV vector comprises the equine herpesvirus-4 (EHV4) promoter comprises 4pG430 (SEQ ID NO.:31).

In a further specific aspect the rCAdV vector comprises the equine herpesvirus-4 (EHV4) promoter comprises gMCP455 (SEQ ID NO.:32).

In a specific aspect of the invention the rCAdV vector is packaged as an infectious CAdV.

In yet another embodiment of the invention the rCAdV vector comprises a heterologous DNA encoding a polypeptide selected from the group consisting of an epitope of interest, a biological response modulator, a growth factor, a recognition sequence, a therapeutic gene, and a fusion protein.

In a specific aspect of the invention the heterologous DNA encodes an antigenic epitope of interest.

In yet another embodiment of the invention the antigenic epitope of interest is an antigen of a canine or feline pathogen.

In a specific aspect of the invention, the antigenic epitope of interest is an antigen derived from a food producing animal pathogen, more specifically wherein the food producing animal pathogen is derived from swine, cattle, equine, poultry, and/or ovine animals; and more specifically, wherein the food producing animal pathogen is selected from the group consisting of: Bovine viral diarrhea virus (BVDV), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronovirus (BCV), Bovine Rabies (BR), Bovine Parvovirus (BPV), Adenovirus Astrovirus, *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C fetus intestinalis*), *Leptospira interrogans, Leptospira hardjo, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium* paratuberculosis, *Cryptsporidium parvum, Cryptsporidium hominis, Staphylococcus aureus, Streptococcus dysgalactiae, Streptococcus uberis, Streptococcus agalactiae, Escherichia coli, Mycoplasma* spp, *Mycoplasma dispar*, and *Ureaplasma* spp., *Tritrichomonas foetus, Trichophyton verrucosum, Trichophyton mentagrophytes, Trichophyton sarkisovii, Neospora caninum* (formerly *Toxoplasma gondii*), *Babesia bigemina* and *Babesia bovis, Dictyocaulus viviparous* (Lungworm disease), and combinations thereof.

In a specific aspect of the invention, the antigenic epitope of interest is an antigen derived from a food producing animal pathogen, more specifically wherein the food producing animal pathogen is derived from swine, cattle, equine, poultry, and/or ovine animals; and more specifically, wherein the food producing animal pathogen is selected from the group consisting of: *Salmonella* spp., in particular *S. typhimurium S. choleraesuis*; Astroviruses; Rotavirus; Transmissible gastroenteritis virus; *Brachyspira* spp., in particular *B. hyodysenteriae, B. pilosicoli; Clostridium* spp., in particular *C. difficile, C. perfringens* types A, B and C, *C. novyi, C. septicum, C. tetani*; Porcine enteric picornaviruses; Porcine enteric caliciviruses; respiratory pathogens, which include: *Actinobacillus pleuropneumonia; Bordetella bronchiseptica; Erysipelothrix rhsiopathiae; Haemophilus parasuis*, in particular subtypes 1, 7 and 14; *Pasteurella* spp., in particular *P. multocida; Mycoplasma* spp., in particular *M. hyopneumoniae, M. hyorhinis*; Swine influenza A virus; PRRS virus; Porcine circovirus; Porcine parvovirus; Pseudorabies virus; *Eperythrozoonosis suis, Mycobacterium* spp., in particular *M. avium, M. intracellulare, M. bovis*; Porcine respiratory corona virus; Porcine coronavirus in particular TGEV, PEDV, and delta coronavirus; *Arcanobacterium pyogenes*; Porcine adenovirus; Classical swine fever; Porcine cytomegalovirus; African swine fever; or other pathogens, which include *Escherichia coli, Streptococcus* spp., in particular *S. suis, S. porcinus, S. dysgalactiae*, preferably subsp. *equisimilis; Brucella suis*, in particular biovars 1, 2 and 3; *Leptospira* spp., in particular *L. australis, L. canicola, L. grippotyphosa, L. pomona, L. icterohaemorrhagicae, L. interrogans, L. tarassovi, L. hardjo, L. sejroe*; Encephalomyocarditis virus; Hemagglutinating encephalomyelitis virus; Japanese encephalitis virus; West Nile virus; Reovirus; Rubulavirus; Menangle virus; Nipah virus; Vesicular stomatitis virus; Virus of vesicular exanthema of swine; Swine pox virus; Swine herpes virus; and *Staphylococcus hyicus*, and combinations thereof.

In a further embodiment of the invention, the antigenic epitope of interest is selected from the group consisting of a Morbillivirus antigen, a rabies glycoprotein, Feline Leukemia virus (FeLV) envelope protein, an immunodeficiency virus antigen, a parvovirus antigen, a poxvirus antigen.

The present invention further concerns an immunogenic or vaccine composition comprising the recombinant canine adenovirus (rCAdV) vector according to any of the above embodiments, and a pharmaceutical or veterinary-acceptable acceptable carrier or diluent.

In another aspect, the immunogenic or vaccine compositions comprising the recombinant canine adenovirus (rCAdV) vector according to any of the above embodiments is suitable for oral, intradermal, intramuscular or intranasal application.

The present invention further concerns a method of producing a immunogenic composition or vaccine comprising the recombinant canine adenovirus (rCAdV) vector according to any of the above embodiments for reducing the incidence or the severity of one or more clinical signs associated with or caused by an infection, comprising the following steps: (a) introducing into a host cell a recombinant rCAdV vector comprising the recombinant canine adenovirus (rCAdV) vector according to any of the above embodiments; (b) cultivating the infected cells under suitable conditions; (c) harvesting infected cells and/or vector and/or virus components; (d) optionally purifying the harvest of step (c); and (e) admixing said harvest with a pharmaceutically acceptable carrier.

The present invention further concerns a method of reducing or preventing the clinical signs or disease caused by an infection with a pathogen in an animal or for use in a method of treating or preventing an infection with a pathogen in an animal comprising the step of administering to the animal a therapeutically effective amount of the immunogenic composition of vaccine comprising the recombinant canine adenovirus (rCAdV) vector according to any of the above embodiments In a specific aspect according to any of the methods of the above embodiments, the immunogenic composition is administered once.

In a specific aspect according to any of the methods of the above embodiments, the immunogenic composition is administered as two doses.

In a specific aspect according to any of the methods of the above embodiments, the immunogenic composition is administered orally, intradermally, intramuscular or intranasally.

In a specific aspect according to any of the methods of the above embodiments, the immunogenic composition protects against a homologous and/or heterologous viral challenge.

The present invention further concerns a method of immunizing an animal against a clinical disease caused by a pathogen in said animal, comprising the step of administering to the animal the immunogenic composition comprising the recombinant canine adenovirus (rCAdV) vector according to any of the above embodiments, whereby the immunogenic composition or vaccine fails to cause clinical signs of infection but is capable of inducing an immune response that immunizes the animal against pathogenic forms of said pathogen.

In a specific aspect of the invention according to the above method, the immunogenic composition is administered once, or alternatively as two doses.

In a specific aspect of the invention according to the above method, the immunogenic composition is administered orally, intradermally, intramuscular or intranasally.

In a specific aspect of the invention according to the above method, the immunogenic composition protects against a homologous and/or heterologous viral challenge.

The present invention further concerns a kit for vaccinating an animal, against a disease associated with and/or reducing the incidence or the severity of one or more clinical signs associated with or caused by a pathogen in an animal comprising: (a) a dispenser capable of administering a vaccine comprising the recombinant canine adenovirus (rCAdV) vector according to any of the above embodiments to an animal; and (b) the immunogenic composition or vaccine comprising the recombinant canine adenovirus (rCAdV) vector according to any of the above embodiments, and (c) optionally an instruction leaflet.

The present invention further concerns a eukaryotic host cell line expressing the recombinant canine adenovirus type 2 (rCAdV2) of the above embodiments.

In another specific aspect the host cell line is a mammalian cell line or an insect cell line selected from the group consisting of a PK/WRL cell line, a RK13 cell line, a MDBK cell line, a ST cell line, an AI-ST cell line, a VERO cell line, a Sf9 cell line, a Sf21, a Sf plus cell line, a MDCK cell line, and/or derivatives thereof.

In yet another specific aspect the host cell line is a prokaryotic host cell line expressing the recombinant canine adenovirus type 2 (rCAdV2) of the above embodiments.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

Molecular Biology Definitions

The term "vector" as it is known in the art refers to a polynucleotide construct, typically a plasmid or a bacterial artificial chromosome, or attenuated live viral vectors used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382,425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051(recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 406; EPA0 370 573; U.S. application Ser. No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589, 466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism.

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions. Additionally, sequences may be "codon optimized" to improve the protein expression in living organism by increasing the translational efficiency of gene of interest. For example, a gene of interest can be mutated (or synthesized de novo) to change the codons used for coding particular amino acids, without changing the amino acid sequence of the protein itself. Rare codons can be replaced by codons that are more abundant in the genes of the host organism. Optimizing codons in the gene of interest may be the best way to increase the functionality and/or expression of the gene in the host cell background.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

Preferred viral vectors include canine adenoviral CAdV2 vectors.

According to specific aspects of the present disclosure, the term "viral vector" or alternatively "viral construct" refers to a recombinant viral construct derived from a virus, which is selected from the family of Adenoviridae (AdV) such as CAdV-1 and CAdV-2 (Canine Adenovirus), (see van Regenmortel, M. H. V., Fauquet, C. M., Bishop, D. H. L., Carstens, E. B., Estes, M. K., Lemon, S. M., Maniloff, J., Mayo, M. A., McGeoch, D. J., Pringle, C. R. and Wickner, R. B. (2000). Virus taxonomy. Seventh report of the International Committee on Taxonomy of Viruses. Academic Press, San Diego. 1162 pp).

The terms "viral vector" and "viral construct" can be used interchangeably.

The term "construct," as used herein, refers to a recombinant nucleic acid such as a plasmid, a BAC, or a recombinant virus that has been artificially generated.

The term "plasmid" refers to cytoplasmic DNA that is replicated independently of the bacterial chromosome within a bacterial host cell. In a specific aspect of the present invention the term "plasmid" and/or "transfer plasmid" and/or "transfer fragment" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid.

The term “nucleic acid”, “nucleic acid sequence”, “nucleotide sequence”, “polynucleotide”, “polynucleotide sequence”, “RNA sequence” or “DNA sequence” as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms “nucleic acid” and “polynucleotide” also specifically include nucleic acids composed of bases other than the five biologically occurring bases (adenine, guanine, thymine, cytosine and uracil).

The terms “regulatory nucleic acid”, “regulatory element” and “expression control element” are used interchangeably and refer to nucleic acid molecules that can influence the expression of an operably linked coding sequence in a particular host organism. These terms are used broadly to and cover all elements that promote or regulate transcription, including promoters, promoter sequences, core elements required for basic interaction of RNA polymerase and transcription factors, upstream elements, enhancers, and response elements. Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry sites (IRES), picornaviridal 2A sequences, and the like, that provide for and/or regulate expression of a coding sequence and/or production of an encoded polypeptide in a host cell.

An “internal ribosome entry site” or “IRES” describes a sequence which functionally promotes translation initiation independent from the gene 5' of the IRES and allows two cistrons (open reading frames) to be translated from a single transcript in an animal cell. The IRES provides an independent ribosome entry site for translation of the open reading frame immediately downstream of it. Unlike bacterial mRNA which can be polycistronic, i.e., encode several different polypeptides that are translated sequentially from the mRNAs, most mRNAs of animal cells are monocistronic and code for the synthesis of only one polypeptide. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an IRES operably linked to the second or subsequent open reading frame in the transcript allows the sequential translation of that downstream open reading frame to produce the two or more polypeptides encoded by the same transcript. The IRES can be of varying length and from various sources, e.g. Encephalomyocarditis virus (EMCV), picornaviruses (e.g. Foot-and-mouth disease virus, FMDV or Polio virus (PV), or Hepatitis C virus (HCV). Various IRES sequences and their use in vector construction have been described and are well known in the art. The downstream coding sequence is operably linked to the 3' end of the IRES at any distance that will not negatively affect the expression of the downstream gene. The optimum or permissible distance between the IRES and the start of the downstream gene can be readily determined by varying the distance and measuring expression as a function of the distance The term “2a” or “2a peptide” means short oligopeptide sequences, described as 2a and ‘2a-like’, serve as linkers which are able to mediate a co-translational cleavage between proteins by a process defined as ribosomal-skipping. Such 2a and ‘2a-like’ sequences (from Picornaviridae and other viruses or cellular sequences) can be used to concatenate multiple gene sequences into a single gene, ensuring their co-expression within the same cell (see Luke and Ryan, 2013).

As used herein, the term “promoter” or “promoter sequence” means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedron promoter.

As used herein in the context of the present invention the term promoter refers especially to a functional fragment e.g. a truncation of 4pgG600 (SEQ ID No. 29) or the complementary nucleotide sequence thereof, preferably the sequence identity is (at least) 72% over entire length (or higher). Furthermore, as used herein in the context of the present invention the term promoter refers especially to a functional fragment, e.g. a truncation of 4pMCP600 (SEQ ID No. 30) or the complementary nucleotide sequence thereof, preferably the sequence identity is (at least) 78% over entire length (or higher). Most preferably “promoter” refers to p430 (SEQ ID NO.:31) or p455 (SEQ ID NO.:32). The terms “p430”, “gG 430” and “430” are used synonymously and interchangeably throughout the specification, figures, sequence listing etc. The terms “p455”, “MCP 455” and “455” are used synonymously and interchangeably throughout the specification, figures, sequence listing etc.

The EHV-4 promoters are preferably truncated transcriptionally active promoter which comprises a region transactivated with a transactivating protein provided by the virus and the minimal promoter region of the full-length promoter from which the truncated transcriptionally active promoter is derived. For purposes of this specification, a “promoter” is composed of an association of DNA sequences corresponding to the minimal promoter and upstream regulatory sequences; a “minimal promoter” is composed of the CAP site plus TATA box (minimum sequences for basic level of transcription; unregulated level of transcription); and, “upstream regulatory sequences” are composed of the upstream element(s) and/or enhancer sequence(s). Further, the term “truncated” indicates that the full-length promoter is not completely present, i.e., that some portion of the full-length promoter has been removed. The truncated promoters in preferred embodiments are derived from the equine herpes virus-4 (EHV-4 genome referred to herein as 4pgG600 (SEQ ID NO.:29), 4pMCP600 (SEQ ID NO.:30), the truncated promoters are pgG430 (SEQ ID NO.:31) or gMCP455 (SEQ ID NO.:32), derived from the full-length sequences respectively.

The promoter can be truncated so that there is a 5%, 10%, 20% 21%, 22%, 23%, 24%, 25%, 26%, 27%, 28%, 29%, 30%, 31%, 32%, 33%, 34% 35%, 40%, 45%, 55%, 60%, 65%, 70%, 75%, 80% and even up to a 90% reduction in size, from a full-length promoter based upon base pairs; for instance, with the equine 4pgG600 (SEQ ID NO.:29), 4pMCP600 (SEQ ID NO.:30), respectively. Indeed, a truncated promoter of the invention can consist essentially of any region within the truncation which is transactivated by a transactivating protein provided by a virus or system into which the truncated promoter is inserted, and thus is a minimal promoter.

A truncated "transcriptionally active" or "competent" promoter of this invention refers to the truncated transcriptionally active eukaryotic herpesvirus promoters derived from the equine herpesvirus 4 genome: the EHV-4 gG430 (SEQ ID NO.:31) and gMCP455 (SEQ ID NO.:32) promoters. By "active" (or "competent"), the truncated transcriptionally active promoter should exhibit at least 80%, preferably at least 85%, more preferably at least 90%, and most preferably at least 95% of the transcriptional activity of the full length promoter. Deletion of nucleotides or of portions or of regions of the full length promoter can be done from the herein teachings, without undue experimentation, for generation of active fragments in addition to those exemplified.

A promoter useful in the practice of the invention consequently may include derivatives and/or sub-fragments of a full-length promoter that maintain adequate promoter activity and hence function as a promoter, and which may advantageously have promoter activity that is substantially similar to that of the actual or full-length promoter from which the derivative or sub fragment is derived. As used herein, the term "derivative" or "sub-fragment" refers to a nucleic acid sequence that has modifications such as truncations and/or substitutions/deletions such that the promoter sequence has substantially equivalent function when compared to the wild type promoter. These derivatives or subfragments include nucleic acid sequences having minor modifications which may be deliberate, as by site-directed mutagenesis, or may be spontaneous. The term "derivatives" further contemplates deletions, additions and substitutions to the sequence, so long as the promoter remains "transcriptionally active" or "competent" to drive expression of the operably linked polypeptide encoding an antigen of interest, for example.

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

The term "complementary nucleotide sequences" describes one strand of the two paired strands of polynucleotides such as DNA or RNA. The nucleotide sequence of the complementary strand mirrors the nucleotide sequence of its paired strand so that for each adenosine it contains a thymine (or uracil for RNA), for each guanine a cytosine, and vice versa. The complementary nucleotide sequence of e.g. 5'-GCATAC-3' is 3'-CGTATG-5' or for RNA 3'-CGUAUG-5'.

The terms "gene", "gene of interest", as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

By definition, an "epitope" is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. Specific, non-limiting examples of an epitope include a tetra- to penta-peptide sequence in a polypeptide, a tri- to penta-glyco side sequence in a polysaccharide. In the animal most antigens will present several or even many antigenic determinants simultaneously. Such a polypeptide may also be qualified as an immunogenic polypeptide and the epitope may be identified as described further.

An "epitope of interest" can be an antigen of a veterinary pathogen or toxin, or from an antigen of a veterinary pathogen or toxin, or another antigen or toxin which elicits a response with respect to the pathogen, of from another antigen or toxin which elicits a response with respect to the pathogen, such as, the non-limiting examples: a Paramyxovirus antigen, e.g. a canine distemper virus (CDV) antigen such a HA or F, Bovine Respiratory Syncytial Virus (BRSV) antigen, bovine parainfluenza virus 3 (bPIV3); a rabies glycoprotein, e.g., rabies glycoprotein G; an avian influenza antigen, e.g., turkey influenza HA, Chicken/Pennsylvania/

1/83 influenza antigen such a nucleoprotein (NP); a bovine leukemia virus antigen, e.g., gp51,30 envelope; a Newcastle Disease Virus (NDV) antigen, e.g., HN or F; a feline leukemia virus antigen (FeLV), e.g., FeLV envelope protein; a Herpesvirus glycoprotein, e.g., a glycoprotein from feline herpesvirus, equine herpesvirus, bovine herpesvirus, pseudorabies virus, or canine herpesvirus (canine herpesvirus glycoprotein gB, gC or gD); a flavivirus antigen, e.g., a West Nile virus or tick-borne encephalitis virus antigen; an immunodeficiency virus antigen, e.g., a feline immunodeficiency virus (FIV) antigen; a parvovirus antigen, e.g., canine parvovirus VP2 antigen; an equine influenza antigen; a Marek's Disease virus antigen; an poxvirus antigen, e.g., fowl pox virus antigen; an infectious bursal disease virus antigen, e.g., VP2, VP3, VP4; a coronavirus antigen, e.g. from porcine coronavirus (TGEV, PEDV and delta corona SPIKE Ags), canine, and/or feline, poultry (e.g. infectious bronchitis virus (IBV)); or a Pestivirus antigen e.g., Bovine viral diarrhea virus antigen.

The term "nucleotide sequence of interest" or "sequence of interest" as used herein is a more general term than gene of interest as it does not necessarily comprise a gene but may comprise elements or parts of a gene or other genetic information, e.g. ori (origin of replication). A nucleotide sequence of interest may be any DNA or RNA sequence independently of whether it comprises a coding sequence or not.

"Open reading frame" or "ORF" refers to a length of nucleic acid sequence, either DNA or RNA, that comprises a translation start signal or initiation codon, such as an ATG or AUG, and a termination codon and can be potentially translated into a polypeptide sequence.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription unit.

By the term "increased expression", "increased titer or productivity" or "improved expression or productivity" is meant the increase in expression, synthesis or secretion of a heterologous and/or exogenous sequence introduced into a host cell, for example of a gene coding for a therapeutic protein, by comparison with a suitable control, for example a protein encoded by a cDNA versus a protein encoded by an intron-containing gene. There is increased titer or productivity if a cell according to the invention is cultivated according to a method according to the invention described here, and if this cell has at least a 1.2-fold, a 1.5-fold, a two-fold, a three-fold, a four-fold or a five-fold increase in specific productivity or titer. There is also increased titer or productivity if a cell according to the invention is cultivated according to a method according to the invention described here, and if this cell has at least a 1.2-fold or at least a 1.5-fold or at least a two-fold or at least a three-fold increase in specific productivity or titer. There is also in particular increased titer or productivity if a cell according to the invention is cultivated according to a method according to the invention described here, and if this cell has at least a 1.2-fold to five-fold, preferably a 1.5-fold to five-fold, more preferably—two-fold to five-fold particularly preferably a three-fold to five-fold increase in specific productivity or titer. "Increased expression" may mean as well that more cells are actually expressing the gene/sequence of interest. For example expression may mean that the new promoters of the present invention is increased relative to expression effected by another promoter in terms of the number of recovered cells expressing or having detectable transgene expression. Increased expression may also mean an increase in the level of mRNA and/or protein detectable on a per cell basis.

An increased expression, titer or productivity may be obtained by using a heterologous vector according to the invention. This may be combined with other approaches such as a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous and/or exogenous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences or in vitro amplification systems based on DNA concatemers.

An assay to measure "increased expression" is LC-MS/MS-based protein measurements such as multiple reaction monitoring (MRM); antibody-based detection methods such as Western blot, dot blot, or Immunodiffusion, flow cytometry; and indirect immunofluorescence (IFA), and measures of biological activity by hemagglutination assay.

"Promoter activity" is measured indirectly by quantification of mRNA transcribed under control of the respective promoter. mRNA is quantified by RTqPCR relative to an endogenous standard.

The term "viral titer" is a measure of infectious units per volume of a virus preparation. Viral titer is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3' end of the eukaryotic mRNA and post-transcriptional incorporation of a sequence of about 100-200 adenine nucleotides (polyA tail) at the cleaved 3' end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as "exogenous", "exogenous sequence", "exogenous gene", "exogenous coding sequence", with respect to the host cell, when it comes from a different (virus) species. Accordingly, the EHV-4 based promoters of the present invention are exogenous in view of the CAdV vector. Any non-canine sequence or gene of interest such as a non-canine antigen is therefore an exogenous sequence or gene of interest or antigen according to a specific aspect of the present invention.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. As used herein in respect to a sequence or gene of interest such as an antigen, the term "heterologous" means that said sequence or gene of interest, specifically said antigen, is expressed out of its natural species context.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used exchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus, means a virus produced by artificial manipulation of the viral genome. A virus comprising a heterologous or an exogenous sequence such as an exogenous antigen encoding sequence is a recombinant virus. The term recombinant virus and the term non-naturally occurring virus are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

Furthermore, within the scope of the present description the terms "functional linking", "functionally linked" or "operably linked" means that two or more nucleic acid sequences or sequence elements are positioned in a way that permits them to function in their intended manner. For example, a promoter/enhancer or terminator is functionally linked to a coding gene sequence if it is able to control or modulate the transcription of the linked gene sequence in the cis position. Generally, but not necessarily, the DNA sequences that are functionally linked are contiguous and, where necessary to join two polypeptide coding regions or in the case of a secretion signal peptide, contiguous and in reading frame. However, although an operably linked promoter is generally located upstream or an operably linked terminator is generally located downstream of the coding sequence, it is not necessarily contiguous with it. Enhancers do not have to be contiguous as long as they increase the transcription of the coding sequence. For this they can be located upstream or downstream of the coding sequence and even at some distance. A polyadenylation site is operably linked to a coding sequence if it is located at the 3' end of the coding sequence in a way that transcription proceeds through the coding sequence into the polyadenylation signal. Linking is accomplished by recombinant methods known in the art, e.g. by ligation at suitable restriction sites or blunt ends or by using fusion PCR methodology. Synthetic oligonucleotide linkers or adapters can be used in accord with conventional practice if suitable restriction sites are not present.

Accordingly, the term "functional fragment or derivative"" of a promoter sequence means that the fragment or derivative still effects promoter activity. Functional assays of how to assess promoter activity are well known to one of ordinary skill in the art (Bustin, S. 2000. Absolute quantification of mRNA using real-time reverse transcription polymerase chain reaction assays. Journal of Molecular Endocrinology 25(2): 169-193; Nolan, T. Rebecca E Hands, R. E., and Bustin S. A. 2006. Quantification of mRNA using real-time RT-PCR Nature Protocols 1: 1559-1582). An exemplary embodiment of such a functional assay includes e.g., a promoter kinetics experiment. Cells infected with vector viruses carrying expression cassettes where a promoter or fragment thereof directs transcription of a reporter transgene are incubated for different times. Total RNA is prepared from samples collected at different times after infection. After destruction of contaminating DNA by DNase I digestion, the RNA is reverse transcribed. One replicate sample is processed with addition of reverse transcriptase (RT), the second replicate is processed without addition of RT in order to demonstrate successful removal of contaminating DNA from the RNA preparation. The resulting cDNA is purified and used as template in a conventional PCR. Only the samples processed with the addition of RT shall produce a PCR product. These cDNAs can then be used for qPCR with primers for the reporter transgene and in parallel with primers for an essential gene of the viral vector (internal standard gene), the transcription of which provides an internal standard for the efficiency of infection and replication. qPCR values of the reporter are normalized between the different constructs and times after infection using the qPCR values of the internal standard gene. This allows an interpretation of promoter activities of different promoters and fragments thereof.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, 91%, 92%, 93%, 94%, even more preferably 95%, 96%, 97%, 98%, 99%, 99.9% of the amino acid residues or nucleotides in the reference sequence must match or comprise a conservative substitution with another amino acid or nucleotide, or a number of amino acids or nucleotides up to 15%, preferably up to 10%, 9%, 8%, 7%, 6%, even more preferably up to 5%, 4%, 3%, 2%, 1%, 0.1% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at www.accelrys.com), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at www.ncbi.nlm.nih.gov.

EHV-1, EHV-4, & CAdV/Recombinant Vector Technology Definitions

The term "equid" or "equine" or "equin" means of or belonging to the family Equidae, which includes the horses, asses, and zebras, preferably horses. In addition, the term "equid" or "equine" or "equin" encompasses also hybrids of members of the family Equidae (e.g. mules, hinnies, etc.).

A "herpes virus" or "herpes virus vector" refers to a species in the family Herpesviridae in the order Herpesvirales.

The term "equid herpes virus vector" or "equid herpes virus" means a member of the family Herpesviridae affecting horses. To date eight different species of equid herpesviruses have been identified, five belonging to the subfamily alphaherpesvirinae and three to the gammaherpesvirinae. (www.ictvonline.org Virus Taxonomy: 2015 Release EC 47, London, UK, July 2015; Email ratification 2016 (MSL #30)).

The term "EHV-1" means Equid herpesvirus 1, a member of the subgenus Varicellovirus in the genus Alphaherpesvirinae in the family Herpesviridae. A non-limiting reference sequence for EHV-1 would be for example the wild-type EHV-1 strain ab4 (Genbank accession number AY665713.1) or the RacH (Hübert, P. H., Birkenmaier, S., Rziha, H.-J. and Osterrieder, N. (1996), Alterations in the Equine Herpesvirus Type-1 (EHV-1) Strain RacH During Attenuation. Journal of Veterinary Medicine, Series B, 43: 1-14.).

The term EHV-4 means Equid herpesvirus 4, a member of the subgenus Varicellovirus in the genus Alphaherpesvirinae in the family Herpesviridae.

The term "CAdV", "CAV", "CAV-1" or "CAV-2" means Canine adenovirus type-1 or type-2, respectively, a member of the genus Mastadenovirus, in the family Adenoviridae. However, according to the newer taxonomy (www.ictvonline.org Virus Taxonomy: 2015 Release EC 47, London, UK, July 2015; Email ratification 2016 (MSL #30)) the term canine adenovirus (CAdV) now encompasses both species CAV-2 and CAV-1.

A "recombinant CAdV vector" or "rCAdV" and/or "rCAdV vector" or "rCAdV" or "rCAdV2" refers to a canine adenovirus comprising at least one exogenous expression cassette (i.e. containing encoding sequences in operable linkage with promoters, enhancers, and other suitable regulatory elements), such as encoding a transgene expression marker (such as green fluorescent protein), and in preferred embodiments at least one "gene of interest" and/or "epitope of interest".

The rCAdV vector can be produced by standard methods known to persons of ordinary skill in the field of virology and molecular biology. However to facilitate manipulation of the CAdV genome and production of the vector, the invention also provides a bacterial shuttle vector, in one none limiting example thepBR322 plasmid, containing the nucleic acid encoding the CAdV genome Additionally, a bacterial artificial chromosome ("BAC"), may also facilitate manipulation of the CAdV in a bacterial system.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The invention still further provides an "immunogenic composition", or "vaccine composition" containing the recombinant CAdV virus or vector, and a pharmaceutically acceptable carrier or diluent. An immunogenic composition containing the recombinant CAdV virus or vector (or an expression product thereof) elicits an immunological response—local or systemic. The response can, but need not be, protective. A vaccine composition elicits a local or systemic protective response. Accordingly, the term "immunogenic composition" includes a "vaccine composition" (as the two former terms can be protective compositions).

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

By "animal" it is intended mammals, human, birds, and the like. The animal may be selected from the group consisting of equine (e.g., horse, zebra, donkey), canine (e.g., dogs, wolves, foxes, coyotes, jackals), feline (e.g., lions, tigers, domestic cats, wild cats, other big cats, and other feline including cheetahs and lynx), ovine (e.g., sheep), bovine (e.g., cattle, cow, buffalo), swine (pig), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages. The term "food producing animal" means non-canine animals which are used for human consumption such as bovine, porcine, equine, poultry, ovine fish and the like, preferably food producing animal means swine and cattle, most preferably swine.

Examples of non-canine companion animals include feline species.

For administration to non-canine animals, recombinant CAdV, provides the advantage of expression without productive replication. Replication of the canine adenovirus is limited to canine species and there are no reports in the literature of CAdV2 causing a productive infection in any non-canine species including man. This host restriction provides an inherent safety barrier to transmission of the virus to other species and makes the use of CAdV2 based vaccine vectors in veterinary applications across species an attractive proposition. Therefore, the invention comprehends methods for amplifying or expressing a protein by administering or inoculating a host with a recombinant CAdV2 virus or vector, whereby the host is not a canine or not a natural host of the recombinant virus or vector, and/or there is expression without productive replication and/or with a limited replicative cycle.

For administration to canine animals, since CAdV, and especially CAdV2, is used as vaccinial strains in dogs, the present invention provides a means for introducing additional epitope(s) of interest e.g., antigen(s) of a canine pathogen(s) or toxin(s). Expression of additional epitope(s) of interest encoded in the rCAdV2 vector thereby provides a means to elicit in vivo responses to those epitope(s) of interest as well as the canine adenovirus by inoculating a dog or pup with the vaccinial recombinant CAdV2. The additional epitope(s) of interest can be an antigen of a canine pathogen (other than adenovirus), from an antigen of a canine pathogen (other than adenovirus), another antigen which elicits a response in dogs or pups to the canine pathogen (other than adenovirus), or from another antigen which elicits a response in dogs or pups to the canine pathogen (other than adenovirus).

Accordingly the present invention provides that the recombinant CAdV2 can contain heterologous DNA encoding an epitope of interest from any antigen of a canine pathogen example: rabies, canine herpesvirus, canine distemper virus, canine parvovirus, etc. Embodiments of the invention include CAdV recombinants containing exogenous DNA coding for more than one protein, e.g., coding for two or more epitopes such as antigens of canine pathogens. The invention also envisions compositions containing CAdV recombinants in combination with other antigens.

For administration to non-canine animals, the present invention provides a means for introducing an epitope of interest wherein the antigenic epitope of interest is an antigen derived from a food producing animal pathogen such those selected from the group of bovine pathogens: Bovine viral diarrhea virus (BVDV), Parainfluenza-3 Virus (PI-3), Infectious Bovine Rhinotracheitis virus (IBR), Bovine Respiratory Syncytial Virus (BRSV), Bovine Herpesvirus (BHV), Bovine Rotavirus (BRV), Bovine Enterovirus (BEV), Bovine Coronovirus (BCV), Bovine Rabies (BR), Bovine Parvovirus (BPV), Adenovirus Astrovirus, *Mannheimia haemolytica* (formerly *Pasteurella haemolytica*), *Pasteurella multocida, Haemophilus somnus* (*Histophilus ovis* and *Haemophilus agni*), *Actinomyces* (*Corynebacterium*), *Actinomyces pyogenes, Chlamydia psittaci, Campylobacter fetus venerealis* and *Campylobacter fetus fetus* (formerly *C fetus intestinalis*), *Leptospira interrogans, Leptospira hardjo, Leptospira pomona*, and *Leptospira grippotyphosa, Leptospira canicola, Leptospira grippotyphosa, Leptospira hardjo* (*Leptospira hardjoprajitno* and *Leptospira hardjo-bovis*), *Brucella abortus, Brucella suis* and *Brucella melitensis, Listeria monocytogenes, Chlamydia psittaci, Clostridium chauvoei, Clostridium septicum, Clostridium haemolyticum, Clostridium novyi, Clostridium sordellii, Clostridium perfringens, Clostridium tetani, Moraxella bovis, Klebsiella* spp, *Klebsiella pneumoniae, Salmonella typhimurium; Salmonella newport, Mycobacterium avium* ssp. paratuberculosis, *Cryptsporidium parvum, Cryptsporidium hominis, Staphylococcus aureus, Streptococcus dysgalactiae, Streptococcus uberis, Streptococcus agalactiae, Escherichia coli, Mycoplasma* spp, *Mycoplasma dispar*, and *Ureaplasma* spp., *Tritrichomonas foetus, Trichophyton verrucosum, Trichophyton mentagrophytes, Trichophyton sarkisovii, Neospora caninum* (formerly *Toxoplasma gondii*), *Babesia bigemina* and *Babesia bovis, Dictyocaulus viviparous* (Lungworm disease), and combinations thereof. For administration to non-canine animals, the present invention provides a means for introducing an epitope of interest wherein the antigenic epitope of interest is an antigen derived from a food producing animal pathogen such those selected from the group of porcine pathogens: *Salmonella* spp., in particular *S. typhimurium S. choleraesuis*; Astroviruses; Rotavirus; Transmissible gastroenteritis virus; *Brachyspira* spp., in particular *B. hyodysenteriae, B. pilosicoli; Clostridium* spp., in particular *C. difficile, C. perfringens* types A, B and C, *C. novyi, C. septicum, C. tetani*; Porcine enteric picornaviruses; Porcine enteric caliciviruses; respiratory pathogens, which include: *Actinobacillus pleuropneumonia; Bordetella bronchiseptica; Erysipelothrix rhsiopathiae; Haemophilus parasuis*, in particular subtypes 1, 7 and 14; *Pasteurella* spp., in particular *P. multocida; Mycoplasma* spp., in particular *M. hyopneumoniae, M. hyorhinis*; Swine influenza A virus; PRRS virus; Porcine circovirus; Porcine parvovirus; Pseudorabies virus; *Eperythrozoonosis suis, Mycobacterium* spp., in particular *M. avium, M. intracellulare, M. bovis*; Porcine respiratory corona virus; Porcine coronavirus in particular TGEV, PEDV, and delta coronavirus; *Arcanobacterium pyogenes*; Porcine adenovirus; Classical swine fever; Porcine cytomegalovirus; African swine fever; or other pathogens, which include *Escherichia coli, Streptococcus* spp., in particular *S. suis, S. porcinus, S. dysgalactiae*, preferably subsp. *equisimilis; Brucella suis*, in particular biovars 1, 2 and 3; *Leptospira* spp., in particular *L. australis, L. canicola, L. grippotyphosa, L. pomona, L. icterohaemorrhagicae, L. interrogans, L. tarassovi, L. hardjo, L. sejroe*; Encephalomyocarditis virus; Hemagglutinating encephalomyelitis virus; Japanese encephalitis virus; West Nile virus; Reovirus; Rubulavirus; Menangle virus; Nipah virus; Vesicular stomatitis virus; Virus of vesicular exanthema of swine; Swine pox virus; Swine herpes virus; and *Staphylococcus hyicus*, and combinations thereof.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate or kill such virus or bacterium while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

More particularly, the term "inactivated" in the context of a virus means that the virus is incapable of replication in vivo or in vitro and, respectively, the term "inactivated" in the context of a bacterium means that the bacterium is incapable of reproduction in vivo or in vitro. For example, the term "inactivated" may refer to a virus that has been propagated in vitro, and has then been inactivated using chemical or physical means so that it is no longer capable of replicating. In another example, the term "inactivated" may refer to a bacterium that has been propagated, and then inactivated using chemical or physical means resulting in a suspension of the bacterium, fragments or components of the bacterium, such as resulting in a bacterin which may be used as a component of a vaccine.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or anti-parasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

For recombinant viral vector-based vaccines, the routes of administration may advantageously be SC, IM, TD, or ID. This administration may be made by a syringe with a needle or with a needle free apparatus. Embodiments of the invention can be administered orally, internasally, anally, vaginally, perorally, intragastrically, parenterally, subcutaneously, intradermally, intramuscularly or intravenously. Examples of compositions of the invention include liquid preparations for orifice, e.g., oral, nasal, anal, vaginal, peroral, intragastric, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant CAdV2 and/or antigens may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired.

In one aspect, the present invention relates to a vaccine strategy, which is based on a "prime-boost" administration regimen, where the prime-administration and the boost-administration utilize a composition comprising a pharmaceutically or veterinary acceptable excipient, diluent, adjuvant, or vehicle and the recombinant CAdV of the present invention A prime-boost regimen comprises at least one prime-administration and at least one boost administration using at least one common antigen and/or variants or fragments thereof. The vaccine used in prime-administration may be different in nature from those used as a later booster vaccine. It is further noted that both the prime-administration and the boost-administration may comprise the recombinant CAdV of the present invention. The prime-administration may comprise one or more administrations. Similarly, the boost-administration may comprise one or more administrations.

Another aspect of the present invention relates to a kit for prime-boost vaccination according to the present invention. The kit may comprise at least two vials: a first vial containing a vaccine for the prime-vaccination according to the present invention, and a second vial containing a vaccine for the boost-vaccination according to the present invention. The kit may advantageously contain additional first or second vials for additional prime-vaccinations or additional boost-vaccinations.

In one embodiment, the kit may comprise two vials, one containing a plasmid-based vaccine for the prime-vaccination according to the present invention, the other vial containing a recombinant viral vector-based vaccine for the boost-vaccination according to the present invention.

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John-Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

“Diluents” can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

“Isolated” means altered “by the hand of man” from its natural state, i.e., if it occurs in nature, it has been changed or removed from its original environment, or both. For example, a polynucleotide or polypeptide naturally present in a living organism is not “isolated,” but the same polynucleotide or polypeptide separated from the coexisting materials of its natural state is “isolated”, as the term is employed herein.

“Attenuation” means reducing the virulence of a pathogen. In the present invention “attenuation” is synonymous with “avirulent”. In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus, especially the CAdV viral vector as claimed, in comparison with a “control group” of animals infected with non-attenuated virus or pathogen and not receiving the attenuated virus. In this context, the term “reduce/reduced” means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the CAdV viral vector as claimed, is suitable for the generation of a modified live vaccine (MLV) or modified live immunogenic composition.

Herein, “effective dose” means, but is not limited to, an amount of antigen that elicits, or is able to elicit, an immune response that yields a reduction of clinical symptoms in an animal to which the antigen is administered.

As used herein, the term “effective amount” means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term “effective amount” refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An “immune response” or “immunological response” means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion. The invention therefore also provides a method of “inducing an immunological response” in a host vertebrate comprising administering to the host an immunogenic or vaccine composition comprising the recombinant CAdV virus or vector and a pharmaceutically acceptable carrier or diluent.

“Protection against disease”, “protective immunity”, “functional immunity”, “reduction of clinical symptoms”, “inducing an immunological response”, “induction/production of neutralizing antibodies and/or serum conversion”, and similar phrases, means antibody production against the antigen, and/or resulting in a partial or complete response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

The term "reduction of viremia" induced by a virus means, but is not limited to, the reduction of virus entering the bloodstream of an animal, wherein the viremia level, i.e. the number of virus DNA or RNA copies per mL of blood serum or the number of plaque forming colonies per deciliter of blood serum, is reduced in the blood serum of animals receiving the composition of the present invention by at least 50% in comparison to animals not receiving the composition and may become infected. More preferably, the viremia level is reduced in animals receiving the composition of the present invention by at least 90%, preferably by at least 99.9%, more preferably by at least 99.99%, and even more preferably by at least 99.999%.

As used herein, the term "viremia" is particularly understood as a condition in which virus particles reproduce and circulate in the bloodstream of an animal, in particular of a mammal, a bird, or of an insect.

"Safety" refers to the absence of adverse consequences in a vaccinated animal following vaccination, including but not limited to: potential reversion of a bacterium-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in said animal.

"Mortality", in the context of the present invention, refers to death caused by an infection, and includes the situation where the infection is so severe that an animal is euthanized to prevent suffering and provide a humane ending to its life.

Formulations

The subject to which the composition is administered is preferably an animal, including but not limited to cattle, horses, sheep, pigs, poultry (e.g. chickens), goats, cats, dogs, hamsters, mice and rats, most preferably the mammal is a swine.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitnoeally, intracutaneously, and depending on the desired duration and effectiveness of the treatment, the compositions according to the invention may be administered once or several times, also intermittently, for instance on a daily basis for several days, weeks or months and in different dosages such as about $10^3$ to $10^8$ TCID50 (see viral titer above). In a specific aspect of the present invention the dosage is about $10^3$ to $10^8$ TCID50, especially for live virus/live vaccine.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 15: Flow Cytometric Analysis of CAdV2 CMVie CPV VP2-infected AI-ST 2015 cells: 72 h post-infection FIG. 16: rCAdV-2 with New EHV-4 Promoters: Flow Cytometric Analysis of Infected AI-ST 2015 cells: 48 h post-infection

FIG. 18: RabG detection in cells infected with rCAdV-2 p455 RabG: expression is detected in <1% of cells infected with original rCAdV-2 CMVie RabG.

FIG. 18. Summary of Flow Cytometric analysis of RabG proteins express by AI-ST 2015 cells infected by rCAdV-2 infectious clones.

FIG. 19A: Detection of CPV VP2 in cells infected with rCAdV-2 p430 and p455 (denoted as gG430 and MCP455, respectively) RabG.

FIG. 19B: Detection of RabG in cells infected with rCAdV-2 p455 (denoted as MCP455) RabG.

FIG. 19C: Detection of both CAdV-2 and RabG in cells infected with rCAdV-2 p455 (denoted MCP455) RabG.

SEQUENCES OVERVIEW

Figure 1:
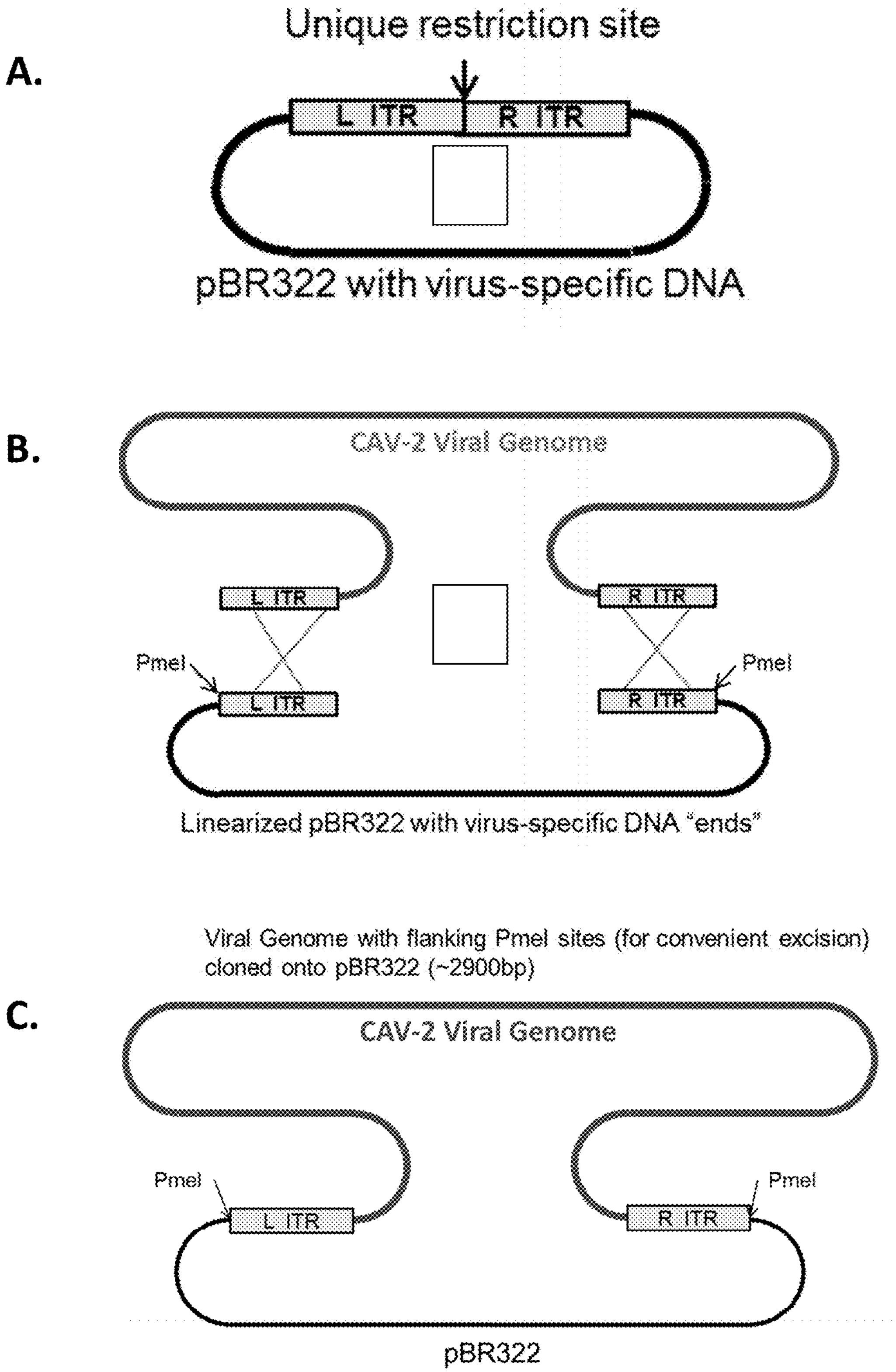
FIG. 1. Schematic drawing of the generation of a CAdV2 Infectious Clone. (A) Synthesized DNA fragment encoding 5' and 3' ends of the viral genome with intervening unique restriction site and cloned into pBR322 *E. coli* shuttle vector. PmeI restriction endonuclease sites (arrows) were engineered into the construct at the 5' and 3' ends of the ITRs to facilitate excision of the CAdV-2 genome from the pBR322 vector backbone. (B) B. Cloned dsDNA CAdV-2 genome onto vector via homologous recombination in BJ5183 $REC^+$ *E. coli.* (C) Successful HR-recombinant rCAdV-2 infectious clone. ITR=inverted terminal repeat.

The following sequences are detailed and disclosed hereby in the present invention:

TABLE 1

| SEQ. IDENTIFIER | NAME | DNA/RNA/ PROTEIN |
|---|---|---|
| SEQ ID NO: 1 | CAdV2 ΔE3A-E3 region | DNA |
| SEQ ID NO: 2 | CAdV2 ΔE3B-E3 region | DNA |
| SEQ ID NO: 3 | huCMVie promoter | DNA |
| SEQ ID NO: 4 | huCMV 5 promoter | DNA |
| SEQ ID NO: 5 | huCMVie 5' F primer | Artificial |
| SEQ ID NO: 6 | huCMVie 3' R primer | Artificial |
| SEQ ID NO: 7 | huCMVie EGFP Expression Casette | DNA |
| SEQ ID NO: 8 | EGFP Forward (PCR Screen Primer) | Artificial |
| SEQ ID NO: 9 | EGFP Reverse (PCR Screen Primer) | Artificial |
| SEQ ID NO: 10 | huCMVie CPV VP2 (n) Expression Casette | DNA |
| SEQ ID NO: 11 | Set 1 H-AP VIII F Primer (FIG. 10E) | Artificial |
| SEQ ID NO: 12 | Set 1 VP2 RPrimer (FIG. 10E) | Artificial |
| SEQ ID NO: 13 | Set 2 VP2 F Primer (FIG. 10E) | Artificial |
| SEQ ID NO: 14 | Set 2U Exon R Primer (FIG. 10E) | Artificial |
| SEQ ID NO: 15 | Set 3 VP2 F Primer (FIG. 10E) | Artificial |
| SEQ ID NO: 16 | Set 3 VP2 R- Primer (FIG. 10E) | Artificial |
| SEQ ID NO: 17 | Set 4 VP2F-Primer (FIG. 10E) | Artificial |
| SEQ ID NO: 18 | Set 4 VP2 R Primer (FIG. 10E) | Artificial |
| SEQ ID NO: 19 | Set 5VP2F-Primer (FIG. 10E) | Artificial |
| SEQ ID NO: 20 | Set 5VP2R-Primer (FIG. 10E) | Artificial |
| SEQ ID NO: 21 | Set 6H-AP VIIIF Primer (FIG. 10E) | Artificial |
| SEQ ID NO: 22 | Set 6U Exon Reverse Primer (FIG. 10E) | Artificial |
| SEQ ID NO: 23 | huCMVie CPV VP2 (co) Expression Casette | DNA |
| SEQ ID NO: 24 | Canine Parvovirus VP2 Protein | Protein |
| SEQ ID NO: 25 | huCMVie RabGP Expression Cassette | DNA |
| SEQ ID NO: 26 | Pasteur Rabies G (n) glycoprotein | Protein |
| SEQ ID NO: 27 | huCMVie BRSV F (co) Expression Cassette | DNA |
| SEQ ID NO: 28 | BRSV F (co) Polypeptide | Protein |
| SEQ ID NO: 29 | EHV-4 600 bp Promoter (4pgG600) | DNA |
| SEQ ID NO: 30 | EHV-4 600 bp Promoter (4pMCP600) | DNA |
| SEQ ID NO: 31 | EHV-4 430 bp Promoter (pG430) | DNA |
| SEQ ID NO: 32 | EHV-4 MCP455 bp Promoter (p455) | DNA |
| SEQ ID NO: 33 | gG430 F Primer | Artificial |
| SEQ ID NO: 34 | gG430 R Primer | Artificial |
| SEQ ID NO: 35 | MCP455 F Primer | Artificial |
| SEQ ID NO: 36 | MCP455 R Primer | Artificial |
| SEQ ID NO: 37 | CPV VP2 Despliced ORF with BamHI and SalI Restriction Endonuclease Sites | DNA |
| SEQ ID NO: 38 | CPV VP2 Gen0.95 ORF with BamHI and SalI Restriction Endonuclease Sites | DNA |
| SEQ ID NO: 39 | p430 CPV VP2 (Despliced) Expression Casette | DNA |
| SEQ ID NO: 40 | p430 CPV VP2 (Gen 0.95) Expression Casette | DNA |
| SEQ ID NO: 41 | p455 CPV VP2 (Gen0.95) Expression Casette | DNA |
| SEQ ID NO: 42 | p430 RabG (n) Expression Casette | DNA |
| SEQ ID NO: 43 | p455 RabG (n) Expression Casette | DNA |
| SEQ ID NO: 44 | Despliced Forward Primer | Artificial |
| SEQ ID NO: 45 | Despliced Reverse Primer | Artificial |
| SEQ ID NO: 46 | Gen0.95 Forward Primer | Artificial |
| SEQ ID NO: 47 | Gen0.95 Reverse Primer | Artificial |

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

CAdV Virus Isolation

The CAdV2 virus was originally isolated from a throat swab from a dog with laryngotracheitis and was obtained as the first passage in American Type Culture Collection (ATCC) MDCK cell line CCL-34. The virus was passed 8 times after acquisition, and the $8^{th}$ passage was aliquoted and designated as the Master Seed Virus. The stock CAdV-2 Master Seed Virus was produced at Boehringer Ingelheim Vetmedica, Inc. under the reference CAdV-2, MSV Lot #001-dil, F: 11-24-98. The stock CAdV-2 Master Seed is closely related to the Toronto strain (Genbank Accession Number U77082.1). CAdV-2 is commercially available from Boehringer Ingelheim Vetmedica, Inc. as a canine vaccine.

The infectious clone DNA is the entire CAdV-2 genome cloned into the pBR322 low copy *E. coli* shuttle vector. A homologous recombination approach (Kremer, E. J., et al., Canine adenovirus vectors: an alternative for adenovirus-mediated gene transfer. J Virol, 2000. 74(1): p. 505-12.) was employed to construct the infectious clone DNAs. CAdV-2 DNA was purified from stock CAdV-2 MLV) and recombined in BJ5183 *E. coli* with a pBR322-based vector containing DNA homologous to the CAdV-2 Inverted Terminal Repeats.

CAdV-2 was rescued from Madine Darby canine kidney (MDCK) cells transfected with linearized infectious clone DNA FIG. 1 for a representation of the complete infectious clone DNA.

Example 2

Generation of E3-Deleted-Insertion CADV Clones

CAdV-2 has been successfully utilized as a vectored viral vaccine for animals. The E3 domain of CAdV-2 is known to be non-essential (none of the E3 open reading frames (ORFs) is required for viral replication in tissue culture (Fisher et al. 2002) and present a logical target for the insertion of heterologous DNAs.

Examples of efficacious CAdV-2-based vaccines wherein transgenes are localized to the E3 domain include canine distemper virus (Fisher et al. 2002), feline panleukopenia virus (Yang et al. 2008), and rabies for cats (Hu et al., 2007), dogs (Hu et al., 2006) mice (Li et al., 2006), raccoons, swine (Lui et al., 2008), skunks (Henderson et al., 2009) and sheep (Bouet-Cararo et al., 2011).

Figure 2:
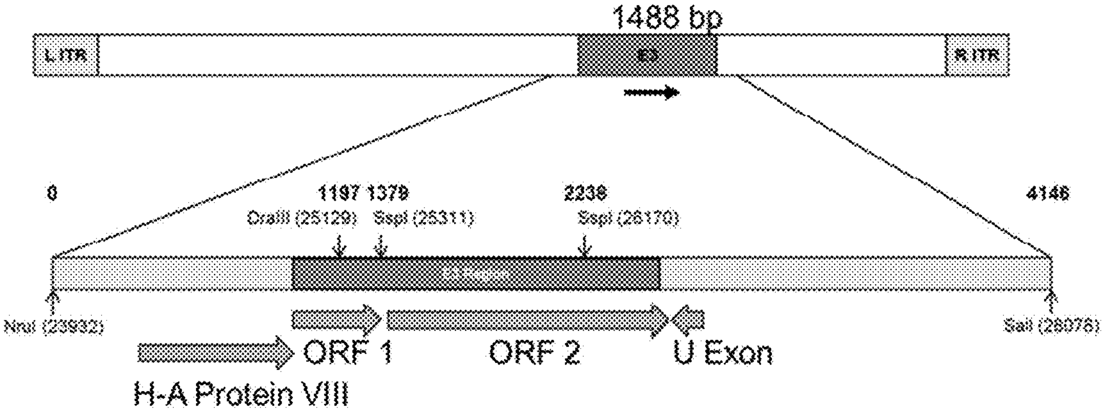
FIG. 2. Schematic of the organization of the E3 region of CAdV-2.

FIG. 2 is a schematic of the organization of the E3 region of CAdV-2. The 4146 bp NruI (bp 23932)/SalI (bp 28078) restriction endonuclease fragment is illustrated with open reading frames (ORFs) shown as the H-A Protein VIII, ORF1, ORF2, and the U Exon. The positions of select restriction endonuclease sites (NruI, DraIII, SspI and SalI) are shown for this DNA fragment and the numbering is relative to the closely related Toronto strain (Genbank Accession Number U77082.1) of CAdV-2.

As noted by Fischer et al. (2002), the genomic organization of E3 regions is only loosely conserved between different adenoviruses (Linne, T., Differences in the E3 regions of the canine adenovirus type 1 and type 2. Virus Res, 1992. 23(1-2): p. 119-33), and therefore, the precise limits of the CAdV2 E3 region nonessential loci cannot be transposed from E3 insertion sites in other viruses. In a first construct the entire ORF1 and ORF2 DNA segment from E3 was deleted to maximize the size of the transgene insertions, however infectious clone DNAs failed to facilitate rescue of rCAdV-2. This strategy was found to inadvertently delete the last five codons (including the stop codon) of the hexon-associated protein VIII gene (H-A-PVIII) that extends into E3 ORF1 (different reading frame) in the 5' E3 Flank DNA, resulting in an H-A PVIII gene with a substantial 3' extension (could result in an H-A PVIII with a 5 amino acid deletion followed by a substantial c-terminal addition).

Thus the transfer plasmids were redesigned so that the 5' and 3' E3 Flanking DNAs contained the first 183 bp of E3 ORF1 and the last 47 bp of ORF2, which were found to be sufficient for rCAdV-2 rescue.

Example 3

Homologous Recombination for Generation of RCADV-2 Infectious Clone DNAS

Figure 3:
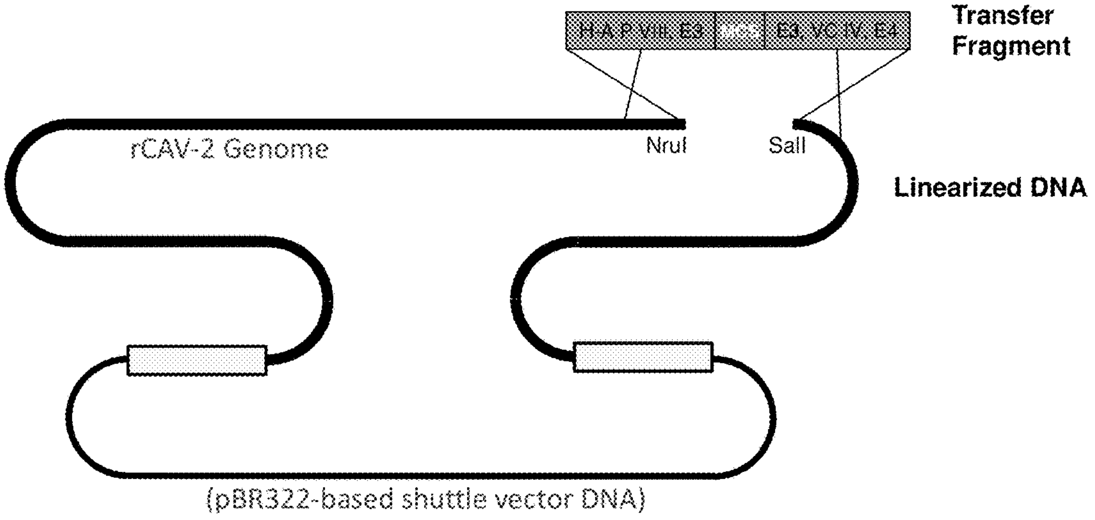
FIG. 3. Schematic illustration of homologous recombination between a linearized infectious clone DNA and a E3-targeting CAdV-2 transfer fragment.

Homologous recombination in Rec+ BJ5183 *E. coli* between linearized CAdV-2 infectious clone DNAs and E3-targeting CAdV-2 transfer plasmids/fragments, based on methods described in papers by Chartier et al. (1996) and Kremer et al. (2000), was employed for the generation of rCAdV-2 with transgene expression cassettes localized to the E3 domain. As illustrated in FIG. 3, an infectious clone that contains a unique restriction site in the E3 domain recombines with a transfer fragment containing ~500 bp of CAdV-2 flanking DNA both 5' and 3' to transgene expression cassettes to both a) target the transgene expression cassette to the E3 region and b) effectively delete select portions of E3.

DNA was isolated from expanded BJ5183 clones identified using a transgene-specific PCR screen, and these DNAs were resolved by agarose gel electrophoresis to verify their migration at or >23.1 Kb (successful HR results in DNA species of ~35 kb which as a supercoiled DNA migrates similarly to the 23.1 kb marker on a 0.7% agarose gel). These DNA were then transformed and expanded in either Stb12 or XL-10 Gold *E. coli* for larger scale purification and use for generation of rCAdV-2 in mammalian cells.

FIG. 3 is a schematic illustration of homologous recombination between a NruI/SalI-linearized infectious clone DNA (native CAdV-2 sequence) and an E3-targeting CAdV-2 transfer fragment encompassing the aforementioned E3 deletion and a unique restriction site or sites (designated MCS for multiple cloning site) located between the remaining portions of E3. The infectious clone DNA is bordered by the left and right inverted terminal repeats, LITR and RITR, respectively.

Example 4

Generation of ΔE3 rCAdV-2 Infectious Clone DNAs

E3-Deleted rCAdV-2: ΔE3A and ΔE3B

Figure 4:
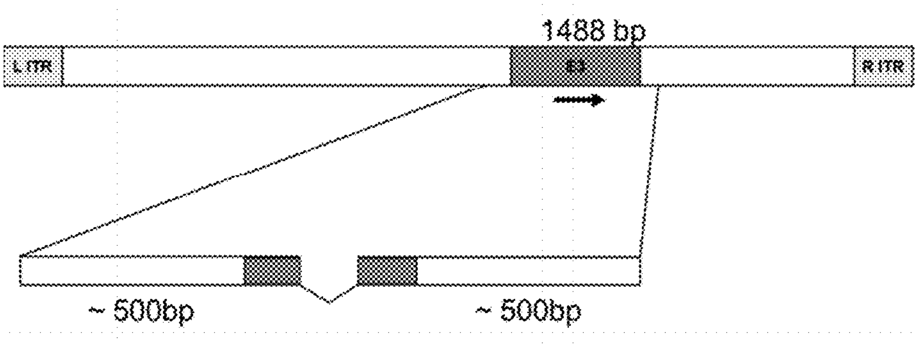
FIG. 4. Schematic of the BIVI-generated E3-deletion (ΔE3A and ΔE3B) Transfer Fragment(s) in the CAdV-2 backbone.
Figure 5:
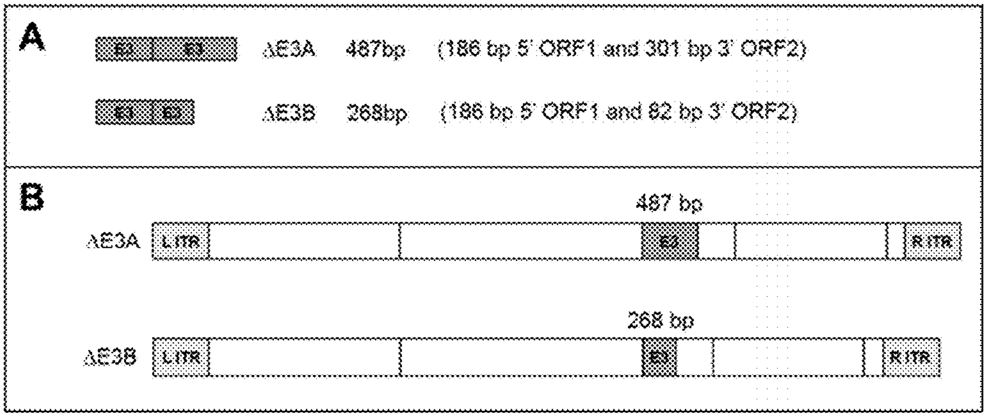
FIG. 5. Schematic of the BIVI-generated E3-deletions. A) Schematic of the E3 ORFs with total combined sizes of remaining ORF1 and 2 DNAs and the amounts of each. B) Schematic of the CAdV-2 genome indicating the total amount of E3 ORF1 and ORF2 DNA remaining in ΔE3A and ΔE3B configurations. In the "A" deletion (ΔE3A) all but the first 186 nucleotides of E3 ORF1 and the last 301 nucleotides of ORF2 were deleted, while for the E3 "B" deletion (ΔE3B) 186 nucleotides of E3 ORF1 and 83 nucleotides of ORF2 remain.
Figure 6:
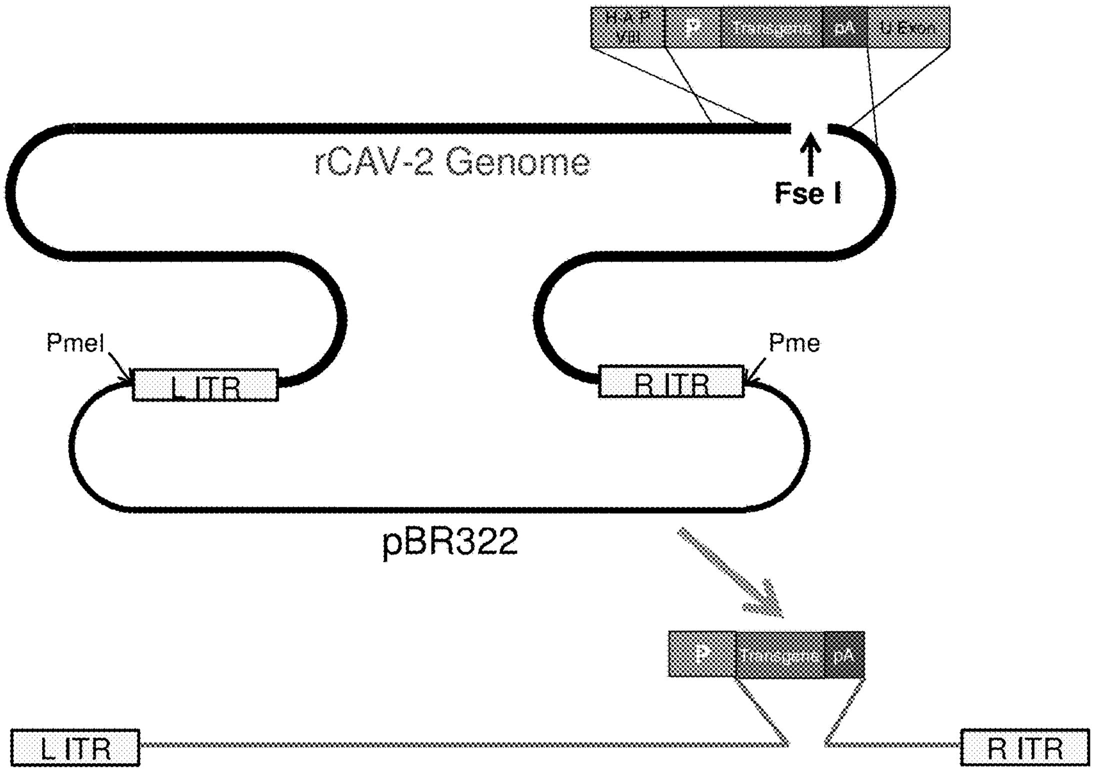
FIG. 6. E3 Deletion and Insertion of Expression Cassettes

Overlap extension PCR was employed to generate CAdV-2 E3-targeting transfer fragments encoding select E3 deletions and ~500 bases of 5' and 3' flanking sequence to facilitate targeted homologous recombination (HR) in BJ5183 *E. coli*. (See schematics, FIG. 4 and FIG. 5). As shown in FIGS. 5A and B in the "A" deletion (ΔE3A) all but the first 186 nucleotides of E3 ORF1 and the last 301 nucleotides of ORF2 were deleted, while for the E3 "B" deletion (ΔE3B) 186 nucleotides of E3 ORF1 and 83 nucleotides of ORF2 remain (See SEQ ID NO:1 and SEQ ID NO:2 for 5' and 3' flanks).

Both infectious clones harboring the ΔE3A and ΔE3B deletions were successfully rescued from transfected MDCK and E1B-MDCK cells, indicating that the specific E3 deletions support viral rescue. Because the ΔE3B configuration encompasses a larger E3-deletion, it became the design of choice for the generation of transgene expression cassette-carrying rCAdV-2 moving forward. This larger deletion indicates that practically all of the E3 region, e.g., about 82% of the E3 region can be deleted without adversely impacting viral rescue.

Example 5

Construction of E3 Deletion/Insertion Expression Cassettes with CMV Promoters Generation of HCMV-IE and CMV5 Promoters:

Amplification of the 3' end of the human cytomegalovirus immediate early promoter (hCMV-IE)(SEQ ID NO:3) was performed by PCR as previously described, using the primers pair hCMV-IE 5'F (SEQ. ID NO:5) (5'-TTATTAATAG-TAATCAATTACGGGG-3')/hCMV-IE 3' R (SEQ. ID NO:6) (5'-GCCACCGTACACGCCTACCGCCC-3') and BAC DNA EHV-gG (10 ng) as template. The resulting DNA fragment was subsequently cloned into the pCR™BluntII TOPO® vector (ThermoFisher Scientific) and excised by digestion with restriction enzymes Kpn-1 and BamH-1 and further cloned into a pUC18-based plasmid shuttle vector for further manipulation and construction of the CAdV transfer plasmids. The human CMV5 promoter (SEQ ID NO:4) was synthesized using GENSCRIPT® gene synthesis products with 5'-3' Spe-1 and BamH-1 restriction sites, respectively and cloned into the pUC57 *E. coli* shuttle vector for further manipulation and construction of the CAdV transfer plasmids.

Comparison of CMVIE and CMV5 Promoter Activity:

Reports in the literature have shown more robust protein expression from mammalian transgene expression cassettes driven by the CMV5 versus CMVie promoters. The CMV5 promoter differs from the CMVie promoter in that it contains, downstream of the CMVie transcription start site, ~560 bp of DNA encoding a human adenovirus type 5 (HuAd5) adenovirus tripartite leader with the adenovirus major late enhancer bracketed by splice donor and acceptor sites (Massie et al., 1995, Improved adenovirus vector provides herpes simplex virus ribonucleotide reductase R1 and R2 subunits very efficiently. Nature Biotechnology 13:602-608). The use of the CMV5 promoter was shown to substantially increase protein expression in 293 cells (Massie et al., 1998, Inducible overexpression of a toxic protein by an adenovirus vector with a tetracycline-regulatable expression cassette. Journal of Virology 72 (3):2289-2296).

Figure 7:
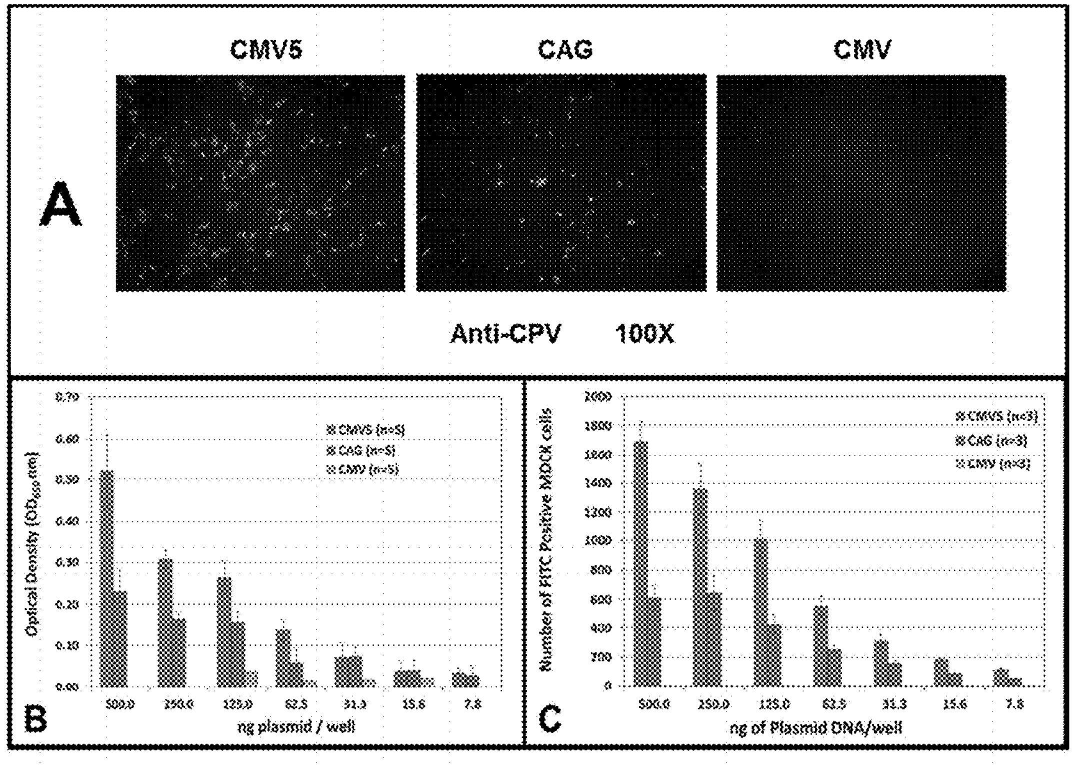
FIG. 7. An analysis of promoter strength by quantification of CPV VP2 expression by transient expression from the expression constructs as detected by IFA in transfected MDCK cells was performed. Panel A: CPV IFA of MDCK cells transfected with CPV VP2 expression plasmids driven by the CMVie or CMV5 promoters is shown. Panel B: Histogram of CPV VP2 ELISA of MDCK cells transfected with CPV VP2 expression plasmids driven by the CMVie, CAG, or CMV5 promoters as indicated. Panel C: Histogram of Molecular Devices ImageXpress MicroXL quantification of CPV VP2-positive MDCK cells transfected with CPV VP2 expression plasmids driven by the CMVie or CMV5 promoters as indicated.

Consistent with these reports, direct comparisons of protein expression from cassettes driven by either CMVie or CMV5 by transient transfection of expression plasmids containing CPV VP2, demonstrate more robust protein expression from mammalian transgene expression cassettes driven by the CMV5 versus CMVie promoters. As shown in FIG. 7., an analysis of promoter strength by quantification of CPV VP2 expression by transient expression from the expression constructs as detected by IFA in transfected MDCK cells was performed. In Panel A: CPV IFA of MDCK cells transfected with CPV VP2 expression plasmids driven by the CMVie or CMV5 promoters is shown. Panel B: is a histogram of CPV VP2 ELISA of MDCK cells transfected with CPV VP2 expression plasmids driven by the CMVie, or CMV5 promoters. Panel C: is a histogram of Molecular Devices ImageXpress MicroXL quantification of CPV VP2-positive MDCK cells transfected with CPV VP2 expression plasmids driven by the CMVie or CMV5 promoters as indicated. The results indicate that the CMV5 promoter can direct robust expression of the transgene, and expression from the CMV5 is greater in terms of both optical density IFA and the relative number of FITC positive MDCK cells than the CMVie promoter. Thus the CMV5 promoter was chosen to drive transcription of the CAdV-2 expression cassettes. However, none of the rCAdV-2 infectious clones containing the CMV5 promoter have led to rescue of rCAdV-2.

As shown in Table 2, while the CMV5 drove robust transient expression of the VP2 transgene, none of the rCAdV-2 infectious clones containing the CMV5 promoter have led to the rescue of rCAdV-2.

To directly address whether the CMV5 promoter sequence might be interfering with rCAdV-2 rescue, a DNA fragment containing the CMV5 promoter, a multiple cloning site (MCS) and the simian virus 40 (SV40) polyadenylation (polyA) sequence was integrated into the E3 region of the CAdV-2 genome. All of the components of the DNA cloned into AE3B, except for the ~560 bp of DNA that distinguishes the CMV5 from the CMVie (and the MCS,) are part of previously rescued rCAdV-2 viruses. Attempts at rescue were unsuccessful, strongly suggesting that the CMV5 promoter interferes with rescue of rCAdV-2. To support this conclusion, a reciprocal experiment was designed wherein homologous recombination was used to replace the CMV5 MCS SV40 polyA region in this infectious clone with a "rescuable" CMVie-based expression cassette.

Generation of rCAdV-2ΔE3B/CMVie EGFP, which Contains a CMV-IE-EGF Expression Cassette Expression Cassette Inserted into the ΔE3B Region of the CAdV2 Genome:

A rCAdV-2 carrying an Enhanced Green Fluorescent Protein (EGFP, Clontech) expression cassette (2.6 kb (SEQ ID NO.:7, CMVie EGFP) was generated to facilitate assessment of viral rescue and evaluate tropism in select cell lines and species in vivo. In brief, a CAdV-2 ΔE3B-targeting CMVie EGFP transfer fragment (CMVie-driven EGFP ORF followed by a SV40 polyadenylation sequence flanked by ~500 bp CAdV-2 DNA ending at position 183 of ORF1 (5') and beginning at position 82 of CAdV-2 E3 ORF2 (3')), was used for homologous recombination to generate rCAdV-2ΔE3B/CMVie EGFP. Successful HR events were evaluated by the detection of a DNA species of ~35 kb. PCR colony screens were performed to identify clones containing the transgene expression cassette (Forward P SEQ ID NO.:8; Reverse P SEQ ID NO.9). Positive clones were visualized by agarose gel electrophoresis wherein a positive clone had ~0.7 kb PCR product corresponding to the EFG transgene cassette. Additionally, proper transgene insertion and sequence was confirmed by sequence analysis using an ILLUMINA® MiSeq Sequencer, NextEr_XT library preparation methods, and NexGene software (Softgenetic; version 2.3) and SEQUENCER® software (Genecodes; version 5.1).

Successful Pme-1 digestion of the rCAdV-2GFP yielded two species: a ~32.7 kb (rCAdV-2 genome) and ~2.7 kb (PBR322 fragment). Transfection of MDCK and E1B-MDCK cells was achieved using LIPOFECTAMINE® 2000 transfection reagent (ThermoFisher Scientific). rCAdV-2ΔE3B/CMVie EGFP infectious clones were successfully rescued from transfected MDCK and E1B-MDCK cells, as indicated by GFP signal via fluorescence in transfected cells. Viruses were harvested from transfected cell supernatants/lysates and subjected to three successive freeze-thaw cycles (−70° C./37° C.), filter-sterilized, and them passed on both MDCK and E1B-MDCK. Infected cells were then observed for infection-dependent EGFF signal via fluorescent microscopy (data not shown).

The CMVIE EGFP SV40 polyA transgene expression cassette was successfully cloned into the ΔE3B domain of CAdV2. Recombinant virus was successfully rescued, and EGFP was detectable by fluorescent microscopic analysis post-infection.

Figure 8:
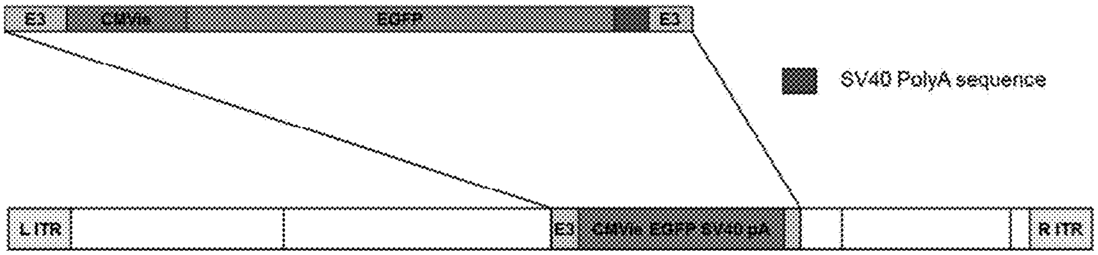
FIG. 8: Schematic of the CMVie EGFP SV40 polyA expression cassette in the CAV-2 MCS-1-5 backbone. Insertion is in the Δ E3B ORF2 where all but the first 186 nucleotides of E3 ORF1 and the last 82 nucleotides of are deleted. The EGFP gene is followed by a SV40 polyA signal. ITR=inverted terminal repeat.

Generation and Rescue of rCAdV-2 ΔE3B with an Enhanced Green Fluorescent Protein (EGFP) Expression Cassette from the rCAdV-2 ΔE3B Unrescuable Infectious Clone Carrying the CMV5 Promoter:

To support the conclusion that the CMV5 promoter inhibits rCAdV-2 rescue (see "Use of the CMV5 Promoter for transgene expression" section, above), a reciprocal experiment was conducted wherein homologous recombination was used to replace the CMV5 MCS SV40 polyA region in the MCS-1 infectious clone with a "rescuable" CMVie-based expression cassette. In brief, the CAdV-2 E3-targeting CMVie EGFP transgene transfer fragment above, was used for homologous recombination to generate a ΔE3B rCAdV-2 from infectious clone MCS-1-5 (MCS-1-5 contains the CMV5 Promoter, a small multiple cloning site (MCS) and a SV40 polyadenylation sequence). A purified ~2.6 Kb EGFP transfer fragment and linearized rCAV-2 infectious clone DNA derived from MCS-1-5, were co-transformed via electroporation into BJ5183 *E. coli* cells which were then selected on LB-agar plates with 50 □g/mL Carbenicillin. PCR colony screens were performed to identify clones containing the transgene expression cassette. Successful homologous recombination results in DNA species of ~35 Kb which, as supercoiled DNA, runs with or somewhat faster than the 23.1 Kb marker DNA species on a 0.7% agarose gel. Positive clones were visualized by agarose gel electrophoresis (FIG. 4). a schematic of the CMVie EGFP SV40 polyA expression cassette in the CAV-2 MCS-1-5 backbone the infectious clone DNA is illustrated in FIG. 8.

PmeI-digested of rCAV-2 MCS-1-5 EGFP virus was transfected into MDCK cells and E1B-MDCK cells using LIPOFECTAMINE® 2000 CD and 3000. rCAdV-2ΔE3B/CMVie EGFP infectious clones derived from the rCAdV-2 MCS-1-5 infectious clone DNA successfully facilitated the rescue of rCAdV-2 from transfected E1B-MDCK cells, as indicated by GFP signal via fluorescence in transfected cells (data not shown). As postulated in Appendix VI (Background), rescue of rCAdV-2 carrying the EGFP expression cassette derived from the CAdV-2 MCS-1 backbone further supports the conclusion that inhibition of rCAdV-2 rescue is CMV5-dependent, and more so is localized to the 560 bp huAd5 DNA sequence in CMV5.

Figure 9:
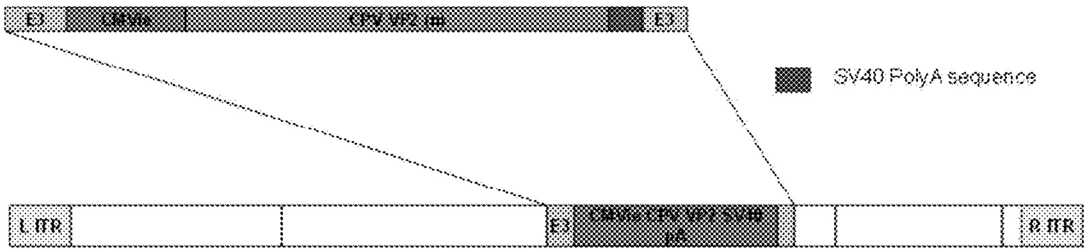
FIG. 9: Schematic of the CMVie CPV VP2 (n) SV40 polyA expression cassette in the CAV-2 backbone. Insertion is in the Δ E3B ORF2 where all but the first 186 nucleotides of E3 ORF1 and the last 82 nucleotides of are deleted. The VP2 (n) gene is followed by a SV40 poly A signal.

Generation of rCAdV-2ΔE3B/CMVie CPV VP2 (Native), which Contains a CMV-IE-VP2 Expression Cassette Expression Cassette Inserted into the ΔE3B Region of the CAdV2 Genome:

A rCAdV-2 carrying the canine parvovirus (CPV) VP2 gene was generated. In brief, similar to the above, a CAdV-2 ΔE3-targeting transfer fragment containing a CMVie-driven CPV VP2 ORF (SEQ ID NO.:10) was used for homologous recombination to generate a ΔE3B rCAdV-2 containing the VP2 expression cassette (See FIG. 9). Clones containing the successful transgene integration were detected by PCR screen, where a 1.7 kb PCR product was visualized by agarose gel electrophoresis. Proper transgene insertion and sequence was confirmed by sequence analysis using an ILLUMINA® MiSeq Sequencer, NextEr_XT library preparation methods, and NexGene software (Softgenetic; version 2.3) and SEQUENCER® software (Genecodes; version 5.1).

Figure 10:
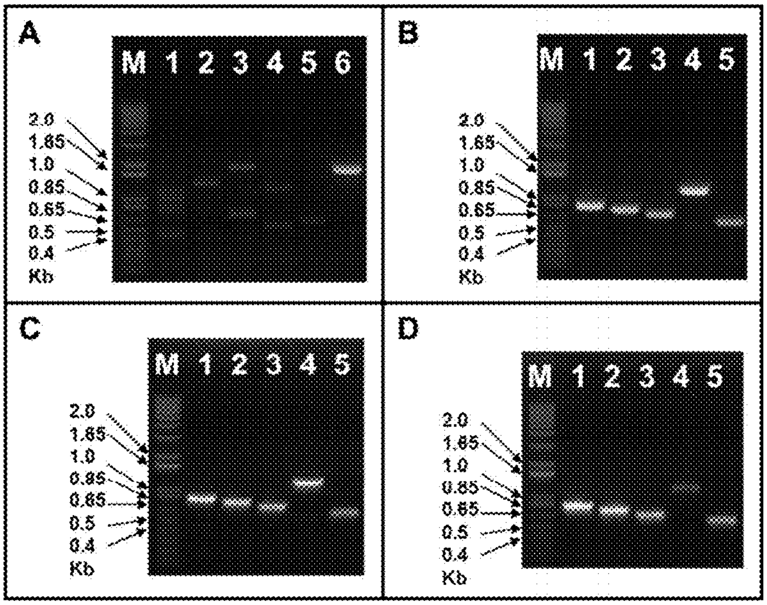
FIG. 10: PCR Analysis of rCAV-2 DNA purified from infected cells and supernatants. PCR was used to verify the presence of the CMVie CPV VP2 (n) transgene expression cassette in rCAV2ΔE3B/CMVie CPV VP2 from isolated viral DNAs. Panel A, pCAV-2 control virus; Panel B, clone #1; Panel C, clone #2. Panel D, control reactions with CMVie CPV VP2 (n) Transfer Plasmid. M is 1 Kb+ DNA ladder. Panel E. Expected Results of Transgene Expression Cassette-specific PCR Reactions. Reactions 1 and 2 utilize primers specific for CAV-2 H-A P VIII, the U-exon and CVP VP2; Reactions 3, 4 and 5 utilize primers specific for CPV VP2 (see Panel E). Reaction 7 (positive reaction for CAdV-2) uses the CAV-2-specific H-A P VIII and U-exon primers.

Successful Pme-1 digestion of the rCAdV-2GFP yielded two species: a ~32.7 kb (rCAdV-2 genome) and ~2.7 kb (PBR322 fragment). rCAdV-2ΔE3B/CMVie CPV VP2 infectious clones were successfully rescued from transfected MDCK and E1B-MDCK cells, as detected by CAdV-2 IFAs (data not shown). While CPV VP2 protein expression in infected cells was unsuccessful as detected by the lack of immunofluorescence antibody staining against the VP2 protein, the presence of the transgene expression cassette was detected in purified viral genomes by PCR PCR analysis of rCAV-2 DNA purified from infected cells and supernatants was used to verify the presence of the CMVie CPV VP2 (n) transgene expression cassette in rCAV2ΔE3B/CMVie CPV VP2 clones (FIG. 10). Panel A, pCAV-2 control virus; Panel B, clone #1; Panel C, clone #2. Panel D, control reactions with CMVie CPV VP2 (n) Transfer Plasmid. M is 1 Kb+ DNA ladder. Panel E. Expected Results of Transgene Expression Cassette-specific PCR Reactions. Reactions 1 and 2 utilize primers specific for CAV-2 H-A P VIII, the U-exon (SEQ ID NO.:11, SEQ ID NO.:12). and CVP VP2 (SEQ ID NO.:13, SEQ ID NO.:14); Reactions 3, 4 and 5 utilize primers specific for CPV VP2 (see Panel E) (SEQ ID NOs.:15-20). Reaction 7 (positive reaction for CAdV-2) uses the CAV-2-specific H-A P VIII and U-exon primers (SEQ ID NO.:21, SEQ ID NO.:22).

Therefore, while CMVIE CPV VP2 (n) SV40 polyA transgene expression cassette was successfully cloned into the ΔE3B domain of CAdV2, recombinant virus successfully rescued, and the presence of the VP2 sequence was confirmed, VP2 protein expression was not detectable.

Generation of rCAdV-2ΔE3B/CMVie CPV VP2 (Codon-Optimized), which Contains a CMV-IE-VP2 Expression Cassette Inserted into the ΔE3B Region of the CAdV2 Genome:

A CAdV-2 E3-targeting CMVie CPV VP2 codon optimized (co) transgene transfer fragment (CMVie-driven CPV VP2 ORF (co) followed by a Bovine growth hormone (BGH) polyadenylation sequence flanked by ~500 bp CAdV-2 DNA ending at position 183 of ORF1 (5') and beginning at position 82 of CAdV-2 E3 ORF2 (3')) (SEQ. ID NO.:23), was generated by overlap extension PCR and cloned into a TOPO vector for archiving and amplification. The construct was used for homologous recombination to generate a ΔE3B rCAdV-2.

Clones containing the successful transgene integration were detected by PCR screen, where a 2.3 kb PCR product was visualized by agarose gel electrophoresis. Proper transgene insertion and sequence was confirmed by sequence analysis using an ILLUMINA® MiSeq Sequencer, NextEr_XT library preparation methods, and NexGene software (Softgenetic; version 2.3) and SEQUENCER® software (Genecodes; version 5.1).

rCAdV-2ΔE3B/CMVie CPV VP2 (co) infectious clones were successfully rescued from transfected MDCK and E1B-MDCK cells, demonstrated by CAdV-2 IFA performed on P1-infected cells using anti-CAdV-2 antibodies directly conjugated to fluorescein isothiocyanate (FITC) (data not shown). To verify that rescued virus encodes the CMVie CPV VP2 (co) transgene expression cassette, P2 virus rCAdV-2 and P5 CAdV-2 genomes were purified. PCR analysis of extracted DNAs using primers specific for regions of the CAdV-2 genome (hexon-associated protein VIII (H-A P VIII) and the U-exon), the CMVie promoter and CPV VP2 were employed. (data not shown) The PCR analysis yielded the correct size PCR products indicating that purified P2 viral genomes encoded the CMVie CPV VP2 (co) transgene expression cassette.

Flow cytometic analysis of CMVie CPV VP2 (co) rCAdV infected cells using antibodies against CAdV2 and CPV VP2 was employed to verify expression of infected MDCK cells. Briefly, suspension MDCK cells were infected with rCAdV-2 and control rCAdV-2 in a 12-well format and cultured for 72 h (37° C., 5.0% $CO_2$ at 125 rpm in a humidified incubator). Cells were then collected, washed with PBS and then, using a CYTOFIX/CYTOPERM™ Fixation/Permeabilization Kit (BD Biosciences, Cat. #554714), treated with the CYTOFIX™ fixation solution followed by two CYTOPERM™ permeabilization solution washes. Cells were then incubated with FITC-conjugated anti-CAdV-2 or anti-CPV VP2 antibodies (Anti-CAV2 antibody: VMRD, Catalog #CJ-F-CAV-50X and Anti-CPV VP2 antibody: VMRD, Catalog #CJ-F-CPV 50X, respectively), washed 2× with CYTOPERM™ and analyzed by flow cytometry using a BD Biosciences FACSCANTO™ Flow Cytometry System.

Figure 11:
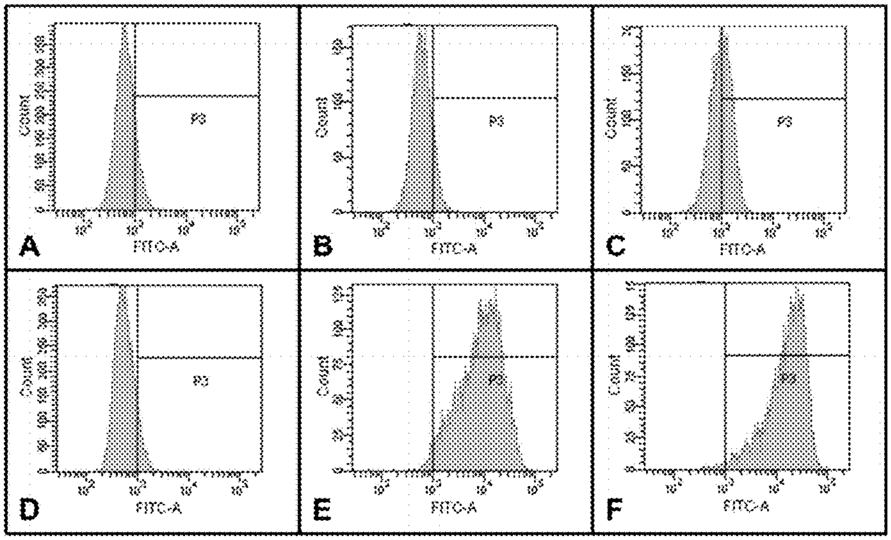
FIG. 11. Flow Cytometric Analysis of rCAV-2-infected MDCK cells. Panels A-F are histograms of signal present in single cells. Suspension MDCK cells were infected with rCAV-2 control virus carrying the BRSV F (co) (Panels B and E) or infected with rCAV-2 carrying the CPV VP2 (co) (Panels C and F) expression cassettes and stained 72 h post-infection with either FITC-conjugated anti-CPV VP2 (Panels A, B and C) or FITC-conjugated anti-CAV2 (Panels D, E and F) antibodies. Panel G is a summary and quantification of the results shown in Panels A-F.
Figure 12:
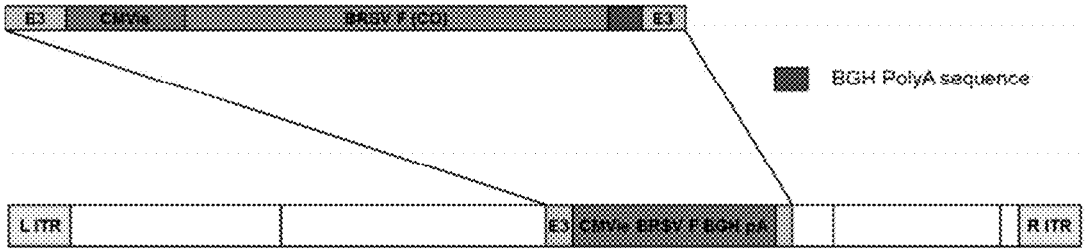
FIG. 12. Schematic of the CMVie BRSV F (co) BGH polyA expression cassette in the CAdV-2 backbone. The BRSV F (co) gene is followed by a BGH poly A signal.

FIG. 11 shows the results from the flow cytometric analysis of CMVie CPV VP2 (co) rCAdV infected MDCK cells. Panels A-F are histograms of signal present in single cells. Suspension MDCK cells were infected with rCAdV-2 control virus carrying the BRSV F (co) (Panels B and E) or infected with rCAV-2 carrying the CPV VP2 (co) (Panels C and F) expression cassettes and stained 72 h post-infection with either FITC-conjugated anti-CPV VP2 (Panels A, B and C) or FITC-conjugated anti-CAV2 (Panels D, E and F) antibodies. Panel G is a summary and quantification of the results seen in FIG. 11. The results of staining with anti-CAV-2 shows that most of the rCAV2-BRSV F (co)- or rCAV2-CPV VP2 (co)-infected (FIG. 1, Panels E and F, respectively) MDCK cells express CAdV2 proteins, while uninfected cells (FIG. 1, Panel D) are effectively negative for CAdV-2. Staining with anti-CPV VP2 antibodies (FIG. 1, Panels A, B and C) shows that only rCAV2-CPV VP2 infected MDCK cells (Panel C) express CPV VP2 proteins, although some background signal is observed in uninfected and rCAV2-BRSV F-infected cells with the anti-CPV VP2 antibodies (Panels A and B, respectively).

Thus, the CMVie CPV VP2 codon optimized (co) transgene expression cassette was successfully cloned into the ΔE3B domain of CAdV2. Recombinant virus was rescued from transfected MDCK cells, and the transgene expression cassette was detected in purified viral genomes. CPV VP2 mRNA was detected in infected cells (data not shown), and protein expression of CPV VP2 in infected cells was confirmed by flow cytometric analysis, in contrast to the native VP2 expression cassette.

Generation of rCAdV-2 ΔE3B with a Codon-Optimized Bovine Respiratory Syncytial Virus Fusion Protein Expression Cassette Inserted into the ΔE3B Region of the CAdV2 Genome:

In brief, a CAdV-2 E3-targeting transfer fragment containing a CMVie-driven CPV Bovine respiratory syncytial virus (BRSV) Fusion (F) protein ORF followed by a BGH polyadenylation sequence flanked by ~500 bp CAdV-2 DNA ending at position 183 of ORF1 (5') and beginning at position 82 of CAdV-2 E3 ORF2 (3') was used for homologous recombination to generate a ΔE3B rCAdV-2. (SEQ ID NO.:27). Both the native (n) and codon optimized (co) versions of the BRSV F gene were cloned into CAdV-2 vector background, and virus carrying both of versions of the transgene where successfully rescued. However, only the BRSV F (co) gene was used for downstream applications.

rCAdV-2ΔE3B/CMVie BRSV F (CO) infectious clones were successfully rescued from MDCK cells, as indicated by CPE of cells infected with viral supernatants/cell lysates. The presence of the transgene expression cassette was detected in purified viral genomes. DNA was extracted from P3 rCAV2-BRSV F (co) virus and used as a template for PCR analysis to detect the presence of the BRSV F (co) gene in the virus genome. The transgene was sequenced to confirm the gene sequence.

Figure 14:
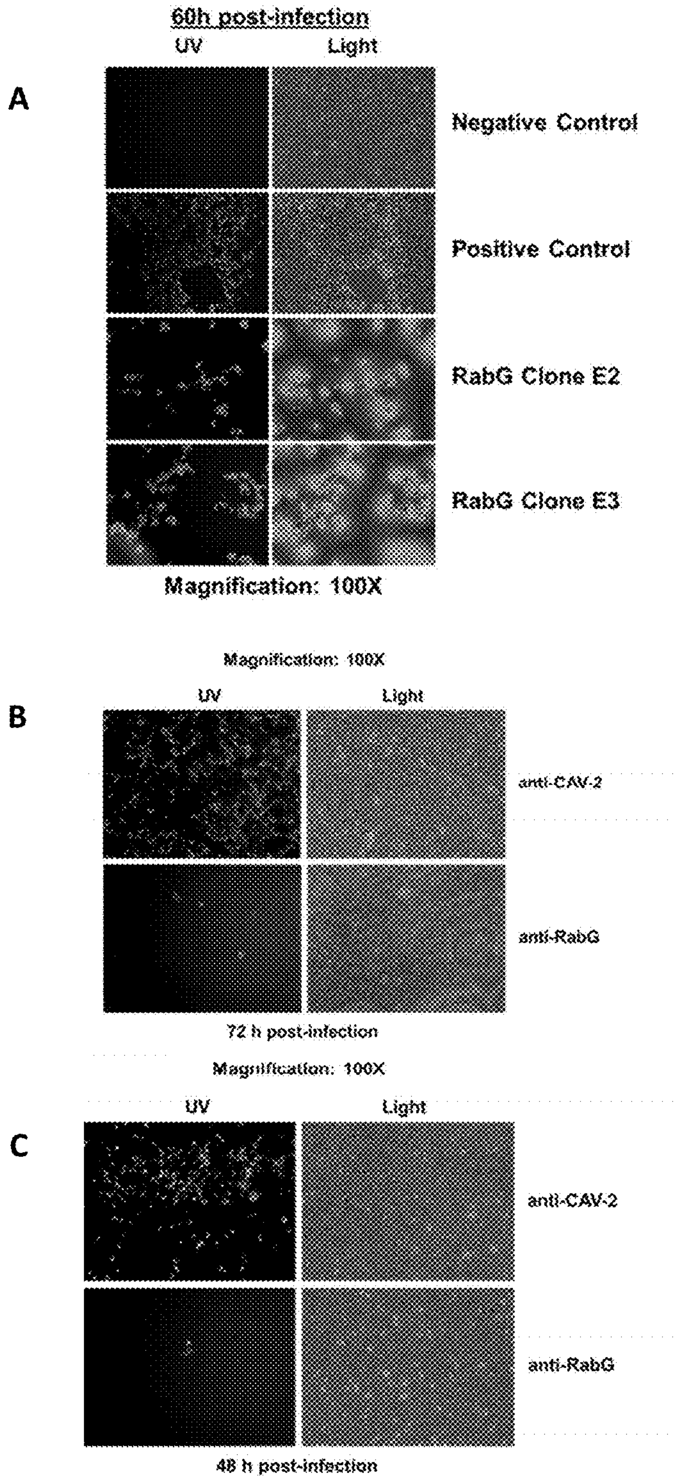
FIG. 14. CAdV-2-specific IFA of rCAV-2 RabGP P2 virus infected E1B-MDCK cells. CAdV-2 IFAs of infected E1B-MDCK cells were performed 60 h post-infection cells using anti-CAdV-2 antibodies directly conjugated to fluorescein isothiocyanate (FITC) and mouse anti-RabG monoclonal and FITC-conjugated goat anti-mouse antibodies.

Expression of BRSV F by infected cells was confirmed by flow cytometric analysis (See FIG. 11).

indicated by CAdV-2 IFAs as shown in FIG. 14, a CAdV-2 IFA of rCAV-2 RabGP P2 virus-infected EIB-MDCK cells using anti-CAdV-2 antibodies directly conjugated to fluorescein isothiocyanate (FITC) confirms rCAdV-2 rescue both by anti-RabG and CAdV-2 immunofluorescence (Panels B and C, 48 and 72 hours post infection).

As indicated by fluorescent (CAV-2+ and RabG+) cells in FIG. 14, Panels B and C, E1B-MDCK cells infected with rCAV-2 RabGP E2 and E3 viruses do express rabies G. However, the number of RabG+ cells appears substantially less than CAdV-2+ cells.

TABLE 2

Summary of BIVI-generated rCAdV-2 infectious clones.

| | Transgene | Promoter | PolyA | Rescue | Protein Expression in infected cells | Transfer Construct |
|---|---|---|---|---|---|---|
| 1 | None: ΔE3A and B | N/A | N/A | Yes | NT | SEQ ID NOs.: 1, 2 |
| 2 | EGFP | CMVie | SV40 | Yes | Yes | SEQ ID NO.: 7 |
| 3 | CPV VP2 (n) | CMVie | SV40 | Yes | NT | SEQ ID NO.: 10 |
| 4 | CPV VP2 (n) | CMV5 | SV40 | No | NT | N/A |
| 5 | CPV VP2 (co) | CMVie | BGH | Yes | Yes | SEQ ID NO: 23 |
| 6 | CPV VP2 (co) | CMV5 | SV40 | No | NT | SEQ ID NO.: 7NA |
| 7 | BRSV F | CMVie | BGH | Yes | Yes | SEQ ID NO: 27 |
| 8 | EGFP in MCS1 | CMVie | SV40 | Yes | Yes | N/A |
| 11 | Rabies G (n) | CMVie | BGH | Yes | Yes | SEQ ID NO: 25 |
| 12 | Rabies G (co) | CMVie | SV40 | No | NT | Data not shown |
| 13 | Rabies G (co) | CMV5 | SV40 | No | NT | N/A |

Figure 13:
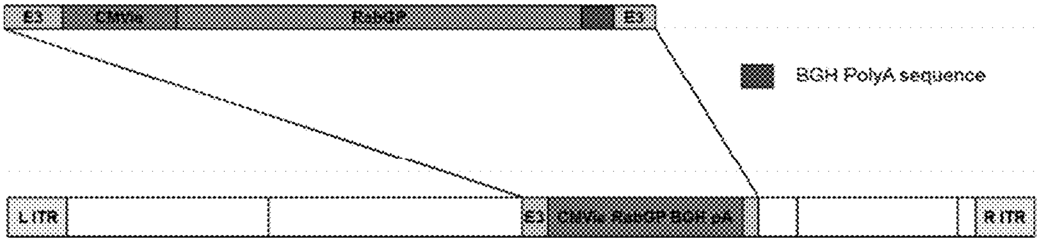
FIG. 13. Schematic of the CMVie RabGP BGH polyA expression cassette in the CAdV-2 backbone. The RabGP gene is followed by a BGH poly A signal.

N/A = Not applicable.
NT = Not tested.
* = Expression seen with transfection only Generation of rCAdV-2 ΔE3B with a Rabies Glycoprotein (n) Expression Cassette Inserted into the ΔE3B Region of the CAdV2 Genome:

In brief, a CAdV-2 E3-targeting Transfer Fragment containing a CMVie-driven Pasteur Strain Rabies glycoprotein (RabGP) ORF followed by a BGH polyadenylation sequence flanked by ~500 bp CAdV-2 DNA ending at position 183 of ORF1 (5') and beginning at position 82 of CAdV-2 E3 ORF2 (3') was used for homologous recombination to generate a ΔE3B rCAdV-2. (SEQ ID NO.:25)(See FIG. 13) The native Pasteur Rabies G gene was PCR-amplified from a Raccoonpox-based rabies vaccine (rRCNV-Rabies G2 Vaccine), Lot #D015-054-). Expected size of amplified RabGP DNA is ~1.6 Kb.

The RabGP fragment was then ligated into the pUC18-B-Bflb-CO fragment and transformed into TOP10 *E. coli*. PCR colony screen for RabGP DNA was performed using RabGP-specific primers (data not shown).

DNAs were digested with PmeI to liberate the transfer fragments (~3.45 Kb) and ScaI to cut the vector backbone to facilitate identification of the transfer fragments. Purified ~3.45 Kb PmeI CMVie RabGP (n) Transgene (expression cassette) transfer fragments and linearized rCAV-2 infectious clone DNAs were co-transformed via electroporation into BJ5183 *E. coli* cells which were then selected on LB-agar plates with 50 μg/mL Ampicillin. PCR colony screens were performed to identify clones containing the transgene expression cassette and visualized by agarose gel electrophoresis (data not shown).

PmeI-digested HR clone DNAs were transfected into E1B-MDCK cells using LIPOFECTAMINE® 2000 CD. rCAdV-2ΔE3B/CMVie RabGP infectious clones were successfully rescued from transfected E1B-MDCK cells, as As summarized in Table 2, many ΔE3B-based infectious clones have been generated that did not facilitate the rescue of rCAdV-2 from transfected MDCK or E1B-MDCK cells. These include CPV VP2, and Rabies G containing transgene expression cassettes driven by the CMV5 promoter, clones containing the rabies glycoprotein G wherein the nucleotide sequence was codon optimized (76% identity to the SAD P5/88 strain, and clones containing the hMGFP (green) (Promega) and MCherry (red) (Clontech) fluorescent protein reporter constructs (data not shown).

This variability as compared between comparably sized inserts is not simply a reflection of codon optimization, as both native and codon optimized sequences facilitated the rescue of rCAdV-2 carrying BRSV F and CPV VP2 (see above, Table 2). Indeed, rCAdV-2 infectious clones carrying native hMGFP and MCherry ORFs also did not facilitate rCAdV-2 rescue (data not shown). Taken together, the data suggested that the use of CMV promoters in the context of the CAdV-2 vector platform is unpredictable and that the choice of promoter is a significant consideration in the construction of the expression cassette because it can significantly impact the rescue of rCAdV-2 clones.

Example 6

Expression Cassettes with EHV4 Promoters

Identification and Construction of New Equine Derived Promoters:

Novel heterologous equine promoters from the equine herpesvirus type 4 (EHV4) were identified and isolated. Two promoters were of interest; (1) the 600 bp EHV-4 gG promoter (4pgG600)(SEQ ID NO.:29) at ORF70 encoding glycoprotein G (gG); and (2) the 600 base pair EHV-4 MCP promoter (4pMCP600) (SEQ ID NO.:30) at ORF42 encoding the major capsid protein (MCP). The glycoprotein G gene (orf70) is active during early and late times in the replication cycle (Colle et al. 1995, Drummer et al. 1998). The major capsid protein is one of the most abundant constituents of the virion and needed for assembly of capsids in the cell nucleus as soon as newly synthesized viral DNA is ready for packaging. Its promoter is therefore expected to be active during early and late times in the viral replication cycle. Sensitive to the size limitation of the CAdV backbone, both EHV-4 promoter sequences were truncated to approximately 75% of their original lengths. In particular the 600 bp 4pgG600 promoter was truncated to 430 bp to generate the promoter fragment p430 (SEQ ID NO.:31), and the 600 bp 4pMCP600 promoter was truncated to 455 bp to generate the promoter fragment p455 (SEQ ID NO.:32).

The generation of virus like particles (VLPs) by rCAdV-2 vaccine virus infected cells can be a critical factor for canine adenovirus (CAdV-2) vaccine efficacy. While rCAdV-2 containing a CMVie-driven CPV VP2 expression cassette could be rescued, as detailed above, substantial VP2 expression (for VLP generation) in rCAdV-2 CMVie CPV VP2 infected cells could not be achieved using the conventional CMVie promoter. Additionally, rCAdV-2 VP2 virus containing the CMVS promoter could not be rescued. Therefore, it was of interest to use new promoters with the above identified characteristics capable of driving robust, stable, reproducible expression of antigens of interest.

Generation BamHI of CAdV-2 Transfer Plasmids Containing EHV-4 P CPV VP2 (co): Generation of KpnI/EHV-4 P DNA:

EHV-4 promoters fragments gG430 and MCP455 were gradient PCR-amplified from using the following oligonucleotide pairs:

```
gG430 F:
                                   (SEQ ID NO.: 33)
TTTAAAGGTACCTCTATTTGAGGACCCGCCGAGTACC;

gG430 R:
                                   (SEQ ID NO.: 34)
AAATTTGGATCCAACTGCAGCTTATCACAGCTTTACAGGTGG

MCP455 F:
                                   (SEQ ID NO.: 35)
TTTAAAGGTACCACTGGTGGTAGCATATACTACCTTTATTTATACGC;

MCP455 R:
                                   (SEQ ID NO.: 36)
AAATTTGGATCCGATCCTATGGTAGCGGTAAAACACCG,,
```

respectively.

Expected sizes of amplified gG430 and MCP455 DNAs are 454 and 479 bp, respectively.

Previously prepared CAdV-2 transfer plasmids used for the successful integration at the ΔE3B and rescue of rCAV-2 (as detailed above) were used as the basis of the EHV-4 promoter containing CPV VP2 transfer plasmid by a BamHI/KpnI-based exchange of the CMVie promoter with the EHV-4 promoters.

Two different codon-optimized CPV VP2 sequences, designated "Despliced" (SEQ ID NO.:37) and "Gen0.95" (SEQ ID NO.:38) were used to prepare CAdV-2 transfer plasmids containing expression cassettes driven by the CMVie. Gen0.95 is a codon-optimized CPV VP2 sequence obtained from Genscript with a Codon Adaptation Index (CAI) 0.95. Analysis of Gen0.95 with a splice site finder algorithm (2013/2014 © Human Splicing Finder—Designed by Ghadi Raï; Inserm UMR_S910—Aix Marseille Université, 27 Boulevard Jean Moulin, 13385 Marseille Cedex 05) suggested the presence of 43 potential Splice Donor sites. 89 nucleotide changes (5.07% sequence change versus Gen0.95) were made to eliminate 40 splice donor sites that did not alter the amino acid sequence or generate least-favorable codons based on the canine species.

Purified ~3.5 Kb PmeI EHV-4 P CPV VP2 (co) transfer fragments, containing the two VP2 sequences above, and linearized rCAV-2 infectious clone DNA were co-transformed via electroporation into BJ5183 *E. coli* cells for homologous recombination. Intact clones were selected on LB-agar plates with 50 μg/mL Ampicillin. Clones with the proper integration size and orientation were identified by PCR screen, selected, and expanded.

Successful PmeI-digestion of the pCAV-2 infectious clones yield DNA species of ~33.5 (pCAV-2 genome) and ~2.7 (pBR322 fragment) Kb. PmeI-digested infectious clones were transfected into E1B-MDCK and MDCK cells using LIPOFECTAMINE® 3000. Passage 1 (P1) through passage 7 (P7) viruses, designated pCAV2ΔE3B/pgG430-VP2 (Despliced) (SEQ ID NO.:39), pCAV2ΔE3B/gG430-VP2 (Gen 0.95) (SEQ ID NO.:40) or pCAV2ΔE3B/p455-VP2 (Gen0.95) (SEQ ID NO.:41), were harvested from transfected cell supernatants/lysates subjected to three successive freeze-thaw cycles (−70° C./37° C.), filter-sterilized, and then passed on E1B-MDCK cells.

AI-ST cells were infected with select rCAdV-2 for immunofluorescence assays (IFAs) for CAdV-2 and CPV VP2 protein expression. 72 h post-infection, cells were fixed with CYTOFIX/CYTOPERM™ Fixation/Permeabilization Kit (BD Biosciences, Cat. #554714), treated with the CYTOFIX™ fixation solution followed by two CYTOPERM™ permeabilization solution washes. Cells were then incubated with FITC-conjugated anti-CAdV-2 or anti-CPV VP2 antibodies (Anti-CAdV2 antibody (mAb): VMRD, Catalog #CJ-F-CAV-50X and Anti-CPV VP2 antibody: VMRD, Catalog #CJ-F-CPV 50X, respectively), washed 2× with CYTOPERM™ and analyzed by flow cytometry using a BD Biosciences FACSCANTO™ Flow Cytometry System.

CAdV-2 and CPV VP2 proteins are readily visualized by IFA and detected by FC in a substantial proportion of AI-ST 2015 cells infected with rCAdV-2 carrying two different nucleotide variants of CPV VP2 (Despl and Gen0.95, at 48 and 72 h post-infection). Substantial CPV VP2 protein was identified in tissue culture supernatants/lysates (after freeze/thaw) by Dot Blot (and very likely reflects the presence of assembled VLPs).

The results in FIG. 19 show that CAV-2 and CPV VP2 proteins are readily visualized by IFA of infected AI-ST cells (but not in cells infected with rCAdV-2 encoding the non-relevant BRSV transgene), indicating robust CPV VP2 expression from both Despliced and Gen0.95 CPV VP2 (co) sequence variants driven by both gG430 and MCP455 EHV-4 promoters (see FIG. 19A). CPV VP2 expression was detected in less than 3% of the cells infected with original rCAdV-2 CMVie CPV VP2 (see FIG. 15) indicating rCAdV-2 carrying CPV VP2 expression cassettes driven by the new EHV4 derived promoters p430 and p455 could be successfully rescued. Surprisingly, CPV VP2 expression driven by the gG430 and MCP455 EHV-4 promoters was detected in 14% to 36% of the infected cells (see FIG. 16), as compared to the CAdV vectors where CMV5 promoter sequences were utilized at the ΔE3B location, in which case viral rescue was not successful.

Dot blot analysis was performed to analyze transgene expression in infected cells. Briefly, clarified (6000×g, 5 min) tissue culture supernatants/lysates (freeze/thaw) from infected AI ST (for rEHV-1) and E1B MDCK (for rCAdV-2) cells were serially diluted with PBS before addition to apparatus and adsorbed to PVDF via aspiration. Subsequent steps are a 30 minute exposure to 5.0% BioRad Blotting Grade Blocker in TBST, 1.0 h exposure to 1° antibodies, three TBST washes, and a 1.0 h exposure to peroxidase-conjugated 2° antibodies (anti-mouse and anti-swine, Jackson ImmunoResearch) and visualization via TMB. For quantification, dot blots were analyzed using ImageJ software (Burger, W., Burge, M. J. (Eds.), 2008. Digital Image Processing: An algorithmic introduction using Java. Springer-Verlag, New York). Image colors are inverted to subtract background and integrated density of each dot recorded. Values are assigned + and − designations as follows: "++++"=>800000, "+++"=500000 to 800000, "++"=300000 to 499999, "+"=120000 to 299999, "+/−"=80000 to 119999 and "−"=<80000.

Figure 17:
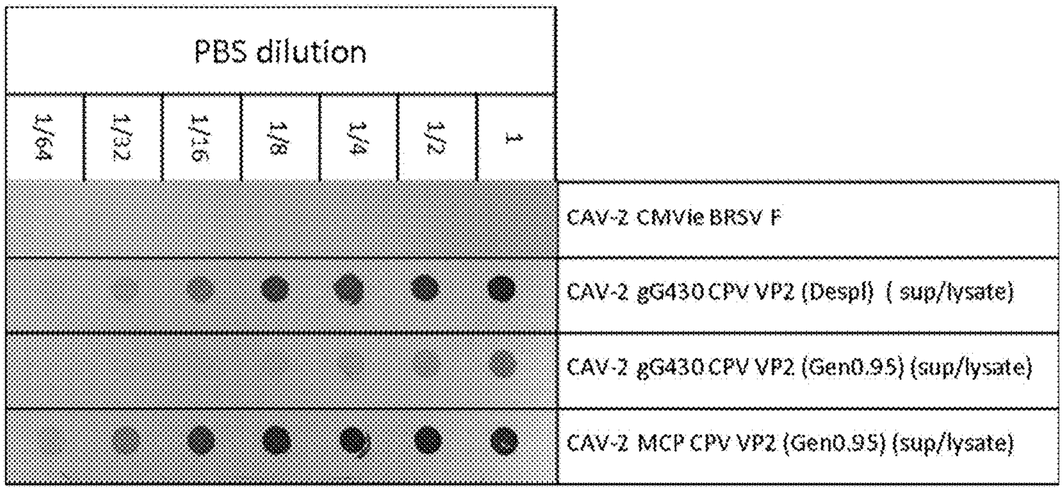
FIG. 17: rCAdV-2 with New EHV-4 Promoters: Dot Blot Analysis of CPV VP2 Protein Expression in Infected MDCK cells. 1°=1/50 a-CPV-FITC mAb (VMRD); 2°=1/1.000 Goat-a-mouse IgG-peroxidase (JIR). (A) Original dot blot data. (B) Semi-quantitative data generated from dot blot: For quantification, dot blots are analyzed using ImageJ software (Burger, W., Burge, M. J. (Eds.), 2008. Digital Image Processing: An algorithmic introduction using Java. Springer-Verlag, New York). Image colors are inverted to subtract background and integrated density of each dot recorded. Values are assigned + and − designations as follows: "++++"=>800000, "+++"=500000 to 800000, "++"=300000 to 499999, "+"=120000 to 299999, "+/−"=80000 to 119999 and "−"=<80000.

As seen in FIG. 17, strong CPV VP2 protein signal was observed in tissue culture supernatants/lysates from cells infected by rCAdV-2 encoding EHV-4 promoters-driven expression cassettes for CPV VP2, while signal was not detected in samples from cells infected with rCAdV-2 encoding a non-relevant expression cassette. These results show that substantial CPV VP2 protein was identified in tissue culture supernatants. These results very likely reflect the presence of assembled CPV VP2 VLPs. This is in contrast to the original rCAdV-2 CMVie CPV VP2 where dot blot analysis showed CMVie-driven CPV VP2 signal was at or below background levels—and at comparable with supernatants/lysates from the negative controls (CAdV-2, rCAdV-2 CMVie BRSV F-infected cells and cell culture supernatant/lysates from uninfected cells).

As shown in FIG. 17, the VP2 protein can be recognized in the supernatant and, therefore, is expected to be in the conformation required to be immunogenic. Importantly, as discussed above the rescue of recombinant CAdV-2 was not achieved in clones where the transgene was driven by CMV5 promoter sequences. Thus, the new EHV-4 derived promoter sequences of the present invention such as p430 and p455 not only facilitate transgene expression, but also support the crucial step of viral rescue.

Generation of CAdV-2 Transfer Plasmids Containing EHV-4 promoters CPV RabG (n):

A second CAdV-2 construct was generated using the new EHV-4 derived p455 promoter of the present invention. The rCAdV-2 RabG(n) was chosen because expression by infected cells was not observed using the conventional CMVie promoter.

The objective of this experiment was to confirm the activity of the new EHV-4 promoter in the context of rCAdV-2 with a second transgene, RabG (a membrane protein) by the measurement of EHV-4 promoter-driven RabG protein expression by rCAdV-2 p455 RabG (n)-infected AI-ST 2015 cells.

The RabG(n) sequence was isolated from rescued rCAV-2 CMVie RabG (n) (SEQ ID NO.:25) as discussed above. A 1596 bp RabG (n) sequence including a Kozak sequence immediately 5' to the ATG START codon was excised with BamHI and SalI (5' and 3', respectively) restriction endonucleases, and ligated into BamHI/SalI cut rCAdV transfer fragments with the gG430 promoter and MCP455 promoters which were then transformed into TOP10 *E. coli.*

Purified ~3.3 Kb PmeI EHV-4 P RabG (n) transfer fragments and linearized rCAV-2 infectious clone DNA were co-transformed via electroporation into BJ5183 *E. coli* cells for homologous recombination. Intact clones were selected on LB-agar plates with 50 μg/mL carbenicillin. PCR colony screens were performed to identify EHV-4 pG430/RabG (n) (SEQ ID NO.:42) and EHV-4 p455/RabG (n) (SEQ ID NO.:43) clones. Clones were screened with primers specific for RabG DNA and visualized via agarose gel electrophoresis. Expected DNAs are 1501 bp.

PmeI-digested infectious clones were transfected into E1B-MDCK and MDCK cells using LIPOFECTAMINE® 3000. Passage 1-7 (P1-P7) viruses, designated pCAV2ΔEB3/gG430 or MCP455 RabG (n), were harvested from transfected cell supernatants/lysates subjected to three successive freeze-thaw cycles (−70° C./37° C.), filter-sterilized, and then passed on E1B-MDCK cells.

IFA and flow cytometry were employed to assess EHV-4 promoter-driven expression of RabG in rCAdV-2-infected AI-ST 2015 cells. CAdV-2 protein expression was probed with anti-CAdV-2 FITC-conjugated porcine polyclonal antibodies (VMRD). RabG protein expression was probed with mouse monoclonal antibodies (Novus). CAdV-2 and RabG proteins are readily visualized by IFA and detected by FC in AI-ST 2015 cells infected with rCAdV-2 carrying RabG (n) (at 72 h post-infection).

The results in FIG. 18 indicate that CAV-2 and RabG proteins are readily detected in AI-ST 2015 cells infected by select rCAdV-2 and rEHV-1 by flow cytometric analysis. These results demonstrate substantial expression of RabG driven by the MCP455 EHV-4 promoter. In contrast, while RabG is readily detected in cells infected with rCAdV-2 p455 RabG (see FIGS. 19B and C), expression is detected in <2.0% of cells infected with original rCAdV-2 CMVie RabG (see FIG. 18).

In conclusion, the gG430 and MCP455 RabG (n) SV40 polyA transgene expression cassettes were successfully cloned into the ΔE3B domain of CAdV-2. Recombinant virus was rescued from transfected E1B-MDCK cells as indicated by CPE in virus infected cells. MCP455 promoter-driven expression of RabG transgene by rCAdV-2 in infected AI-ST 2015 and BIVI 2011 MDCK cells was confirmed by IFA and Flow Cytometry.

Example 7

Preparation of Pharmaceutical Compositions (Vaccines) Comprising rCAdV-CMV/CPV VP2

Canine parvovirus (CPV) is a highly contagious virus that can cause high morbidity and mortality depending on virulence, host, and environmental factors. The use of an effective vaccine program for dogs utilizing MLV and killed virus vaccines over the last 30 years has greatly decreased the mortality rate. CPV is a non-enveloped single-stranded DNA virus with two structural proteins (VP1 and VP2) forming the capsid. VP2 is known to be involved with virus pathogenicity and host immune response, and is therefore our target of choice for incorporation and expression in the recombinant CAdV2 system.

The objective of this study was to perform a preliminary evaluation of efficacy of an experimental rCAV2-CPV VP2 vaccine as compared to a MLV combination vaccine. The MLV combination contained canine adenovirus type 2 (CAV2), canine distemper virus (CDV), and canine parvovirus (CPV) blended at a level between the established minimum immunizing dose and the release dose of each fraction as established in current products for each particular antigen.

In this study, rCAV2-CPV VP2 was administered in a two-dose regimen, three weeks apart, to 6-7 week old puppies, in order to determine if the CAdV-CPV VP2 vector vaccine provided protection against CPV challenge. Currently, as MLV vaccines are the gold standard for protection against CPV and ICH, the test group was compared to a group of 6-7 week old puppies administered a two-dose regimen, three weeks apart, of a MLV vaccine combo containing CPV, CDV, and CAdV2. This group was considered the positive control group. A third group was administered a two-dose regimen, 3 weeks apart, of PBS as the challenge controls. Dogs were challenged with CPV-2b approximately three weeks post-second vaccination in order to evaluate efficacy.

Test vaccines were administered to twelve (12) healthy, CAV2- and CPV-sero-negative canines 6 weeks 2 days to 7 weeks 2 days of age, as a 1 ml subcutaneous dose, given in a 2-dose regimen, 3 weeks apart. The twelve (12) animals were split into 2 test groups as follows: Group 1—rCAV2-CPV VP2 @ 8.0 logs/ml; Group 2—MLV Combination (CAV2, CDV, CPV).

Phosphate Buffered Saline (PBS) was administered to a group of six (6) healthy, CAV2- and CPV-sero-negative canines 6 weeks 2 days to 7 weeks 2 days of age, as a 1 ml subcutaneous dose, given in a 2-dose regimen, 3 weeks apart. This group was deemed as Group 3, and served as challenge controls for the study. All animals in Groups 1-3 were challenged oro-nasally with virulent CPV-2b on 22 DPV2. Clinical case data post-challenge (clinical signs, pyrexia, lymphopenia, leukopenia and detection of CPV in feces) was analyzed.

Vaccine Formulation:

rCAV2-CPV VP2 tissue culture stock was diluted with 0.01M PBS to the target dose noted below. No adjuvants were used. The MLV positive control was formulated and lyophilized with a SGGK stabilizer where each of the antigens in the combo was higher than the minimum immunizing dose for the SOLOJEC® product line. Targeted dosages for the vaccines were as follows:

TABLE 3

| Group | Vaccine | Targeted Dosage ($Log_{10}FAID_{50}$/ml) |
|---|---|---|
| 1 | rCAdV2-CPV VP2 | ~8.0 |
| 2 | MLV (CAV2, CDV, CPV) | CAdV2 - ~3.8-5.0<br>CDV - ~1.6-3.0<br>CPV - ~3.6-4.8 |
| 3 | PBS or MEM | NA |

Challenge Material:

On the day of challenge, three vials of the frozen CPV-2b challenge material, were quick-thawed by manually agitating the vial(s) in a 36±2° C. water bath. The material was then diluted 1:10 in cell culture medium to the desired concentration. The challenge inoculum remained on ice at all times during the preparation and challenge procedures.

Vaccine Antigen Titration: CAV2-CPV VP2

Briefly, ten-fold serial dilutions of the vaccine were made. Each dilution was added to each of 5 wells at 100 microliters per well in 96 well plates planted with Madin-Darby Canine Kidney (MDCK) cells at 2.0×105 cells/ml. Five replicates were performed for each vaccine. The plates were incubated at 36±1° C. and 5±0.5% CO2 for 4±1 days. After the incubation period, the plates were fixed, stained for the vector only and read. Titers were calculated for the 50% endpoint using the Reed and Muench method.

Positive Control (CPV-CDV-CAdV2)

Briefly, ten-fold serial dilutions of the vaccine were made. Each dilution was added to each of 5 wells at 100 microliters per well in 96 well plates planted with the appropriate concentration of cells (CPV-MDCK at 2×105 cells/ml, CDV-VERO at 2×105 cells/ml, CAV2-MDCK at 2×105 cells/ml). Five replicates were performed for each antigen fraction. The plates were incubated at 36±1° C. and 5±0.5% CO2 for 3-6 days. After the incubation period, the plates were fixed, stained with a direct FA conjugate, and read. Titers were calculated for the 50% endpoint using the Reed and Muench method.

Sera

Up to 10 mL of whole blood from each dog was collected weekly for serum starting on 0 DPV1. Specific time points included the following: 0 DPV1, 7 DPV1, 14 DPV1, 21 DPV1/0 DPV2, 7 DPV2, and 14 DPV2. Blood was allowed to clot, centrifuged at 1,000-1,300×g to separate the sera and dispensed into at least 2 aliquots. Sera were stored at −20° C. or colder until evaluated for antibody titer.

Serological analysis was performed using a serum neutralization (SN) assay. The SN assay was used to measure serum antibody titers to CAV2, CPV-2b, and CPV-2c.

Briefly, for CAdV2 serology, serial dilutions of heat-inactivated sera were mixed with equal volumes of a viral suspension (50 to 300 FAID50). The serum-virus mixture was incubated at 36±1° C. for one hour. The 96-well microtiter plates were then seeded with MDCK cells (2×105 cells/ml at 0.1 ml/well). Plates were incubated at 36±1° C. in a humidified 5+0.5% CO2 incubator for 5±1 days. Plates were fixed with cold acetone for 15±5 minutes and virus was detected by specific immunofluorescence. Failure to detect the virus by immunofluorescence indicated the presence of SN antibodies. For determination of SN antibody titers, 50% neutralization endpoints were calculated using the Reed and Muench method.

TABLE 4

CAV2 SN GMT Values

| Group | D0 (0 DPV1) | D7 | D14 | D21 (0 DPV2) | D28 | D35 | D43 (0 DPC) | D50 | D57 |
|---|---|---|---|---|---|---|---|---|---|
| rCAV2-CPV VP2 | 1 | 703 | 967 | 645 | 3160 | 3069 | 2170 | 1448 | 1184 |
| MLV | 1 | 7 | 575 | 196 | 384 | 418 | 308 | 228 | 215 |
| Challenge Controls | 1 | 1 | 1 | 1 | 1 | 1 | 1 | 1 | 1 |

Briefly, for CPV-2b serology, serial dilutions of heat-inactivated sera were mixed with equal volumes of a viral suspension (50 to 300 FAID50). The serum-virus mixture was incubated at 36±1° C. for one hour. Dog Kidney (DKFD-00) cells (2.5×105 cells/ml at 0.1 ml/well). were then added to all wells of the 96-well microtiter plate. Plates were incubated at 36±1° C. in a humidified 5±0.5% CO2 incubator for 6±1 days. Plates were fixed with cold acetone for 15±5 minutes and virus was detected by specific immunofluorescence. Failure to detect the virus by immunofluorescence indicated the presence of SN antibodies. For determination of SN antibody titers, 50% neutralization endpoints were calculated using the Reed and Muench method.

TABLE 5

CPV-2b SN GMT Values

| Group | D0 (0 DPV1) | D7 | D14 | D21 (0 DPV2) | D28 | D35 | D43 (0 DPC) | D50 | D57 |
|---|---|---|---|---|---|---|---|---|---|
| rCAV2-CPV VP2 | 1 | 1 | 1 | 6 | 724 | 484 | 558 | 484 | 14596 |
| MLV | 1 | 34 | 1085 | 2170 | 6137 | 6502 | 10935 | 10321 | 10321 |
| Challenge Controls | 1 | 1 | 1 | 1 | 1 | 1 | 1 | 1007 | 8192 |

Briefly, for CPV-2c serology, serial dilutions of heat-inactivated sera were mixed with equal volumes of a viral suspension (50 to 300 FAID50). The serum-virus mixture was incubated at 36±1° C. for one hour. The 96-well microtiter plates were then seeded with MDCK cells (7×104 cells/ml at 0.1 ml/well). Plates were incubated at 36±1° C. in a humidified 5+0.5% CO2 incubator for 5±1 days. Plates were fixed with cold acetone for 15±5 minutes and virus was detected by specific immunofluorescence. Failure to detect the virus by immunofluorescence indicated the presence of SN antibodies. For determination of SN antibody titers, 50% neutralization endpoints were calculated using the Reed and Muench method.

TABLE 6

CPV-2c SN GMT Values

| Group | D0 (0 DPV1) | D7 | D14 | D21 (0 DPV2) | D28 | D35 | D43 (0 DPC) | D50 | D57 |
|---|---|---|---|---|---|---|---|---|---|
| rCAV2-CPV VP2 | 1 | 1 | 2 | 9 | 911 | 684 | 383 | 342 | 10935 |
| MLV | 1 | 14 | 418 | 1772 | 6502 | 8192 | 6137 | 9742 | 7298 |
| Challenge Controls | 1 | 1 | 1 | 1 | 1 | 1 | 1 | 103 | 724 |

A distinct antibody response was noted in relation to the 3 groups when compared to each other for CAdV2, CPV-2b and CPV-2c antibodies.

The CAdV2-CPV VP2 group exhibited a much stronger CAdV2 antibody response at 7 DPV1 as compared to the MLV group, however, by 14 DPV1 the GMT values of the groups were similar. The antibody titers for both groups were waning by 21 DPV1 at which point the animals were boostered. After the booster, both groups' antibody levels spiked and then gradually leveled off, with the CAdV2-CPV VP2 group leveling off at a higher titer than the MLV group. The negative control group remained negative for CAdV2 antibodies throughout the course of the study.

In contrast to the CAdV2 antibody response of the 2 vaccinate groups, the CPV antibody response of the CAdV2-CPV VP2 group was minimal up to second vaccination, at which point the CPV antibody titer spiked at 7 DPV2 and then leveled off until challenged with CPV. After challenge the CAdV2-CPV VP2 groups antibody response again spiked. The MLV vaccine responded well to the first vaccination, with an additional response to the second vaccination. The CPV antibody levels in the MLV group leveled off after the second vaccination and did not show a significant increase during the challenge phase of the study. The negative control animals remained negative for CPV antibodies throughout the vaccination phase until the first bleed after the time of challenge at which point they exhibited significant CPV antibody titer.

Clinical Observations:

All animals were observed and rectal temperatures were taken daily for baseline to the nearest tenth of a degree (Fahrenheit) on −2, −1 and 0 DPC. After challenge, the animals were monitored daily for up to 14 days where rectal temperature and observations of clinical signs were taken. Animal cages were not cleaned until observations had been completed for the day.

Clinical signs of CPV included, but were not limited to the following: (1) Bloody Stool—A specific stool containing at least 10% blood, usually associated with diarrhea and/or mucus; stool is typically a dark red color and has a distinctive strong iron smell; (2) Mucoid Stool—A specific stool containing at least 10% mucus may be associated with diarrhea, and may or may not contain blood. A mucoid stool may or may not have texture and/or form; (3) Diarrhea—Watery, no texture, flat puddles; (4) Fever was indicated if the rectal temperature was ≥103.4° F. and at least 1 degree Fahrenheit above the baseline temperature. Hypothermia was indicated if the temperature was 99.5° F. or lower and at least one degree Fahrenheit below baseline temperature.

All dogs were weighed to the nearest tenth of a kilogram (kg) on 0, 7 and 14 DPC for determination of weight loss/gain post-challenge. All weights were collected on the Body Weight Record.

For clinical signs, a single occurrence of any clinical sign typical of CPV infection including, diarrhea, mucus in stool, or blood in stool following challenge defined an animal as positive for clinical signs. Inappetence, depression/lethargy, and the presence of vomit were also noted for use as supportive criteria for assessing an animal as positive for parvovirus infection.

Four (4) of the 18 animals in this study exhibited diarrhea or vomit on 2 DPC. These clinicals are outside the typical CPV onset range of 3-4 DPC and may be due to fasting and/or the anesthesia procedure used during the challenge. They are not considered signs of CPV infection.

The rCAdV2-CPV VP2 group (Group 1) showed no signs of infection until 10 DPC where 1 of 6 animals exhibited bloody, mucous stool for 1 day. It should be noted that 1 animal in the group did show signs of vomit at 2 DPC, which is outside the range of CPV onset as stated previously, and is therefore not considered a sign of infection.

In the MLV group (Group 2) 2 of 6 animals exhibited clinical signs on 5 and 7 DPC, where dog #12 was noted with a mucous stool on 7 DPC and dog #13 had diarrhea on 5 and 7 DPC. It should also be noted that 3 animals in this group showed signs of vomit or diarrhea on 2 DPC, which is outside the range of CPV onset as stated previously, and are therefore not considered signs of infection.

All dogs in the negative control group (Group 3) exhibited a range of moderate to severe clinical signs (diarrhea, mucoid stool, dehydration, vomit, inappetence, bloody stool) starting at 4 DPC and concluding on 11 DPC with 4 animals succumbing to CPV (3 on 7 DPC and 1 on 8 DPC).

Pyrexia: For pyrexia, a single occurrence of pyrexia (rectal temperature ≥103.4° F. and at least 1 degree above pre-challenge baseline) following challenge, categorized an animal as positive.

The rCAdV2-CPV VP2 test group (Group 1) exhibited 1 instance of pyrexia in 3 of 6 animals; 1 on 9 DPC and 2 on 12 DPC. None of the 6 animals in the MLV group (Group 2) exhibited pyrexia. In the negative control group (Group 3) 3 of the 6 animals showed at least 1 instance of pyrexia (1 animal showed 2 instances) ranging from 4 to 5 DPC. Two of the 6 animals exhibited hypothermia on 7 DPC.

Weight: To determine weight loss/gain, on a weekly basis, the weight for each individual animal was assessed by subtracting the weight from the previous week.

No animals in the rCAdV2-CPV VP2 test group (Group 1) nor the MLV test group (Group 2) exhibited weight loss at 7 or 14 DPC. All animals in the negative control group (Group 3) did exhibit weight loss at 7 DPC ranging from 0.1 to 0.8 kilograms. The animals remaining on test in Group 3 at 14 DPC experienced weight gain from 7 DPC.

Lymphopenia: For lymphopenia, a single occurrence of lymphopenia (≥50% loss of pre-challenge baseline) following challenge categorized a canine as positive. In this study the rCAdV2-CPV VP2 test group (Group 1) included 3 of 6 animals with at least 1 instance of lymphopenia with an onset ranging from 9-12 DPC. The MLV group (Group 2) did not exhibit signs of lymphopenia. All animals in the negative control group (Group 3) had at least 1 instance of lymphopenia with onset at 4 DPC.

Leukopenia: For leukopenia, a single occurrence of leukopenia (≥50% loss of pre-challenge baseline) following challenge categorized a canine as positive. In this study the rCAdV2-CPV VP2 test group (Group 1) and the MLV group (Group 2) did not exhibit signs of leukopenia. The negative control group (Group 3) included 5 of 6 animals which had at least 1 instance of leukopenia with onset at 6 DPC.

Virus Isolation from Fecal Samples: For CPV fecal virus isolation, a single occurrence of detection of CPV virus in feces following challenge categorized a canine as positive. A CPV fecal virus titer of ≤1.5 Log 10FAID50/ml was recorded as negative for CPV fecal virus isolation. All other recorded titers >1.5 Log 10FAID50/ml were categorized as positive for CPV fecal virus detection.

In this study, the rCAdV2-CPV VP2 (Group 1), group included 4 of 6 animals that exhibited at least 1 day of virus shedding initiating between 8 and 14 DPC. The MLV group (Group 2) did not shed detectable amounts of live virus. All animals in the negative control group shed detectable amounts of virus in the feces initiating on 3 or 4 DPC and lasting through 9 DPC.

Summary of Results:

In summary, canines, 6 weeks 2 days to 7 weeks 2 days of age, were vaccinated with 1.0 ml of the following vaccines on 0 DPV1 and 21 DPV1: (Group 1) rCAdV2-CPV VP2=8.0 logs/ml; (Group 2) MLV Combo—CAdV2/CDV/CPV=4.7/2.6/3.9 logs/ml; (Group 3). PBS Control. All vaccinated canines were challenged with virulent CPV-2b, oro-nasally on 22 DPV2.

The rCAdV2-CPV VP2 test vaccine did not meet efficacy criteria when given in a 2-dose regimen at 8.0 logs per dose. Three (3) dogs exhibited fever, shedding of CPV in feces and lymphopenia and 1 dog exhibited definitive clinical signs of canine parvovirus. A fourth dog exhibited only shedding of CPV. The vaccine appeared to provide initial protection until approximately 10 DPC, which is a delayed onset of clinical signs of infection as compared to the negative controls. One vaccinate was reported with a complete clouding of the cornea with no known cause.

Example 8: Preparation of Pharmaceutical Compositions (Vaccines) Comprising rCAdV-EHV-4 p430/RabG (N)

Preparation of Pharmaceutical Compositions (Vaccines) Comprising rCAdV-EHV-4p430/RabG (N)Vaccine:

Vaccine Formulation:

rCAdV-EHV-4 pp430/RabG (N)tissue culture stock was diluted with 0.01M PBS to the target dose. No adjuvants were used.

Inoculation of Pigs with rCAdV-EHV-4 P430/RabG (N) and Assessment of the Serological Response:

Study Design: Vaccinated piglets and control groups ages 4-8 weeks of age, dosing (single/two dose) was 2 ml/dose intramuscularly.

To investigate its properties as a vectored vaccine in young piglets, rCAdV-EHV-4 P(GG430) RABG (N) C1 was tested in a vaccination-serology study.

In detail, piglets were vaccinated twice with rCAdV-EHV-4 p430/RabG (N) C1 at a dose of 6.7 logs at study day 0 and 21 (two-shot vaccination, 2× rCAdV). A non-vaccinated group served as negative control.

Serology: Assays to Measure Seroconversion After Vaccination

The induction of CAdV-2 neutralizing antibodies after vaccination was tested in sera from animals vaccinated once or twice with the rCAdV-2 p430 RabG vaccine. Vaccinated animals showed detectable virus neutralization (VN) titers to the CAdV2, while sera from the non-vaccinated groups had no detectable CAdV-2 neutralizing antibody levels (Table 2.). Rapid fluorescent foci inhibition tests (RFFIT) performed on sera by the Rabies Laboratory at Kansas State University showed detectable RFFIT titers in 3 of 12 vaccinated animals and no detectable RFFIT titers in control groups) measuring rabies neutralizing antibodies. Whole rabies antibody testing by ELISA as well as CAdV viral shedding was also tested.

TABLE 7

| Serology | | | | | | | | | | |
|---|---|---|---|---|---|---|---|---|---|---|
| | Study Day | 0 DPV1 | | | 21 DPV1 | | | 35 DPV1, 14 DPV2 | | |
| | ASSAY | CAV-2 VN | ELISA | RFFIT | CAV-2 VN | ELISA | RFFIT | CAV-2 VN | ELISA | RFFIT |
| | Piglet ID | | | | | | | | | |
| Placebo Controls | 502 | < 2 | | ** | | | | < 2 | | ** |
| | 506 | < 2 | | ** | | | | < 2 | | ** |
| | 508 | < 2 | | ** | | | | < 2 | | ** |
| | 525 | < 2 | | ** | | | | < 2 | | ** |
| | 527 | < 2 | | ** | | | | < 2 | | ** |
| | 529 | < 2 | | ** | | | | < 2 | | ** |
| | 531 | < 2 | | ** | | | | < 2 | | ** |
| | 548 | < 2 | | ** | | | | < 2 | | ** |
| | 580 | < 2 | | ** | | | | < 2 | | ** |
| rCAV-2 MCP RabG Vaccinated | 501 | < 2 | | ** | 45 | | ** | 128 | | ** |
| | 507 | < 2 | | ** | 32 | | ** | 128 | | ** |
| | 509 | < 2 | | ** | 64 | | ** | 91 | | ** |
| | 516 | < 2 | | ** | 23 | | ** | 45 | | ** |
| | 517 | < 2 | | ** | 2 | | ** | 23 | | ** |
| | 519 | < 2 | | ** | < 2 | | ** | 16 | | 0.1 IU/mL |
| | 521 | < 2 | | ** | 45 | | ** | 181 | | ** |
| | 524 | < 2 | | ** | 45 | | ** | 64 | | ** |
| | 528 | < 2 | | ** | 32 | | ** | 91 | | ** |
| | 532 | < 2 | | ** | 16 | | ** | 23 | | 0.1 IU/mL |
| | 533 | < 2 | | ** | < 2 | | ** | 45 | | ** |
| | 534 | < 2 | | ** | 64 | | 0.1 IU/mL | 181 | | ** |

These results confirm the utility of the EHV-4 promoters of the present invention in the CAdV vector by demonstrating effective expression of the transgene of interest (by expression evaluation of what proportion of the vaccine virus leads to expression of transgene of interest in infected cells), as well as viral rescue, and immunogenicity of the transgene in vaccinated animals. Expression evaluation was not even possible with CAdV vectors with expression cassettes driven by the CMV promoters. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.

1. Buonavoglia, C. and V. Martella, Canine respiratory viruses. Vet Res, 2007. 38(2): p. 355-73.
2. Tham, K. M., G. W. Horner, and R. Hunter, Isolation and identification of canine adenovirus type-2 from the upper respiratory tract of a dog. N Z Vet J, 1998. 46(3): p. 102-5.
3. Hamelin, C., P. Jouvenne, and R. Assaf, Association of a type-2 canine adenovirus with an outbreak of diarrhoeal disease among a large dog congregation. J Diarrhoeal Dis Res, 1985. 3(2): p. 84-7.
4. Macartney, L., H. M. Cavanagh, and N. Spibey, Isolation of canine adenovirus-2 from the faeces of dogs with enteric disease and its unambiguous typing by restriction endonuclease mapping. Res Vet Sci, 1988. 44(1): p. 9-14.
5. Benetka, V., et al., Canine adenovirus type 2 infection in four puppies with neurological signs. Vet Rec, 2006. 158(3): p. 91-4.
6. Appel, M., et al., Pathogenicity of low-virulence strains of two canine adenovirus types. Am J Vet Res, 1973. 34(4): p. 543-50.
7. Appel, M., L. E. Carmichael, and D. S. Robson, Canine adenovirus type 2-induced immunity to two canine adenoviruses in pups with maternal antibody. Am J Vet Res, 1975. 36(08): p. 1199-202.
8. Bittle, J. L., W. A. Grant, and F. W. Scott, Canine and feline immunization guidelines—1982. J Am Vet Med Assoc, 1982. 181(4): p. 332-5.
9. Curtis, R. and K. C. Barnett, The 'blue eye' phenomenon. Vet Rec, 1983. 112(15): p. 347-53
10. Bru, T., S. Salinas, and E. J. Kremer, An update on canine adenovirus type 2 and its vectors. Viruses, 2010. 2(9): p. 2134-53.
11. Hu, R. L., et al., Experimental immunization of cats with a recombinant rabies-canine adenovirus vaccine elicits a long-lasting neutralizing antibody response against rabies. Vaccine, 2007. 25(29): p. 5301-7.
12. Hu, R., et al., Prevention of rabies virus infection in dogs by a recombinant canine adenovirus type-2 encoding the rabies virus glycoprotein. Microbes Infect, 2006. 8(4): p. 1090-7.
13. Li, J., et al., A single immunization with a recombinant canine adenovirus expressing the rabies virus G protein confers protective immunity against rabies in mice. Virology, 2006. 356(1-2): p. 147-54.
14. Henderson, H., et al., Oral immunization of raccoons and skunks with a canine adenovirus recombinant rabies vaccine. Vaccine, 2009. 27(51): p. 7194-7.
15. Bouet-Cararo, C., et al., Canine adenoviruses elicit both humoral and cell-mediated immune responses against rabies following immunisation of sheep. Vaccine, 2011. 29(6): p. 1304-10.

16. Liu, Y., et al., Efficacy and safety of a live canine adenovirus-vectored rabies virus vaccine in swine. Vaccine, 2008. 26(42): p. 5368-72.
17. Fischer, L., et al., Vaccination of puppies born to immune dams with a canine adenovirus-based vaccine protects against a canine distemper virus challenge. Vaccine, 2002. 20(29-30): p. 3485-97.
18. Yang, S., et al., Complete protection of cats against feline panleukopenia virus challenge by a recombinant canine adenovirus type 2 expressing VP2 from FPV. Vaccine, 2008. 26(11): p. 1482-7.
19. Zhang, S., et al., Oral vaccination of dogs (*Canis familiaris*) with baits containing the recombinant rabies-canine adenovirus type-2 vaccine confers long-lasting immunity against rabies. Vaccine, 2008. 26(3): p. 345-50.
20. Gallichan, W. S., et al., Mucosal immunization with a recombinant adenovirus vector induces local and systemic immunity and protection from herpes simplex virus. Adv Exp Med Biol, 1995. 371B: p. 1581-5.
21. Lubeck, M. D., et al., Immunogenicity of recombinant adenovirus-human immunodeficiency virus vaccines in chimpanzees following intranasal administration. AIDS Res Hum Retroviruses, 1994. 10(11): p. 1443-9.
22. Wang, Y., et al., The use of an E1-deleted, replication-defective adenovirus recombinant expressing the rabies virus glycoprotein for early vaccination of mice against rabies virus. J Virol, 1997. 71(5): p. 3677-83.
23. Papp, Z., L. A. Babiuk, and M. E. Baca-Estrada, The effect of pre-existing adenovirus-specific immunity on immune responses induced by recombinant adenovirus expressing glycoprotein D of bovine herpesvirus type 1. Vaccine, 1999. 17(7-8): p. 933-43.
24. Babiuk, L. A. and S. K. Tikoo, Adenoviruses as vectors for delivering vaccines to mucosal surfaces. J Biotechnol, 2000. 83(1-2): p. 105-13.
25. Wright, N., et al., High prevalence of antibodies against canine adenovirus (CAV) type 2 in domestic dog populations in South Africa precludes the use of CAV-based recombinant rabies vaccines. Vaccine, 2013. 31(38): p. 4177-82.
26. Kremer, E. J., et al., Canine adenovirus vectors: an alternative for adenovirus-mediated gene transfer. J Virol, 2000. 74(1): p. 505-12.
27. Linne, T., Differences in the E3 regions of the canine adenovirus type 1 and type 2. Virus Res, 1992. 23(1-2): p. 119-33.
28. Chartier, C., et al., Efficient generation of recombinant adenovirus vectors by homologous recombination in *Escherichia coli*. J Virol, 1996. 70(7): p. 4805-10.
29. Lopez de Turiso, J. A., et al., Recombinant vaccine for canine parvovirus in dogs. J Virol, 1992. 66(5): p. 2748-53.
30. Langeveld, J. P., et al., First peptide vaccine providing protection against viral infection in the target animal: studies of canine parvovirus in dogs. J Virol, 1994. 68(7): p. 4506-13.
31. Boshart M, Weber F, Jahn G, Dorsch-Hasler K, Fleckenstein B, Schaffner W. 1985. A very strong enhancer is located upstream of an immediate early gene of human cytomegalovirus. Cell 41(2):521-30.
32. Bryant, N. A., Davis-Poynter, N., Vanderplasschen, A., and Alcami, A. 2003. Glycoprotein G isoforms from some alphaherpesviruses function as broad-spectrum chemokine binding proteins. The EMBO Journal Vol. 22 (4): 833-846.
33. Bustin, S. 2000. Absolute quantification of mRNA using real-time reverse transcription polymerase chain reaction assays. Journal of Molecular Endocrinology 25(2): 169-193.
34. Charoensawan, V., Wilson, D., Teichmann, S. A. 2010. Genomic repertoires of DNA-binding transcription factors across the tree of life. Nucleic Acids Res. 38(21): 7364-77
35. Colle, C. F. 3rd, O'Callaghan, D. J. 1995. Transcriptional analyses of the unique short segment of EHV-1 strain Kentucky A. Virus Genes; 9(3):257-68.
36. Donnelly, M. L., Luke, G., Mehrotra, A., Li, X., Hughes, L. E., Gani, D., and Ryan, M. D. 2001. Analysis of the aphthovirus 2A/2B polyprotein 'cleavage' mechanism indicates not a proteolytic reaction, but a novel translational effect: a putative ribosomal 'skip'. J Gen Virol. 82(Pt 5):1013-25
37. Dorsch-Hasler, K., Keil, G. M., Weber, F., Jasin, M. Schaffner, W., and Koszinowski, U. H. 1985. A long and complex enhancer activates transcription of the gene coding for the highly abundant immediate early mRNA in murine cytomegalovirus. PNAS Vol. 82: 8325-8329.
38. Drummer, H. E., Studdert, M. J., Crabb, B. S. 1998. Equine herpesvirus-4 glycoprotein G is secreted as a disulphide-linked homodimer and is present as two homodimeric species in the virion. J. Gen. Virol. 79: 1205-1213
39. Fields, B, Knipe, D. M.; and Howley, P. M. 2013. Virology. $6^{th}$ ed. Philadelphia; Wolters Kluwer Health/Lippincott Williams&Wilkins
40. Foecking, M. K., Hofstetter, H. 1986. Powerful and versatile enhancer-promoter unit for mammalian expression vectors. Gene 45(1):101-5.
41. Goodwin, E. C. & Rottman, F. M. 1992. The 3' flanking sequence of the bovine growth hormone gene contains novel elements required for efficient and accurate polyadenylation. J. Biol. Chem. 267: 16330-16334.
42. Jang, S. K., Pestova, T. V., Hellen, C. U., Witherell, G. W., Wimmer, E. 1990. Cap-independent translation of picornavirus RNAs: structure and function of the internal ribosomal entry site. Enzyme.; 44(1-4):292-309.
43. Kim, D. W., Uetsuki, T., Kaziro, Y., Yamaguchi, N., Sugano, S. 1990. Use of the human elongation factor 1 alpha promoter as a versatile and efficient expression system. Gene 16; 91(2):217-23.
44. Lee, E. C., Yu, D., Martinez de Velasco, J., Tessarollo, L., Swing, D. A. et al. 2001. A highly efficient *Escherichia coli*-based chromosome engineering system adapted for recombinogenic targeting and subcloning of BAC DNA. Genomics 73: 56-65.
45. Luke, G A and Ryan, M D. 2013. The protein coexpression problem in biotechnology and biomedicine: virus 2A and 2A-like sequences provide a solution. Future Virology, Vol. 8, No. 10, Pages 983-996.
46. Ma, G., Eschbaumer, M., Said, A., Hoffmann, B., Beer, M., Osterrieder, N. 2012. An equine herpesvirus type 1 (EHV-1) expressing VP2 and VP5 of serotype 8 bluetongue virus (BTV-8) induces protection in a murine infection model. PLoS One. 2012; 7(4):e34425. doi: 10.1371/journal.pone.0034425. Epub 2012 Apr. 12.
47. Ma, G., Azab, W., Osterrieder, N. 2013. Equine herpesviruses type 1 (EHV-1) and 4 (EHV-4)—masters of co-evolution and a constant threat to equids and beyond. Vet Microbiol. 167(1-2):123-34.
48. Nolan, T. Rebecca E Hands, R. E., and Bustin S. A. Journal name: 2006. Quantification of mRNA using real-time RT-PCR Nature Protocols 1: 1559-1582

49. Osterrieder, N., Neubauer, A., Brandmüller, C., Kaaden, O. R., and O'Callaghan, D. J. 1996. The equine herpesvirus 1 IR6 protein influences virus growth at elevated temperature and is a major determinant of virulence. Virology 226:243-251.

50. Proudfoot, N. J. 2011. Ending the message: poly(A) signals then and now. Genes&Development 25:1770-1782.

51. Ptashne, M. 2014. *The Chemistry of Regulation of Genes and Other Things* The Journal of Biological Chemistry Vol. 289, (9) 5417-5435. Reed, L. J., and Muench, H. 1938. A simple method of estimating fifty percent endpoints. Am. J. Hyg. (27) 3; 493-497.

52. Rosas, C. T., Konig, P., Beer, M., Dubovi, E. J., Tischer, B. K., Osterrieder, N., 2007a. Evaluation of the vaccine potential of an equine herpesvirus type 1 vector expressing bovine viral diarrhea virus structural proteins. J. Gen. Virol. 88 (3), 748-757.

53. Rosas, C. T., B. K. Tischer, G. A. Perkins, B. Wagner, L. B. Goodman, N. Osterrieder. 2007b. Live-attenuated recombinant equine herpesvirus type 1 (EHV-1) induces a neutralizing antibody response against West Nile virus (WNV) Virus Research, 125, pp. 69-78.

54. Rosas, C. T., Van de Walle, G. R., Metzger, S. M., Loelzer, K., Dubovi, E. J., Kim, S. G., Parrish, C. R., Osterrieder, N., 2008. Evaluation of a vectored equine herpesvirus type 1 (EHV-1) vaccine expressing H3 haemagglutinin in the protection of dogs against canine influenza. Vaccine 26 (19), 2335-3234.

55. Ryan, M. D., and Drew J. 1994. Foot-and-mouth disease virus 2A oligopeptide mediated cleavage of an artificial polyprotein. EMBO J February 15; 13(4):928-33.

56. Said, A., Elke Lange, E., Beer, M. Damiani, A., Osterrieder, N. 2013. Recombinant equine herpesvirus 1 (EHV-1) vaccine protects pigs against challenge with influenza A(H1N1)pmd09 Virus Research 173: 371-376

57. Shaner, N. C., Campbell, R. E., Steinbach, P. A., Giepmans, B. N., Palmer, A. E., Tsien, R, Y. 2004. Improved monomeric red, orange and yellow fluorescent proteins derived from *Discosoma* sp. red fluorescent protein. Nat Biotechnol. December; 22(12):1567-72. Epub 2004 Nov. 21.

58. Tischer, B. K., von Einem, J., Kaufer, B., Osterrieder, N., 2006. Two-step red-mediated recombination for versatile high-efficiency markerless DNA manipulation in *Escherichia coli*. Biotechnol. Tech. 40, 191-197.

59. Tischer, B. K., Kaufer, B. B., Sommer, M., Wussow, F., Arvin, A., and Osterrieder, N. A Self-Excisable Infectious Bacterial Artificial Chromosome Clone of Varicella-Zoster Virus Allows Analysis of the Essential Tegument Protein Encoded by ORF9. J. Virol. 81 (23), 2007, 13200-13208.

60. Tischer, B. K, Smith, G. A., and Osterrieder, N. in: Jeff Braman (ed.), *In vitro Mutagenesis Protocols: Third Edition*, Methods in Molecular Biology, vol. 634, DOI 10.1007/978-1-60761-652-8_30, © Springer Science+Business Media, LLC 2010, Chapter 30: *En Passant* Mutagenesis: A Two Step Markerless Red Recombination System.

61. Thompson, S. R. 2012. Tricks an IRES uses to enslave ribosomes. Trends Microbiol. November; 20(11):558-66.

62. Trapp, S., von Einem, J., Hofmann, H., Kostler, J., Wild, J., Wagner, R., Beer, M., Osterrieder, N., 2005. Potential of equine herpesvirus 1 as a vector for immunization. J. Virol. 79, 5445-5454.

63. Wellington, J. E., Allen, G. P., Gooley, A. A., Love, D. N., Packer, N. H., Yan, J. X., Whalley, J. M. 1996. The highly O-glycosylated glycoprotein gp2 of equine herpesvirus 1 is encoded by gene 71. J Virol. 70(11):8195-8.

What is claimed is:

1. A recombinant canine adenovirus (rCAdV) vector comprising an expression cassette encoding a heterologous DNA operably linked to an equine herpesvirus-4 (EHV4) promoter sequence, wherein the EHV4 promoter sequence is either (i) an EHV4 ORF 42 promoter sequence comprising a polynucleotide having at least 95% sequence identity to SEQ ID NO: 32, or (ii) an EHV4 ORF 70 promoter sequence comprising a polynucleotide having at least 95% sequence identity to SEQ ID NO: 31.

2. The rCAdV vector of claim 1, wherein the EHV4 promoter sequence is the EHV4 ORF 42 promoter sequence.

3. The rCAdV vector of claim 1, wherein the EHV4 promoter sequence is the EHV4 ORF 70 promoter sequence.

4. The rCAdV vector of claim 2, wherein the EHV4 ORF 42 promoter sequence comprises a polynucleotide having at least 95% sequence identity to SEQ ID NO: 30.

5. The rCAdV vector of claim 3, wherein the EHV4 ORF 70 promoter sequence comprises a polynucleotide having at least 95% sequence identity to SEQ ID NO. 29.

6. The rCAdV vector of claim 5, wherein the EHV4 ORF 70 promoter sequence comprises SEQ ID NO.:29.

7. The rCAdV vector of claim 4, wherein EHV4 ORF 42 promoter sequence comprises SEQ ID NO.:30.

8. The rCAdV vector of claim 3, wherein the EHV4 ORF 70 promoter sequence comprises SEQ ID NO.:31.

9. The rCAdV vector of claim 2, wherein the EHV4 ORF 42 promoter sequence comprises SEQ ID NO.:32.

10. The rCAdV vector of claim 1, wherein the rCAdV vector is an infectious canine adenovirus.

11. The rCAdV vector of claim 1, wherein the heterologous DNA encodes an antigenic epitope, a growth factor, or, a fusion protein, or wherein the heterologous DNA comprises a therapeutic gene.

12. The rCAdV vector of claim 11, wherein the heterologous DNA encodes the antigenic epitope.

13. The rCAdV vector of claim 12, wherein the antigenic epitope is from a canine or feline pathogen.

14. The rCAdV vector of claim 12, wherein the antigenic epitope is derived from a food producing animal pathogen.

15. The rCAdV vector of claim 13, wherein the antigenic epitope is from a Morbillivirus antigen, a rabies glycoprotein, a Feline Leukemia virus (FeLV) envelope protein, an immunodeficiency virus antigen, a parvovirus antigen, or a poxvirus antigen.

16. The rCAdV vector of claim 14, wherein the food producing animal pathogen is a swine, cattle, equine, poultry, and/or ovine pathogen.

17. An immunogenic composition comprising:

the rCAdV vector according to claim 1; and a veterinary-acceptable acceptable carrier or diluent.

18. The immunogenic composition of claim 17, wherein the carrier or diluent is suitable for oral, intradermal, intramuscular, or intranasal application.

19. A method for producing an immunogenic composition, comprising:

infecting a host cell with the rCAdV vector according to claim 1;

cultivating the infected host cell;

harvesting the rCAdV vector from the infected host cell; and admixing the harvested rCAdV vector with a pharmaceutically acceptable carrier.

20. A method for inducing an immune response against a pathogen in an animal, comprising:

administering to the animal an effective amount of the immunogenic composition according to claim 17.

21. The method of claim 20, wherein the immunogenic composition is administered once.

22. The method of claim 20, wherein the immunogenic composition is administered as two doses.

23. The method of claim 20, wherein the immunogenic composition is administered orally, intradermally, intramuscular, or intranasally.

24. A kit for inducing an immune response against a pathogen in an animal, comprising:

the immunogenic composition according to claim 17; and a dispenser capable of administering the immunogenic composition to the animal.

25. A eukaryotic host cell line which expresses the rCAdV vector according to claim 1.

26. The eukaryotic host cell line of claim 25, wherein the host cell line is a PK/WRL cell line, a RK13 cell line, a MDBK cell line, a ST cell line, an AI-ST cell line, a VERO cell line, a Sf9 cell line, a Sf21, a Sf plus cell line, or a MDCK cell line.

27. A prokaryotic host cell line which expresses the rCAdV vector according to claim 1.

* * * * *

SEQUENCE LISTING

<160> NUMBER OF SEQ ID NOS: 47

<210> SEQ ID NO 1
<211> LENGTH: 1010
<212> TYPE: DNA
<213> ORGANISM: Canine adenovirus type 2

<400> SEQUENCE: 1
ctcccaaata ggtataaaaa gcccagtgct ggctggcacg ggcattcagc ttagcgaaga 60
catccccagc gcctcctgga tcaggcccga cggcatattc cagctaggag gggggtctcg 120
ctcgtccttc agcccaacgc aagcattcct caccctgcaa caggcatcct cgacgccgcg 180
cgcaggaggc gtgggcacct accagtttgt gcgcgaattt gtgccagagg tataccttaa 240
ccctttttca ggaccaccgg acacctttcc tgatcagttc attcctaact acgacattgt 300
aaccaactct gtcgatggct atgactgagg agagcatgga ccaggtggag gtgaactgcc 360
tgtgtgctca gcatgcccaa acctgcacgc gccctcgctg ctttgcaaag gagggtttat 420
gtgctaactg gttttacaac ccagcacttg cctttgaagg gtttgatatt ccagactctt 480
accaagaggg acacggtgtg attcccagag tgcgtcctca acatcacccg cgacggaact 540
ttcctgctta ttggggatag caaaaagacc ccctatgtca tcctgctgcc cttttttgca 600
aaccccaaag aagacactcc aattttaatg gcccttagcc attccatgcc cgtcgccata 660
cctgacactg caatgcctat atatatttcc atcatgtttt ttattgtggc catgctagcc 720
accctcagcc ttctaatggg actaaacaac aaaaatcagg cccatgtagc ttgtcaaata 780
aacttaccta atttttgcta agacgtctgg gtcctgcgtt tctatgtcca ccaaagtccc 840
ctcttcccag ctttggtact tccacttgtg cgcgcgagcc agcttgcgga tgtgcttgaa 900
agataatgtg gtctctccca acagcttccc gttcaccagc accagggcca tgaagcggac 960
acgaagagct ctacctgcaa attatgaccc tgtatatcca tacgacgccc 1010

<210> SEQ ID NO 2
<211> LENGTH: 1011
<212> TYPE: DNA
<213> ORGANISM: Canine adenovirus type 2

<400> SEQUENCE: 2
ctcccaaata ggtataaaaa gcccagtgct ggctggcacg ggcattcagc ttagcgaaga 60
catccccagc gcctcctgga tcaggcccga cggcatattc cagctaggag gggggtctcg 120
ctcgtccttc agcccaacgc aagcattcct caccctgcaa caggcatcct cgacgccgcg 180
cgcaggaggc gtgggcacct accagtttgt gcgcgaattt gtgccagagg tataccttaa 240 cccttttca ggaccaccgg acacctttcc tgatcagttc attcctaact acgacattgt 300
aaccaactct gtcgatggct atgactgagg agagcatgga ccaggtggag gtgaactgcc 360
tgtgtgctca gcatgcccaa acctgcacgc gccctcgctg ctttgcaaag gagggtttat 420
gtgctaactg gttttacaac ccagcacttg cctttgaagg gtttgatatt ccagactctt 480
accaagaggg acacggtgtg acaccctcag ccttctaatg ggactaaaca acaaaaatca 540
ggcccatgta gcttgtcaaa taaacttacc taatttttgc taagacgtct gggtcctgcg 600
tttctatgtc caccaaagtc cctcttccc agctttggta cttccacttg tgcgcgcgag 660
ccagcttgcg gatgtgcttg aaagataatg tggtctctcc caacagcttc ccgttcacca 720
gcaccagggc catgaagcgg acacgaagag ctctacctgc aaattatgac cctgtatatc 780
catacgacgc ccccgggtct tccacacaac cccctttttt taataacaag caaggtctca 840
ctgagtcacc cccaggaacc ctggctgtca atgtttcccc tccactaacc ttttctacgt 900
taggtgccat taaactttcc acaggtcccg gactcaccct caacgagggc aagttacaag 960
ccagcttagg gcccggcctc atcacaaata ccgagggcca aatcactgtt g 1011

<210> SEQ ID NO 3
<211> LENGTH: 545
<212> TYPE: DNA
<213> ORGANISM: Artificial Sequence
<220> FEATURE:
<223> OTHER INFORMATION: NUCLEOTIDE SEQUENCE FROM HUMAN CMV PROMOTER

<400> SEQUENCE: 3
ttattaatag taatcaatta cggggtcatt agttcatagc ccatatatgg agttccgcgt 60
tacataactt acggtaaatg gcccgcctgg ctgaccgccc aacgaccccc gcccattgac 120
gtcaataatg acgtatgttc ccatagtaac gccaataggg actttccatt gacgtcaatg 180
ggtggagtat ttacggtaaa ctgcccactt ggcagtacat caagtgtatc atatgccaag 240
tacgccccct attgacgtca atgacggtaa atggcccgcc tggcattatg cccagtacat 300
gaccttatgg gactttccta cttggcagta catctacgta ttagtcatcg ctattaccat 360
ggtgatgcgg ttttggcagt acatcaatgg gcgtggatag cggtttgact cacggggatt 420
tccaagtctc caccccattg acgtcaatgg gagtttgttt tggcaccaaa atcaacggga 480
ctttccaaaa tgtcgtaaca actccgcccc attgacgcaa atgggcggta ggcgtgtacg 540

-continued gtggc 545

<210> SEQ ID NO 4
<211> LENGTH: 1110
<212> TYPE: DNA
<213> ORGANISM: Artificial Sequence
<220> FEATURE:
<223> OTHER INFORMATION: NUCLEOTIDE SEQUENCE FROM HUMAN CMV PROMOTER AND AD5 LEADER

<400> SEQUENCE: 4
ttattaatag taatcaatta cggggtcatt agttcatagc ccatatatgg agttccgcgt 60
tacataactt acggtaaatg gcccgcctgg ctgaccgccc aacgaccccc gcccattgac 120
gtcaataatg acgtatgttc ccatagtaac gccaataggg actttccatt gacgtcaatg 180
ggtggagtat ttacggtaaa ctgcccactt ggcagtacat caagtgtatc atatgccaag 240
tacgccccct attgacgtca atgacggtaa atggcccgcc tggcattatg cccagtacat 300
gaccttatgg gactttccta cttggcagta catctacgta ttagtcatcg ctattaccat 360
ggtgatgcgg ttttggcagt acaccaatgg gcgtggatag cggtttgact cacggggatt 420
tccaagtctc caccccattg acgtcaatgg gagtttgttt tggcaccaaa atcaacggga 480
ctttccaaaa tgtcgtaata accccgcccc gttgacgcaa atgggcggta ggcgtgtacg 540
gtgggaggtc tatataagca gagctcgttt agtgaaccgt cagatcctca ctctcttccg 600
catcgctgtc tgcgagggcc agctgttggg ctcgcggttg aggacaaact cttcgcggtc 660
tttccagtac tcttggatcg gaaacccgtc ggcctccgaa cggtactccg ccaccgaggg 720
acctgagcca gtccgcatcg accggatcgg aaaacctctc gagaaaggcg tctaaccagt 780
cacagtcgca aggtaggctg agcaccgtgg cgggcggcag cgggtggcgg tcggggttgt 840
ttctggcgga ggtgctgctg atgatgtaat taaagtaggc ggtcttgagc cggcggatgg 900
tcgaggtgag gtgtggcagg cttgagatcc agctgttggg gtgagtactc cctctcaaaa 960
gcgggcatga cttctgcgct aagattgtca gtttccaaaa acgaggagga tttgatattc 1020
acctggcccg atctggccat acacttgagt gacaatgaca tccactttgc ctttctctcc 1080
acaggtgtcc actcccaggt ccaagtataa 1110

<210> SEQ ID NO 5
<211> LENGTH: 25
<212> TYPE: DNA
<213> ORGANISM: Artificial Sequence
<220> FEATURE:
<223> OTHER INFORMATION: PRIMER

<400> SEQUENCE: 5
ttattaatag taatcaatta cgggg 25

<210> SEQ ID NO 6
<211> LENGTH: 23
<212> TYPE: DNA
<213> ORGANISM: Artificial Sequence
<220> FEATURE:
<223> OTHER INFORMATION: PRIMER

<400> SEQUENCE: 6
gccaccgtac acgcctaccg ccc 23

<210> SEQ ID NO 7
<211> LENGTH: 1570
<212> TYPE: DNA

<213> ORGANISM: Artificial Sequence
<220> FEATURE:
<223> OTHER INFORMATION: NUCLEOTIDE SEQUENCE OF TRANSFER PLASMID CMVie
      EGFP EXPRESSION CASSETTE

<400> SEQUENCE: 7

```
ttattaatag taatcaatta cggggtcatt agttcatagc ccatatatgg agttccgcgt     60

tacataactt acggtaaatg gcccgcctgg ctgaccgccc aacgaccccc gcccattgac    120

gtcaataatg acgtatgttc ccatagtaac gccaataggg actttccatt gacgtcaatg    180

ggtggagtat ttacggtaaa ctgcccactt ggcagtacat caagtgtatc atatgccaag    240

tacgccccct attgacgtca atgacggtaa atggcccgcc tggcattatg cccagtacat    300

gaccttatgg gactttccta cttggcagta catctacgta ttagtcatcg ctattaccat    360

ggtgatgcgg ttttggcagt acatcaatgg gcgtggatag cggtttgact cacggggatt    420

tccaagtctc caccccattg acgtcaatgg gagtttgttt tggcaccaaa atcaacggga    480

ctttccaaaa tgtcgtaaca actccgcccc attgacgcaa atgggcggta ggcgtgtacg    540

gtggcggatc cgccgccacc atgggccgcc accatggtga gcaagggcga ggagctgttc    600

accggggtgg tgcccatcct ggtcgagctg gacggcgacg taaacggcca caagttcagc    660

gtgtccggcg agggcgaggg cgatgccacc tacggcaagc tgaccctgaa gttcatctgc    720

accaccggca agctgcccgt gccctggccc accctcgtga ccaccctgac ctacggcgtg    780

cagtgcttca gccgctaccc cgaccacatg aagcagcacg acttcttcaa gtccgccatg    840

cccgaaggct acgtccagga gcgcaccatc ttcttcaagg acgacggcaa ctacaagacc    900

cgcgccgagg tgaagttcga gggcgacacc ctggtgaacc gcatcgagct gaagggcatc    960

gacttcaagg aggacggcaa catcctgggg cacaagctgg agtacaacta caacagccac   1020

aacgtctata tcatggccga caagcagaag aacggcatca aggtgaactt caagatccgc   1080

cacaacatcg aggacggcag cgtgcagctc gccgaccact accagcagaa cacccccatc   1140

ggcgacggcc ccgtgctgct gcccgacaac cactacctga gcacccagtc cgccctgagc   1200

aaagacccca acgagaagcg cgatcacatg gtcctgctgg agttcgtgac cgccgccggg   1260

atcactctcg gcatggacga gctgtacaag taagtcgact atttcgagta cctctagggc   1320

cgcttcgagc agacatgata agatacattg atgagtttgg acaaaccaca actagaatgc   1380

agtgaaaaaa atgctttatt tgtgaaattt gtgatgctat tgctttattt gtaaccatta   1440

taagctgcaa taaacaagtt aacaacaaca attgcattca ttttatgttt caggttcagg   1500

gggagatgtg ggaggttttt taaagcaagt aaaacctcta caaatgtggt aaaatcgaat   1560

ctagatcctc                                                          1570
```

<210> SEQ ID NO 8
<211> LENGTH: 19
<212> TYPE: DNA
<213> ORGANISM: Artificial Sequence
<220> FEATURE:
<223> OTHER INFORMATION: PRIMER

<400> SEQUENCE: 8

```
gggcgaggag ctgttcacc                                                  19
```

<210> SEQ ID NO 9
<211> LENGTH: 21
<212> TYPE: DNA
<213> ORGANISM: Artificial Sequence
<220> FEATURE:

<223> OTHER INFORMATION: PRIMER

<400> SEQUENCE: 9
ccggcggcgg tcacgaactc c 21

<210> SEQ ID NO 10
<211> LENGTH: 3636
<212> TYPE: DNA
<213> ORGANISM: Artificial Sequence
<220> FEATURE:
<223> OTHER INFORMATION: NUCLEOTIDE SEQUENCE OF TRANSFER PLASMID CMVie
CPV VP2 (n) EXPRESSION CASSETTE

<400> SEQUENCE: 10
ccacgtggtt taaacctccc aaataggtat aaaaagccca gtgctggctg gcacgggcat 60
tcagcttagc gaagacatcc ccagcgcctc ctggatcagg cccgacggca tattccagct 120
aggagggggg tctcgctcgt ccttcagccc aacgcaagca ttcctcaccc tgcaacaggc 180
atcctcgacg ccgcgcgcag gaggcgtggg cacctaccag tttgtgcgcg aatttgtgcc 240
agaggtatac cttaaccctt tttcaggacc accggacacc tttcctgatc agttcattcc 300
taactacgac attgtaacca actctgtcga tggctatgac tgaggagagc atggaccagg 360
tggaggtgaa ctgcctgtgt gctcagcatg cccaaacctg cacgcgccct cgctgctttg 420
caaaggaggg tttatgtgct aactggtttt acaacccagc acttgccttt gaagggtttg 480
atattccaga ctcttaccaa gagggacacg gtgtggtacc tagttattaa tagtaatcaa 540
ttacggggtc attagttcat agcccatata tggagttccg cgttacataa cttacggtaa 600
atggcccgcc tggctgaccg cccaacgacc cccgcccatt gacgtcaata atgacgtatg 660
ttcccatagt aacgccaata gggactttcc attgacgtca atgggtggag tatttacggt 720
aaactgccca cttggcagta catcaagtgt atcatatgcc aagtacgccc cctattgacg 780
tcaatgacgg taaatggccc gcctggcatt atgcccagta catgacctta tgggactttc 840
ctacttggca gtacatctac gtattagtca tcgctattac catggtgatg cggttttggc 900
agtacatcaa tgggcgtgga tagcggtttg actcacgggg atttccaagt ctccacccca 960
ttgacgtcaa tgggagtttg ttttggcacc aaaatcaacg ggactttcca aaatgtcgta 1020
acaactccgc cccattgacg caaatgggcg gtaggcgtgt acggtggcgg atccgccgcc 1080
accatgagtg atggagcagt tcaaccagac ggtggtcaac ctgctgtcag aaatgaaaga 1140
gctacaggat ctgggaacgg gtctggaggc gggggtggtg gtggttctgg gggtgtgggg 1200
atttctacgg gtactttcaa taatcagacg gaatttaaat ttttggaaaa cggatgggtg 1260
gaaatcacag caaactcaag cagacttgta catttaaata tgccagaaag tgaaaattat 1320
agaagagtgg ttgtaaataa tttggataaa actgcagtta acggaaacat ggctttagat 1380
gatactcatg cacaaattgt aacaccttgg tcattggttg atgcaaatgc ttggggagtt 1440
tggtttaatc caggagattg gcaactaatt gttaatacta tgagtgagtt gcatttagtt 1500
agttttgaac aagaaatttt taatgttgtt ttaaagactg tttcagaatc tgctactcag 1560
ccaccaacta aagtttataa taatgattta actgcatcat tgatggttgc attagatagt 1620
aataatacta tgccatttac tccagcagct atgagatctg agacattggg tttttatcca 1680
tggaaaccaa ccataccaac tccatggaga tattattttc aatgggatag aacattaata 1740
ccatctcata ctggaactag tggcacacca acaaatatat accatggtac agatccagat 1800
gatgttcaat tttatactat tgaaaattct gtgccagtac acttactaag aacaggtgat 1860

-continued

```
gaatttgcta caggaacatt tttttttgat tgtaaaccat gtagactaac acatacatgg   1920

caaacaaata gagcattggg cttaccacca tttctaaatt ctttgcctca agctgaagga   1980

ggtactaact ttggttatat aggagttcaa caagataaaa gacgtggtgt aactcaaatg   2040

ggaaaaacaa actatattac tgaagctact attatgagac cagctgaggt tggttatagt   2100

gcaccatatt attcttttga ggcgtctaca caagggccat ttaaaacacc tattgcagca   2160

ggacgggggg gagcgcaaac agatgaaaat caaggagcag atggtaatcc aagatatgca   2220

tttggtagac aacatggtca aaaaactacc acaacaggag aaacacctga gagatttaca   2280

tatatagcac atcaagatac aggaagatat ccagaaggag attggattca aaatattaac   2340

tttaaccttc ctgtaacaga tgataatgta ttgctaccaa cagatccaat tggaggtaaa   2400

acaggaatta actatactaa tatatttaat acttatggtc ctttaactgc attaaataat   2460

gtaccaccag tttatccaaa tggtcaaatt tgggataaag aatttgatac tgacttaaaa   2520

ccaagacttc atgtaaatgc accatttgtt tgtcaaaata attgtcctgg tcaattattt   2580

gtaaaagttg cgcctaattt aacaaatgaa tatgatcctg atgcatctgc taatatgtca   2640

agaattgtaa cttactcaga tttttggtgg aaaggtaaat tagtatttaa agctaaacta   2700

agagcctctc atacttggaa tccaattcaa caaatgagta ttaatgtaga taaccaattt   2760

aactatgtac caagtaatat tggaggtatg gaaattgtat ttgaaagatc tcaactagca   2820

cctagaaaat tatattaagt cgactatttc gagtacctct agggccgctt cgagcagaca   2880

tgataagata cattgatgag tttggacaaa ccacaactag aatgcagtga aaaaaatgct   2940

ttatttgtga aatttgtgat gctattgctt tatttgtaac cattataagc tgcaataaac   3000

aagttaacaa caacaattgc attcatttta tgtttcaggt tcagggggag atgtgggagg   3060

tttttaaag caagtaaaac ctctacaaat gtggtaaaat cgaatctaga tcctccttaa   3120

gacaccctca gccttctaat gggactaaac aacaaaaatc aggcccatgt agcttgtcaa   3180

ataaacttac ctaatttttg ctaagacgtc tgggtcctgc gtttctatgt ccaccaaagt   3240

cccctcttcc cagctttggt acttccactt gtgcgcgcga gccagcttgc ggatgtgctt   3300

gaaagataat gtggtctctc ccaacagctt cccgttcacc agcaccaggg ccatgaagcg   3360

gacacgaaga gctctacctg caaattatga ccctgtatat ccatacgacg cccccgggtc   3420

ttccacacaa cccccttttt ttaataacaa gcaaggtctc actgagtcac ccccaggaac   3480

cctggctgtc aatgtttccc ctccactaac cttttctacg ttaggtgcca ttaaactttc   3540

cacaggtccc ggactcaccc tcaacgaggg caagttacaa gccagcttag ggcccggcct   3600

catcacaaat accgagggcc aaatcactgt tggttt                             3636
```

<210> SEQ ID NO 11
<211> LENGTH: 28
<212> TYPE: DNA
<213> ORGANISM: Artificial Sequence
<220> FEATURE:
<223> OTHER INFORMATION: PRIMER

<400> SEQUENCE: 11

```
tgatcagttc attcctaact acgacatt                                       28
```

<210> SEQ ID NO 12
<211> LENGTH: 22
<212> TYPE: DNA
<213> ORGANISM: Artificial Sequence
<220> FEATURE:
<223> OTHER INFORMATION: PRIMER

<400> SEQUENCE: 12
ttgctatcta atgcaaccat ca 22

<210> SEQ ID NO 13
<211> LENGTH: 20
<212> TYPE: DNA
<213> ORGANISM: Artificial Sequence
<220> FEATURE:
<223> OTHER INFORMATION: PRIMER

<400> SEQUENCE: 13
aatgcaccat ttgtttgtca 20

<210> SEQ ID NO 14
<211> LENGTH: 21
<212> TYPE: DNA
<213> ORGANISM: Artificial Sequence
<220> FEATURE:
<223> OTHER INFORMATION: PRIMER

<400> SEQUENCE: 14
gggaagctgt tgggagagac c 21

<210> SEQ ID NO 15
<211> LENGTH: 19
<212> TYPE: DNA
<213> ORGANISM: Artificial Sequence
<220> FEATURE:
<223> OTHER INFORMATION: PRIMER

<400> SEQUENCE: 15
aatgcttggg gagtttggt 19

<210> SEQ ID NO 16
<211> LENGTH: 20
<212> TYPE: DNA
<213> ORGANISM: Artificial Sequence
<220> FEATURE:
<223> OTHER INFORMATION: PRIMER

<400> SEQUENCE: 16
ttgtgtagac gcctcaaaag 20

<210> SEQ ID NO 17
<211> LENGTH: 19
<212> TYPE: DNA
<213> ORGANISM: Artificial Sequence
<220> FEATURE:
<223> OTHER INFORMATION: PRIMER

<400> SEQUENCE: 17
aatgcttggg gagtttggt 19

<210> SEQ ID NO 18
<211> LENGTH: 22
<212> TYPE: DNA
<213> ORGANISM: Artificial Sequence
<220> FEATURE:
<223> OTHER INFORMATION: PRIMER

<400> SEQUENCE: 18
tgcatcagga tcatattcat tt 22

<210> SEQ ID NO 19

<211> LENGTH: 23
<212> TYPE: DNA
<213> ORGANISM: Artificial Sequence
<220> FEATURE:
<223> OTHER INFORMATION: PRIMER
<400> SEQUENCE: 19
aactcaaatg ggaaatacaa act 23

<210> SEQ ID NO 20
<211> LENGTH: 22
<212> TYPE: DNA
<213> ORGANISM: Artificial Sequence
<220> FEATURE:
<223> OTHER INFORMATION: PRIMER
<400> SEQUENCE: 20
tgcatcagga tcatattcat tt 22

<210> SEQ ID NO 21
<211> LENGTH: 28
<212> TYPE: DNA
<213> ORGANISM: Artificial Sequence
<220> FEATURE:
<223> OTHER INFORMATION: PRIMER
<400> SEQUENCE: 21
tgatcagttc attcctaact acgacatt 28

<210> SEQ ID NO 22
<211> LENGTH: 21
<212> TYPE: DNA
<213> ORGANISM: Artificial Sequence
<220> FEATURE:
<223> OTHER INFORMATION: PRIMER
<400> SEQUENCE: 22
gggaagctgt tgggagagac c 21

<210> SEQ ID NO 23
<211> LENGTH: 2563
<212> TYPE: DNA
<213> ORGANISM: Artificial Sequence
<220> FEATURE:
<223> OTHER INFORMATION: NUCLEOTIDE SEQUENCE OF TRANSFER PLASMID CMVie
      CPV VP2 (co) EXPRESSION CASSETTE <400> SEQUENCE: 23
ttattaatag taatcaatta cggggtcatt agttcatagc ccatatatgg agttccgcgt 60
tacataactt acggtaaatg gcccgcctgg ctgaccgccc aacgaccccc gcccattgac 120
gtcaataatg acgtatgttc ccatagtaac gccaataggg actttccatt gacgtcaatg 180
ggtggagtat ttacggtaaa ctgcccactt ggcagtacat caagtgtatc atatgccaag 240
tacgccccct attgacgtca atgacggtaa atggcccgcc tggcattatg cccagtacat 300
gaccttatgg gactttccta cttggcagta catctacgta ttagtcatcg ctattaccat 360
ggtgatgcgg ttttggcagt acatcaatgg gcgtggatag cggtttgact cacggggatt 420
tccaagtctc caccccattg acgtcaatgg gagtttgttt tggcaccaaa atcaacggga 480
ctttccaaaa tgtcgtaaca actccgcccc attgacgcaa atgggcggta ggcgtgtacg 540
gtggcggatc cgccgccacc atgtctgatg gcgccgtgca gcctgatggc ggacagcctg 600
ctgtgcggaa tgagagagcc accggcagcg gcaatggatc tggcggaggc ggcggagggg 660

-continued

```
gaagtggcgg agtgggaatt agcaccggca ccttcaacaa ccagaccgag ttcaagttcc     720

tggaaaacgg ctgggtggaa atcaccgcca acagcagcag actggtgcac ctgaacatgc     780

ccgagagcga gaactaccgg cgggtggtcg tgaacaacct ggacaagacc gccgtgaacg     840

gcaacatggc cctggacgat acccacgccc agatcgtgac accctggtcc ctggtggatg     900

ccaatgcctg ggcgtgtgg ttcaaccccg gcgactggca gctgatcgtg aacaccatga     960

gcgagctgca cctggtgtcc ttcgagcagg aaatcttcaa cgtggtgctg aaaaccgtgt    1020

ccgagagcgc cacacagccc cccaccaagg tgtacaacaa cgacctgacc gcctccctga    1080

tggtggctct ggacagcaac aacaccatgc ccttcacccc tgccgccatg cggagcgaga    1140

cactgggctt ctacccctgg aagcccacca tccctacccc ctggcggtac tacttccagt    1200

gggacagaac cctgatcccc agccacacag gcaccagcgg caccccctacc aacatctacc   1260

acggcaccga ccccgacgac gtgcagttct acaccatcga gaacagcgtg cccgtgcatc    1320

tgctgagaac cggcgacgag ttcgccacag gcacattctt tttcgactgc aaaccctgcc    1380

ggctgaccca cacctggcag accaatagag ccctgggcct gcccccattc ctgaacagtc    1440

tgcctcaggc cgagggcggc accaactttg gctatatcgg cgtgcagcag gacaagcgga    1500

gaggcgtgac acagatgggc aagaccaact acatcaccga ggccacaatc atgcggcctg    1560

ccgaagtggg ctacagcgcc ccctactaca gcttcgaggc cagcacccag ggccccttca    1620

agacacctat tgccgccgga agaggcggag cccagaccga tgagaatcag ggcgccgacg    1680

gcaaccccag atacgccttt ggcagacagc acggccagaa aaccaccacc accggcgaga    1740

cacccgagcg gttcacctat atcgcccacc aggacaccgg cagataccccc gagggcgact   1800

ggattcagaa catcaacttc aacctgcccg tgaccgacga caacgtgctg ctgcccacag    1860

atcccatcgg cggcaagacc ggcatcaact acaccaatat cttcaacacc tacggccctc    1920

tgaccgccct gaacaacgtg ccccccgtgt accccaacgg acagatctgg gacaaagagt    1980

tcgacaccga cctgaagccc cggctgcatg tgaacgcccc tttcgtgtgc cagaacaact    2040

gccctggcca gctgtttgtg aaggtggccc ccaacctgac caacgagtac gaccctgacg    2100

ccagcgccaa catgagccgg atcgtgacct acagcgactt ctggtggaag ggcaagctgg    2160

tgttcaaggc caagctgcgg gcctctcaca cctggaaccc catccagcag atgagcatca    2220

acgtggacaa ccagttcaac tacgtgccca gcaacatcgg cggaatggaa atcgtgttcg    2280

agcggtccca gctggccccc agaaagctgt actaatctag agggccctat tctatagtgt    2340

cacctaaatg ctagagctcg ctgatcagcc tcgactgtgc cttctagttg ccagccatct    2400

gttgtttgcc cctcccccgt gccttccttg accctggaag gtgccactcc cactgtcctt    2460

tcctaataaa atgaggaaat tgcatcgcat tgtctgagta ggtgtcattc tattctgggg    2520

ggtggggtgg ggcaggacag caagggggag gattgggaag aca                      2563
```

<210> SEQ ID NO 24
<211> LENGTH: 584
<212> TYPE: PRT
<213> ORGANISM: canine parvovirus

<400> SEQUENCE: 24

```
Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
```

-continued

```
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
    210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
            260                 265                 270

Cys Arg Leu Thr His Thr Trp Gln Thr Asn Arg Ala Leu Gly Leu Pro
        275                 280                 285

Pro Phe Leu Asn Ser Leu Pro Gln Ala Glu Gly Gly Thr Asn Phe Gly
    290                 295                 300

Tyr Ile Gly Val Gln Gln Asp Lys Arg Arg Gly Val Thr Gln Met Gly
305                 310                 315                 320

Lys Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Gly Ala Asp Gly Asn Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Thr Asp Asp Asn Val Leu Leu Pro
            420                 425                 430

Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460
```

```
Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Glu Ile Val Phe Glu Arg Ser
                565                 570                 575

Gln Leu Ala Pro Arg Lys Leu Tyr
            580


<210> SEQ ID NO 25
<211> LENGTH: 2418
<212> TYPE: DNA
<213> ORGANISM: Artificial Sequence
<220> FEATURE:
<223> OTHER INFORMATION: NUCLEOTIDE SEQUENCE OF TRANSFER PLASMID CMVie
      RabGP (n) EXPRESSION CASSETTE

<400> SEQUENCE: 25

ttattaatag taatcaatta cggggtcatt agttcatagc ccatatatgg agttccgcgt      60

tacataactt acggtaaatg gcccgcctgg ctgaccgccc aacgaccccc gcccattgac     120

gtcaataatg acgtatgttc ccatagtaac gccaataggg actttccatt gacgtcaatg     180

ggtggagtat ttacggtaaa ctgcccactt ggcagtacat caagtgtatc atatgccaag     240

tacgccccct attgacgtca atgacggtaa atggcccgcc tggcattatg cccagtacat     300

gaccttatgg gactttccta cttggcagta catctacgta ttagtcatcg ctattaccat     360

ggtgatgcgg ttttggcagt acatcaatgg gcgtggatag cggtttgact cacggggatt     420

tccaagtctc caccccattg acgtcaatgg gagtttgttt tggcaccaaa atcaacggga     480

ctttccaaaa tgtcgtaaca actccgcccc attgacgcaa atgggcggta ggcgtgtacg     540

gtggcggatc cgccgccacc atggtaccgg ttcctcaggc tctcctgttt gtaccccttc     600

tggtttttcc attgtgtttt gggaaattcc ctatttacac gataccagac aagcttggtc     660

cctggagccc gattgacata catcacctca gctgcccaaa caatttggta gtggaggacg     720

aaggatgcac caacctgtca gggttctcct acatggaact taaagttgga tacatctcag     780

ccataaaaat gaacgggttc acttgcacag gcgttgtgac ggaggctgaa acctacacta     840

acttcgttgg ttatgtcaca accacgttca aaagaaagca tttccgccca acaccagatg     900

catgtagagc cgcgtacaac tggaagatgg ccggtgaccc cagatatgaa gagtctctac     960

acaatccgta ccctgactac cactggcttc gaactgtaaa aaccaccaag gagtctctcg    1020

ttatcatatc tccaagtgtg gcagatttgg acccatatga cagatccctt cactcgaggg    1080

tcttccctgg cgggaagtgc tcaggagtag cggtgtcttc tacctactgc tccactaacc    1140

acgattacac catttggatg cccgagaatc cgagactagg gatgtcttgt gacattttta    1200

ccaatagtag agggaagaga gcatccaaag ggagtgagac ttgcggcttt gtagatgaaa    1260

gaggcctata taagtcttta aaaggagcat gcaaactcaa gttatgtgga gttctcggac    1320
```

```
ttagacttat ggatggaaca tgggtctcga tgcaaacatc aaatgaaacc aaatggtgcc   1380

ctcccggtca gttgatcaat ttgcacgact ttcgctcaga cgaaattgag caccttgttg   1440

tagaggagtt ggtcaagaag agagaggagt gtctggatgc actagagtcc atcatgacca   1500

ccaagtcagt aagtttcaga cgtctcagtc atttaagaaa acttgtccct gggtttggaa   1560

aagcatatac catattcaac aagaccttga tggaagccga tgctcactac aagtcagtca   1620

gaacttggaa tgagatcatc ccttcaaaag ggtgtttaag agttgggggg aggtgtcatc   1680

ctcatgtaaa cggggtattt ttcaatggta taatattagg acctgacggc aatgtcttaa   1740

tcccagagat gcaatcatcc ctcctccagc aacatatgga gttgttggta tcctcggtta   1800

tccccttat gcaccccctg gcagacccgt ctaccgtttt caagaacggt gacgaggctg   1860

aggattttgt tgaagttcac cttcccgatg tgcacgaacg gatctcagga gttgacttgg   1920

gtctcccgaa ctgggggaag tatgtattac tgagtgcagg ggccctgact gccttgatgt   1980

tgataatttt cctgatgaca tgctggagaa gagtcaatcg atcggaacct acacaacaca   2040

atctcagagg gacagggagg gaggtgtcag tcactcccca aagcgggaag atcatatctt   2100

catgggaatc atacaagagc gggggtgaga ccggactgtg agtcgactat ttcgagtacc   2160

tctagggccg cttcgagcag acatgataag atacattgat gagtttggac aaaccacaac   2220

tagaatgcag tgaaaaaaat gctttatttg tgaaatttgt gatgctattg ctttatttgt   2280

aaccattata agctgcaata aacaagttaa caacaacaat tgcattcatt ttatgtttca   2340

ggttcagggg gagatgtggg aggtttttta aagcaagtaa aacctctaca aatgtggtaa   2400

aatcgaatct agatcctc                                                 2418
```

<210> SEQ ID NO 26
<211> LENGTH: 526
<212> TYPE: PRT
<213> ORGANISM: Rabies virus

<400> SEQUENCE: 26

```
Met Val Pro Val Pro Gln Ala Leu Leu Phe Val Pro Leu Leu Val Phe
1               5                   10                  15

Pro Leu Cys Phe Gly Lys Phe Pro Ile Tyr Thr Ile Pro Asp Lys Leu
            20                  25                  30

Gly Pro Trp Ser Pro Ile Asp Ile His His Leu Ser Cys Pro Asn Asn
        35                  40                  45

Leu Val Val Glu Asp Glu Gly Cys Thr Asn Leu Ser Gly Phe Ser Tyr
    50                  55                  60

Met Glu Leu Lys Val Gly Tyr Ile Ser Ala Ile Lys Met Asn Gly Phe
65                  70                  75                  80

Thr Cys Thr Gly Val Val Thr Glu Ala Glu Thr Tyr Thr Asn Phe Val
                85                  90                  95

Gly Tyr Val Thr Thr Thr Phe Lys Arg Lys His Phe Arg Pro Thr Pro
            100                 105                 110

Asp Ala Cys Arg Ala Ala Tyr Asn Trp Lys Met Ala Gly Asp Pro Arg
        115                 120                 125

Tyr Glu Glu Ser Leu His Asn Pro Tyr Pro Asp Tyr His Trp Leu Arg
    130                 135                 140

Thr Val Lys Thr Thr Lys Glu Ser Leu Val Ile Ile Ser Pro Ser Val
145                 150                 155                 160

Ala Asp Leu Asp Pro Tyr Asp Arg Ser Leu His Ser Arg Val Phe Pro
                165                 170                 175
```

-continued

```
Gly Gly Lys Cys Ser Gly Val Ala Val Ser Ser Thr Tyr Cys Ser Thr
            180                 185                 190

Asn His Asp Tyr Thr Ile Trp Met Pro Glu Asn Pro Arg Leu Gly Met
        195                 200                 205

Ser Cys Asp Ile Phe Thr Asn Ser Arg Gly Lys Arg Ala Ser Lys Gly
    210                 215                 220

Ser Glu Thr Cys Gly Phe Val Asp Glu Arg Gly Leu Tyr Lys Ser Leu
225                 230                 235                 240

Lys Gly Ala Cys Lys Leu Lys Leu Cys Gly Val Leu Gly Leu Arg Leu
                245                 250                 255

Met Asp Gly Thr Trp Val Ser Met Gln Thr Ser Asn Glu Thr Lys Trp
            260                 265                 270

Cys Pro Pro Gly Gln Leu Ile Asn Leu His Asp Phe Arg Ser Asp Glu
        275                 280                 285

Ile Glu His Leu Val Val Glu Glu Leu Val Lys Lys Arg Glu Glu Cys
    290                 295                 300

Leu Asp Ala Leu Glu Ser Ile Met Thr Thr Lys Ser Val Ser Phe Arg
305                 310                 315                 320

Arg Leu Ser His Leu Arg Lys Leu Val Pro Gly Phe Gly Lys Ala Tyr
                325                 330                 335

Thr Ile Phe Asn Lys Thr Leu Met Glu Ala Asp Ala His Tyr Lys Ser
            340                 345                 350

Val Arg Thr Trp Asn Glu Ile Ile Pro Ser Lys Gly Cys Leu Arg Val
        355                 360                 365

Gly Gly Arg Cys His Pro His Val Asn Gly Val Phe Phe Asn Gly Ile
    370                 375                 380

Ile Leu Gly Pro Asp Gly Asn Val Leu Ile Pro Glu Met Gln Ser Ser
385                 390                 395                 400

Leu Leu Gln Gln His Met Glu Leu Leu Val Ser Ser Val Ile Pro Leu
                405                 410                 415

Met His Pro Leu Ala Asp Pro Ser Thr Val Phe Lys Asn Gly Asp Glu
            420                 425                 430

Ala Glu Asp Phe Val Glu Val His Leu Pro Asp Val His Glu Arg Ile
        435                 440                 445

Ser Gly Val Asp Leu Gly Leu Pro Asn Trp Gly Lys Tyr Val Leu Leu
    450                 455                 460

Ser Ala Gly Ala Leu Thr Ala Leu Met Leu Ile Ile Phe Leu Met Thr
465                 470                 475                 480

Cys Trp Arg Arg Val Asn Arg Ser Glu Pro Thr Gln His Asn Leu Arg
                485                 490                 495

Gly Thr Gly Arg Glu Val Ser Val Thr Pro Gln Ser Gly Lys Ile Ile
            500                 505                 510

Ser Ser Trp Glu Ser Tyr Lys Ser Gly Gly Glu Thr Gly Leu
        515                 520                 525
```

<210> SEQ ID NO 27
<211> LENGTH: 3546
<212> TYPE: DNA
<213> ORGANISM: Artificial Sequence
<220> FEATURE:
<223> OTHER INFORMATION: NUCLEOTIDE SEQUENCE OF TRANSFER PLASMID CMVie
BRSV F (co) EXPRESSION CASSETTE

<400> SEQUENCE: 27
tcagcttagc gaagacatcc ccagcgcctc ctggatcagg cccgacggca tattccagct 60

-continued

```
aggaggggg tctcgctcgt ccttcagccc aacgcaagca ttcctcaccc tgcaacaggc    120
atcctcgacg ccgcgcgcag gaggcgtggg cacctaccag tttgtgcgcg aatttgtgcc    180
agaggtatac cttaaccctt tttcaggacc accggacacc tttcctgatc agttcattcc    240
taactacgac attgtaacca actctgtcga tggctatgac tgaggagagc atggaccagg    300
tggaggtgaa ctgcctgtgt gctcagcatg cccaaacctg cacgcgccct cgctgctttg    360
caaaggaggg tttatgtgct aactggtttt acaacccagc acttgccttt gaagggtttg    420
atattccaga ctcttaccaa gagggacacg gtgtggtacc tagttattaa tagtaatcaa    480
ttacggggtc attagttcat agcccatata tggagttccg cgttacataa cttacggtaa    540
atggcccgcc tggctgaccg cccaacgacc cccgcccatt gacgtcaata atgacgtatg    600
ttcccatagt aacgccaata gggactttcc attgacgtca atgggtggag tatttacggt    660
aaactgccca cttggcagta catcaagtgt atcatatgcc aagtacgccc cctattgacg    720
tcaatgacgg taaatggccc gcctggcatt atgcccagta catgacctta tgggactttc    780
ctacttggca gtacatctac gtattagtca tcgctattac catggtgatg cggttttggc    840
agtacatcaa tgggcgtgga tagcggtttg actcacgggg atttccaagt ctccacccca    900
ttgacgtcaa tgggagtttg ttttggcacc aaaatcaacg ggactttcca aaatgtcgta    960
acaactccgc cccattgacg caaatgggcg gtaggcgtgt acggtggcgg atccgccgcc   1020
accatggcca ccaccgccat gaggatgatc atcagcatca tcttcatcag cacctacgtg   1080
acccacatca ccctgtgcca gaacatcacc gaggaattct accagagcac ctgtagcgcc   1140
gtgtccaggg gctacctgag cgccctgaga accggctggt acaccagcgt ggtgacaatc   1200
gagctgagca agatccagaa aaacgtgtgc aacagcaccg acagcaaagt gaagctgatc   1260
aagcaagaac tgggccgcta caacaacgcc gtgattgaac tgcagagcct gatgcagaac   1320
gagcccgcca gcttcagcag ggccaagagg ggcatccccg agctgatcca ctaccccaga   1380
aacagcacca agaggttcta cggcctgatg ggcaagaaga ggaagcgcag attcctgggc   1440
ttcctgctgg gcatcggcag cgccatcgct tctggcgtgg ccgtgtctaa ggtgctgcac   1500
ctggaaggcg aagtgaacaa gatcaagaac gccctgctga gcaccaacaa ggctgtggtg   1560
tccctgagca acggcgtgtc cgtgctgacc agcaaggtgc tggatctgaa gaactacatc   1620
gacaaaaagc tgctgcccaa ggtcaacaac cacgactgca ggatcagcaa catcgagaca   1680
gtgatcgagt tccagcagaa gaacaacagg ctgctggaaa tcgcccgcga gttcagcgtg   1740
aacgccggca tcaccacccc cctgagcacc tacatgctga ccaacagcga gctgctgagc   1800
ctgatcaacg acatgcccat caccaacgac cagaaaaagc tgatgagcag caacgtgcag   1860
atcgtgcgcc agcagagcta cagcatcatg agcgtggtga aagaagaagt cattgcctac   1920
gtcgtgcagc tgcccatcta cggcgtgatc gacacccccct gctggaaggt gcacaccagc   1980
cctctgtgca caaccgacaa caaagagggc agcaacatct gcctgaccag gaccgacagg   2040
ggctggtact gcgacaacgc cggctccgtg tcattctttc cacaagccga aacatgcaag   2100
gtgcagagca acagggtgtt ctgcgacacc atgaacagcc tgaccctgcc caccgacgtg   2160
aacctgtgca acaccgatat cttcaacacc aaatacgatt gcaagatcat gacctccaag   2220
accgacatca gcagcagcgt gatcaccagc atcggcgcca tcgtgtcctg ctacggcaag   2280
accaagtgca ccgccagcaa caagaacagg ggcatcatca agaccttcag caacggctgc   2340
gactacgtgt ccaacaaggg cgtggacacc gtgtccgtgg gcaacaccct gtactacgtg   2400
```

-continued

```
aacaagctgg aaggcaaggc cctgtacatc aagggcgagc ccatcatcaa ctactacgac   2460

cccctggtgt tccccagcga cgagttcgac gcctctatcg ctcaggtcaa cgccaagatc   2520

aaccagagcc tggccttcat caggcgcagc gacgagctgc tgcacagcgt ggacgtgggc   2580

aagtccacca tcaacgtggt gatcacaacc atcatcatcg tgatcgtggt ggtgatcctg   2640

atgctgatcg ccgtgggcct gctgttctac tgcaagacaa ggtccacccc catcatgctg   2700

ggcaaggacc agctgagcgg catcaacaac ctgagcttct ctaaataagt cgactatttc   2760

gagtacctct agggccgctt cgagcagaca tgataagata cattgatgag tttggacaaa   2820

ccacaactag aatgcagtga aaaaaatgct ttatttgtga aatttgtgat gctattgctt   2880

tatttgtaac cattataagc tgcaataaac aagttaacaa caacaattgc attcatttta   2940

tgtttcaggt tcagggggag atgtgggagg tttttaaag caagtaaaac ctctacaaat   3000

gtggtaaaat cgaatctaga tcctccttaa gacaccctca gccttctaat gggactaaac   3060

aacaaaaatc aggcccatgt agcttgtcaa ataaacttac ctaatttttg ctaagacgtc   3120

tgggtcctgc gtttctatgt ccaccaaagt cccctcttcc cagctttggt acttccactt   3180

gtgcgcgcga gccagcttgc ggatgtgctt gaaagataat gtggtctctc ccaacagctt   3240

cccgttcacc agcaccaggg ccatgaagcg gacacgaaga gctctacctg caaattatga   3300

ccctgtatat ccatacgacg cccccgggtc ttccacacaa cccccttttt ttaataacaa   3360

gcaaggtctc actgagtcac ccccaggaac cctggctgtc aatgtttccc ctccactaac   3420

cttttctacg ttaggtgcca ttaaactttc cacaggtccc ggactcaccc tcaacgaggg   3480

caagttacaa gccagcttag ggcccggcct catcacaaat accgagggcc aaatcactgt   3540

tggttt                                                              3546
```

```
<210> SEQ ID NO 28
<211> LENGTH: 574
<212> TYPE: PRT
<213> ORGANISM: Bovine respiratory syncytial virus

<400> SEQUENCE: 28

Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Asn Ser Thr Asp Ser Lys Val Lys Leu Ile Lys
65                  70                  75                  80

Gln Glu Leu Gly Arg Tyr Asn Asn Ala Val Ile Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Pro Arg Asn Ser Thr Lys Arg Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
```

-continued

```
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Lys Leu Leu Pro Lys Val Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Val His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Ile Asn Val Val Ile Thr
        515                 520                 525

Thr Ile Ile Ile Val Ile Val Val Val Ile Leu Met Leu Ile Ala Val
    530                 535                 540

Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
                565                 570
```

<210> SEQ ID NO 29

<211> LENGTH: 600
<212> TYPE: DNA
<213> ORGANISM: Equine herpesvirus 4

<400> SEQUENCE: 29

```
gcagactttg gagcagcaca atttccggtt gtggacccca tggaccttgg tttggctggt      60

accgtggaaa ctaacgctcc ggaagttttg gccagagcaa aatacaattc gaaggtagac     120

atatggagcg ccggaatagt tctgtttgaa atgctcgcat atccatcaac tctatttgag     180

gacccgccga gtaccccaca agagtatgta aaaagctgtc attctcaact actgagaata     240

atatcaaagc taaagataaa ccctgaggag tttccacggg aaccagagtc taggctcgtg     300

cgcggataca tcgaatacgc cagcctagag cgtaagccac atacgcgcta tccttgcttc     360

cagcgcgtga acctacacat tgacggggaa tttttgatcc ataaaatgct agcgttcaat     420

gctgcgatgc gcccatccgc agaagagttg ttgtcctacc caatgtttat gaatctgtag     480

gatgactaac agatttgggg tggagacggc gtgggcgata ctgtataaag ttgtactact     540

taccagccca gtcagtgtgc tgtagtgcca ccacctgtaa agctgtgata agctgcagtt     600
```

<210> SEQ ID NO 30
<211> LENGTH: 600
<212> TYPE: DNA
<213> ORGANISM: Equine herpesvirus 4

<400> SEQUENCE: 30

```
agctggggga gtttgtacta tagtgtatta catgcggctt gcaataactg cctggtttat      60

gtttcgcaac attcaagcag acatgctacc gctaaacact ttgcaacaat tttttattgg     120

gtgtttggcc tttggtagaa ctgtcgcgtt tttggtggta gcatatacta ccttatttat     180

acgctccgag ctgtttttca gcatgctagc acccaacgcc gagcgagagt atataactcc     240

catcattgcc cacaagctta tgccacttat tagcgtccgc tctgccgttt gcttagtcat     300

aatatctacc gccgtttacg cagcagacgc tatctgcgac acaattggat ttgcgatacc     360

gcgcatgtgg atgtgtattt taatgagatc aacctccatg aagcgtaact agggggcctc     420

ccactgaggc actaccggct tagcagctga ctaacacagt ataaaacgtg agaagaaatc     480

agtctcatgc gccattagcg ctaggctagt tagcgtggag gaccggagcg ctaccgccag     540

cagtttcatc cgcctggtta cgggtttgtt aacacctacc ggtgttttac cgctaccata     600
```

<210> SEQ ID NO 31
<211> LENGTH: 442
<212> TYPE: DNA
<213> ORGANISM: Equine herpesvirus 4

<400> SEQUENCE: 31

```
ggtacctcta tttgaggacc cgccgagtac cccacaagag tatgtaaaaa gctgtcattc      60

tcaactactg agaataatat caaagctaaa gataaaccct gaggagtttc cacgggaacc     120

agagtctagg ctcgtgcgcg gatacatcga atacgccagc ctagagcgta agccacatac     180

gcgctatcct tgcttccagc gcgtgaacct acacattgac ggggaatttt tgatccataa     240

aatgctagcg ttcaatgctg cgatgcgccc atccgcagaa gagttgttgt cctacccaat     300

gtttatgaat ctgtaggatg actaacagat ttggggtgga gacggcgtgg gcgatactgt     360

ataaagttgt actacttacc agcccagtca gtgtgctgta gtgccaccac ctgtaaagct     420

gtgataagct gcagttggat cc                                              442
```

-continued

<210> SEQ ID NO 32
<211> LENGTH: 467
<212> TYPE: DNA
<213> ORGANISM: Equine herpesvirus 4

<400> SEQUENCE: 32
ggtaccactg gtggtagcat atactacctt atttatacgc tccgagctgt ttttcagcat 60
gctagcaccc aacgccgagc gagagtatat aactcccatc attgcccaca agcttatgcc 120
acttattagc gtccgctctg ccgtttgctt agtcataata tctaccgccg tttacgcagc 180
agacgctatc tgcgacacaa ttggatttgc gataccgcgc atgtggatgt gtattttaat 240
gagatcaacc tccatgaagc gtaactaggg ggcctcccac tgaggcacta ccggcttagc 300
agctgactaa cacagtataa aacgtgagaa gaaatcagtc tcatgcgcca ttagcgctag 360
gctagttagc gtggaggacc ggagcgctac cgccagcagt ttcatccgcc tggttacggg 420
tttgttaaca cctaccggtg ttttaccgct accataggat cggatcc 467

<210> SEQ ID NO 33
<211> LENGTH: 37
<212> TYPE: DNA
<213> ORGANISM: Artificial Sequence
<220> FEATURE:
<223> OTHER INFORMATION: PRIMER

<400> SEQUENCE: 33
tttaaaggta cctctatttg aggacccgcc gagtacc 37

<210> SEQ ID NO 34
<211> LENGTH: 42
<212> TYPE: DNA
<213> ORGANISM: Artificial Sequence
<220> FEATURE:
<223> OTHER INFORMATION: PRIMER

<400> SEQUENCE: 34
aaatttggat ccaactgcag cttatcacag ctttacaggt gg 42

<210> SEQ ID NO 35
<211> LENGTH: 47
<212> TYPE: DNA
<213> ORGANISM: Artificial Sequence
<220> FEATURE:
<223> OTHER INFORMATION: PRIMER

<400> SEQUENCE: 35
tttaaaggta ccactggtgg tagcatatac tacctttatt tatacgc 47

<210> SEQ ID NO 36
<211> LENGTH: 38
<212> TYPE: DNA
<213> ORGANISM: Artificial Sequence
<220> FEATURE:
<223> OTHER INFORMATION: PRIMER

<400> SEQUENCE: 36
aaatttggat ccgatcctat ggtagcggta aaacaccg 38

<210> SEQ ID NO 37
<211> LENGTH: 1776
<212> TYPE: DNA
<213> ORGANISM: Artificial Sequence
<220> FEATURE:
<223> OTHER INFORMATION: CPV VP2 Despliced ORF with BamHI and SalI
Restriction Endonuclease Sites

<400> SEQUENCE: 37

```
ggatccgccg ccaccatgtc tgatggcgcc gtgcagcctg atggcggaca gcctgccgtc     60
cggaatgaga gagccaccgg cagcggcaat ggatctggcg gaggcggcgg aggcggaagt    120
ggcggcgtcg gcattagcac cggcaccttc aacaaccaga ccgagttcaa gttcctggaa    180
aacggctggg tcgagatcac cgccaacagc agcagactcg tgcacctgaa catgcccgag    240
agcgagaact accggcgcgt cgtcgtgaac aacctggaca agaccgctgt caacggcaac    300
atggccctgg acgataccca cgcccagatt gtcacacctt ggagcctcgt ggatgccaat    360
gcctgggggg tgtggtttaa ccccggcgac tggcagctca ttgtcaacac catgagcgag    420
ctgcacctcg tctccttcga gcaggaaatc ttcaacgtcg tgctgaaaac tgtctccgag    480
agcgccacac agccccccac caaagtgtac aacaacgacc tgaccgcctc cctgatggtc    540
gccctggaca gcaacaacac catgcccttc acccctgccg ccatgcggag cgagacactg    600
ggcttctacc cctggaagcc caccatccct acccccctggc ggtactactt tcaatgggac    660
agaaccctga tccccagcca cacaggcacc agcggcaccc ctaccaacat ctaccacggc    720
accgaccccg acgacgtgca gttctacacc atcgagaaca gcgtgcccgt gcatctgctg    780
agaaccggcg acgaatttgc cacaggcaca ttctttttcg actgcaaacc ctgccggctg    840
acccacacct ggcagaccaa tagagccctg ggcctgcccc cattcctgaa ctccctgcct    900
caggccgagg gcggcaccaa ctttggctat atcggcgtgc agcaggacaa gcggagagga    960
gtcacacaga tgggcaagac caactacatc accgaggcca caatcatgcg gcctgccgaa   1020
gtcggataca gcgcccccta ctacagcttc gaggccagca cccagggccc cttcaagaca   1080
cctattgccg ccggaagagg cggagcccag accgatgaga atcagggcgc cgacggcaac   1140
cccagatacg cctttggcag acagcacggc cagaaaacca ccaccaccgg cgagacaccc   1200
gaacgcttca cctatatcgc ccaccaggac accggcagat accccgaggg cgactggatt   1260
cagaacatca acttcaacct gcctgtcacc gacgacaacg tgctgctgcc cacagatccc   1320
atcggcggca agaccggcat caactacacc aatatcttca acacctacgg ccctctgacc   1380
gccctgaaca acgtgccccc cgtgtacccc aacggacaga tctgggacaa ggaattcgac   1440
accgacctga agccccggct gcacgtcaac gccccctttcg tctgccagaa caactgccct   1500
ggccaactct tcgtcaaagt ggcccccaac ctgaccaatg aatatgaccc tgacgccagc   1560
gccaacatga gccggattgt cacctacagc gacttttggt ggaagggaaa actcgtgttc   1620
aaggccaagc tgcgggcctc tcacacctgg aaccccatcc agcaaatgag catcaacgtg   1680
gacaaccagt tcaactacgt gcccagcaac atcggcggaa tggaaattgt cttcgaacgc   1740
tcccagctgg cccccagaaa gctgtactaa gtcgac                              1776
```

<210> SEQ ID NO 38
<211> LENGTH: 1776
<212> TYPE: DNA
<213> ORGANISM: Artificial Sequence
<220> FEATURE:
<223> OTHER INFORMATION: CPV VP2 Gen0.95 ORF with BamHI and SalI
Restriction Endonuclease Sites

<400> SEQUENCE: 38

```
ggatccgccg ccaccatgtc tgatggcgcc gtgcagcctg atggcggaca gcctgctgtg     60
cggaatgaga gagccaccgg cagcggcaat ggatctggcg gaggcggcgg agggggaagt    120
ggcggagtgg gaattagcac cggcaccttc aacaaccaga ccgagttcaa gttcctggaa    180
```

```
aacggctggg tggaaatcac cgccaacagc agcagactgg tgcacctgaa catgcccgag    240
agcgagaact accggcgggt ggtcgtgaac aacctggaca agaccgccgt gaacggcaac    300
atggccctgg acgataccca cgcccagatc gtgacaccct ggtccctggt ggatgccaat    360
gcctggggcg tgtggttcaa ccccggcgac tggcagctga tcgtgaacac catgagcgag    420
ctgcacctgg tgtccttcga gcaggaaatc ttcaacgtgg tgctgaaaac cgtgtccgag    480
agcgccacac agcccccccac caaggtgtac aacaacgacc tgaccgcctc cctgatggtg    540
gctctggaca gcaacaacac catgcccttc acccctgccg ccatgcggag cgagacactg    600
ggcttctacc cctggaagcc caccatccct accccctggc ggtactactt ccagtgggac    660
agaaccctga tccccagcca cacaggcacc agcggcaccc ctaccaacat ctaccacggc    720
accgaccccg acgacgtgca gttctacacc atcgagaaca gcgtgcccgt gcatctgctg    780
agaaccggcg acgagttcgc taccggaaca ttcttcttcg actgcaaacc ctgccggctg    840
acccacacct ggcagaccaa tagagccctg ggcctgcccc ccttcctgaa ctctctgcct    900
caggctgagg gcggcaccaa cttcggctac atcggcgtgc agcaggacaa gcggagaggc    960
gtgacccaga tgggcaaaac caactacatc accgaggcca caatcatgcg gcctgccgaa   1020
gtgggctaca gcgcccccta ctacagcttc gaggccagca cccagggccc cttcaagaca   1080
cctattgccg ccggaagagg cggagcccag accgatgaga atcagggagc tgacggcaac   1140
cccagatacg cctttggcag acagcacggc cagaaaacca ccaccaccgg cgagacaccc   1200
gagcggttca cctacattgc ccaccaggac accggcagat accccgaggg cgattggatt   1260
cagaacatca acttcaacct gcccgtgacc gacgacaacg tgctgctgcc cacagatccc   1320
atcggcggca agaccggcat caactacacc aatatcttca acacctacgg ccctctgacc   1380
gccctgaaca acgtgccccc agtgtacccc aacggccaga tttgggacaa agagttcgac   1440
accgacctga agccccggct gcatgtgaac gcccctttcg tgtgccagaa caactgccct   1500
ggccagctgt ttgtgaaggt ggcccccaac ctgaccaacg agtacgaccc tgacgccagc   1560
gccaacatga gccggatcgt gacctacagc gacttctggt ggaagggcaa gctggtgttc   1620
aaggccaagc tgcgggcctc tcacacctgg aaccccatcc agcagatgag catcaacgtg   1680
gacaaccagt tcaactacgt gcccagcaac atcggcggaa tggaaatcgt gtttgagaga   1740
tcccagctgg cccccagaaa gctgtactga gtcgac                              1776
```

<210> SEQ ID NO 39
<211> LENGTH: 1776
<212> TYPE: DNA
<213> ORGANISM: Artificial Sequence
<220> FEATURE:
<223> OTHER INFORMATION: NUCLEOTIDE SEQUENCE OF TRANSFER PLASMID EHV-4 p430 CPV VP2 (Despliced) EXPRESSION CASSETTE

<400> SEQUENCE: 39

```
ggatccgccg ccaccatgtc tgatggcgcc gtgcagcctg atggcggaca gcctgccgtc     60
cggaatgaga gagccaccgg cagcggcaat ggatctggcg gaggcggcgg aggcggaagt    120
ggcggcgtcg gcattagcac cggcaccttc aacaaccaga ccgagttcaa gttcctggaa    180
aacggctggg tcgagatcac cgccaacagc agcagactcg tgcacctgaa catgcccgag    240
agcgagaact accggcgcgt cgtcgtgaac aacctggaca agaccgctgt caacggcaac    300
atggccctgg acgataccca cgcccagatt gtcacacctt ggagcctcgt ggatgccaat    360
gcctgggggg tgtggtttaa ccccggcgac tggcagctca ttgtcaacac catgagcgag    420
```

-continued

```
ctgcacctcg tctccttcga gcaggaaatc ttcaacgtcg tgctgaaaac tgtctccgag    480

agcgccacac agccccccac caaagtgtac aacaacgacc tgaccgcctc cctgatggtc    540

gccctggaca gcaacaacac catgcccttc acccctgccg ccatgcggag cgagacactg    600

ggcttctacc cctggaagcc caccatccct accccctggc ggtactactt tcaatgggac    660

agaaccctga tccccagcca cacaggcacc agcggcaccc ctaccaacat ctaccacggc    720

accgaccccg acgacgtgca gttctacacc atcgagaaca gcgtgcccgt gcatctgctg    780

agaaccggcg acgaatttgc cacaggcaca ttctttttcg actgcaaacc ctgccggctg    840

acccacacct ggcagaccaa tagagccctg ggcctgcccc cattcctgaa ctccctgcct    900

caggccgagg gcggcaccaa ctttggctat atcggcgtgc agcaggacaa gcggagagga    960

gtcacacaga tgggcaagac caactacatc accgaggcca caatcatgcg gcctgccgaa   1020

gtcggataca gcgcccccta ctacagcttc gaggccagca cccagggccc cttcaagaca   1080

cctattgccg ccggaagagg cggagcccag accgatgaga atcagggcgc cgacggcaac   1140

cccagatacg cctttggcag acagcacggc cagaaaacca ccaccaccgg cgagacaccc   1200

gaacgcttca cctatatcgc ccaccaggac accggcagat accccgaggg cgactggatt   1260

cagaacatca acttcaacct gcctgtcacc gacgacaacg tgctgctgcc cacagatccc   1320

atcggcggca agaccggcat caactacacc aatatcttca acacctacgg ccctctgacc   1380

gccctgaaca acgtgccccc cgtgtacccc aacggacaga tctgggacaa ggaattcgac   1440

accgacctga agccccggct gcacgtcaac gccccctttcg tctgccagaa caactgccct   1500

ggccaactct tcgtcaaagt ggcccccaac ctgaccaatg aatatgaccc tgacgccagc   1560

gccaacatga gccggattgt cacctacagc gacttttggt ggaagggaaa actcgtgttc   1620

aaggccaagc tgcgggcctc tcacacctgg aaccccatcc agcaaatgag catcaacgtg   1680

gacaaccagt tcaactacgt gcccagcaac atcggcggaa tggaaattgt cttcgaacgc   1740

tcccagctgg cccccagaaa gctgtactaa gtcgac                              1776


<210> SEQ ID NO 40
<211> LENGTH: 1776
<212> TYPE: DNA
<213> ORGANISM: Artificial Sequence
<220> FEATURE:
<223> OTHER INFORMATION: NUCLEOTIDE SEQUENCE OF TRANSFER PLASMID EHV-4
      p430 CPV VP2 (Gen 0.95) EXPRESSION CASSETTE

<400> SEQUENCE: 40

ggatccgccg ccaccatgtc tgatggcgcc gtgcagcctg atggcggaca gcctgctgtg     60

cggaatgaga gagccaccgg cagcggcaat ggatctggcg gaggcggcgg agggggaagt    120

ggcggagtgg gaattagcac cggcaccttc aacaaccaga ccgagttcaa gttcctggaa    180

aacggctggg tggaaatcac cgccaacagc agcagactgg tgcacctgaa catgcccgag    240

agcgagaact accggcgggt ggtcgtgaac aacctggaca agaccgccgt gaacggcaac    300

atggccctgg acgataccca cgcccagatc gtgacaccct ggtccctggt ggatgccaat    360

gcctggggcg tgtggttcaa ccccggcgac tggcagctga tcgtgaacac catgagcgag    420

ctgcacctgg tgtccttcga gcaggaaatc ttcaacgtgg tgctgaaaac cgtgtccgag    480

agcgccacac agccccccac caaggtgtac aacaacgacc tgaccgcctc cctgatggtg    540

gctctggaca gcaacaacac catgcccttc acccctgccg ccatgcggag cgagacactg    600

ggcttctacc cctggaagcc caccatccct accccctggc ggtactactt ccagtgggac    660
```

agaaccctga tccccagcca cacaggcacc agcggcaccc ctaccaacat ctaccacggc 720
accgaccccg acgacgtgca gttctacacc atcgagaaca gcgtgcccgt gcatctgctg 780
agaaccggcg acgagttcgc taccggaaca ttcttcttcg actgcaaacc ctgccggctg 840
acccacacct ggcagaccaa tagagccctg ggcctgcccc ccttcctgaa ctctctgcct 900
caggctgagg gcggcaccaa cttcggctac atcggcgtgc agcaggacaa gcggagaggc 960
gtgacccaga tgggcaaaac caactacatc accgaggcca caatcatgcg gcctgccgaa 1020
gtgggctaca gcgcccccta ctacagcttc gaggccagca cccagggccc cttcaagaca 1080
cctattgccg ccggaagagg cggagcccag accgatgaga atcagggagc tgacggcaac 1140
cccagatacg cctttggcag acagcacggc cagaaaacca ccaccaccgg cgagacaccc 1200
gagcggttca cctacattgc ccaccaggac accggcagat accccgaggg cgattggatt 1260
cagaacatca acttcaacct gcccgtgacc gacgacaacg tgctgctgcc cacagatccc 1320
atcggcggca agaccggcat caactacacc aatatcttca acacctacgg ccctctgacc 1380
gccctgaaca acgtgccccc agtgtacccc aacggccaga tttgggacaa agagttcgac 1440
accgacctga agccccggct gcatgtgaac gccccctttcg tgtgccagaa caactgccct 1500
ggccagctgt ttgtgaaggt ggcccccaac ctgaccaacg agtacgaccc tgacgccagc 1560
gccaacatga gccggatcgt gacctacagc gacttctggt ggaagggcaa gctggtgttc 1620
aaggccaagc tgcgggcctc tcacacctgg aaccccatcc agcagatgag catcaacgtg 1680
gacaaccagt tcaactacgt gcccagcaac atcggcggaa tggaaatcgt gtttgagaga 1740
tcccagctgg cccccagaaa gctgtactga gtcgac 1776

<210> SEQ ID NO 41
<211> LENGTH: 2502
<212> TYPE: DNA
<213> ORGANISM: Artificial Sequence
<220> FEATURE:
<223> OTHER INFORMATION: NUCLEOTIDE SEQUENCE OF TRANSFER PLASMID EHV-4 pp455 CPV VP2 (Gen0.95) EXPRESSION CASSETTE

<400> SEQUENCE: 41
actggtggta gcatatacta ccttatttat acgctccgag ctgtttttca gcatgctagc 60
acccaacgcc gagcgagagt atataactcc catcattgcc cacaagctta tgccacttat 120
tagcgtccgc tctgccgttt gcttagtcat aatatctacc gccgtttacg cagcagacgc 180
tatctgcgac acaattggat ttgcgatacc gcgcatgtgg atgtgtattt taatgagatc 240
aacctccatg aagcgtaact aggggggcctc ccactgaggc actaccggct tagcagctga 300
ctaacacagt ataaaacgtg agaagaaatc agtctcatgc gccattagcg ctaggctagt 360
tagcgtggag gaccggagcg ctaccgccag cagtttcatc cgcctggtta cgggtttgtt 420
aacacctacc ggtgttttac cgctaccata ggatcggatc cgccgccacc atgtctgatg 480
gcgccgtgca gcctgatggc ggacagcctg ctgtgcggaa tgagagagcc accggcagcg 540
gcaatggatc tggcggaggc ggcggagggg gaagtggcgg agtgggaatt agcaccggca 600
ccttcaacaa ccagaccgag ttcaagttcc tggaaaacgg ctgggtggaa atcaccgcca 660
acagcagcag actggtgcac ctgaacatgc ccgagagcga gaactaccgg cgggtggtcg 720
tgaacaacct ggacaagacc gccgtgaacg gcaacatggc cctggacgat acccacgccc 780
agatcgtgac accctggtcc ctggtggatg ccaatgcctg ggcgtgtgg ttcaaccccg 840 gcgactggca gctgatcgtg aacaccatga gcgagctgca cctggtgtcc ttcgagcagg 900
aaatcttcaa cgtggtgctg aaaaccgtgt ccgagagcgc cacacagccc cccaccaagg 960
tgtacaacaa cgacctgacc gcctccctga tggtggctct ggacagcaac aacaccatgc 1020
ccttcacccc tgccgccatg cggagcgaga cactgggctt ctacccctgg aagcccacca 1080
tccctacccc ctggcggtac tacttccagt gggacagaac cctgatcccc agccacacag 1140
gcaccagcgg cacccctacc aacatctacc acggcaccga ccccgacgac gtgcagttct 1200
acaccatcga gaacagcgtg cccgtgcatc tgctgagaac cggcgacgag ttcgctaccg 1260
gaacattctt cttcgactgc aaaccctgcc ggctgaccca cacctggcag accaatagag 1320
ccctgggcct gcccccccttc ctgaactctc tgcctcaggc tgagggcggc accaacttcg 1380
gctacatcgg cgtgcagcag gacaagcgga gaggcgtgac ccagatgggc aaaaccaact 1440
acatcaccga ggccacaatc atgcggcctg ccgaagtggg ctacagcgcc ccctactaca 1500
gcttcgaggc cagcacccag ggccccttca agacacctat tgccgccgga agaggcggag 1560
cccagaccga tgagaatcag ggagctgacg gcaaccccag atacgccttt ggcagacagc 1620
acggccagaa aaccaccacc accggcgaga cacccgagcg gttcacctac attgcccacc 1680
aggacaccgg cagatacccc gagggcgatt ggattcagaa catcaacttc aacctgcccg 1740
tgaccgacga caacgtgctg ctgcccacag atcccatcgg cggcaagacc ggcatcaact 1800
acaccaatat cttcaacacc tacggccctc tgaccgccct gaacaacgtg cccccagtgt 1860
accccaacgg ccagatttgg gacaaagagt tcgacaccga cctgaagccc cggctgcatg 1920
tgaacgcccc tttcgtgtgc cagaacaact gccctggcca gctgtttgtg aaggtggccc 1980
ccaacctgac caacgagtac gaccctgacg ccagcgccaa catgagccgg atcgtgacct 2040
acagcgactt ctggtggaag ggcaagctgg tgttcaaggc caagctgcgg gcctctcaca 2100
cctggaaccc catccagcag atgagcatca acgtggacaa ccagttcaac tacgtgccca 2160
gcaacatcgg cggaatggaa atcgtgtttg agagatccca gctggccccc agaaagctgt 2220
actgagtcga ctatttcgag tacctctagg gccgcttcga gcagacatga taagatacat 2280
tgatgagttt ggacaaacca caactagaat gcagtgaaaa aaatgcttta tttgtgaaat 2340
ttgtgatgct attgctttat ttgtaaccat tataagctgc aataaacaag ttaacaacaa 2400
caattgcatt cattttatgt ttcaggttca gggggagatg tgggaggttt tttaaagcaa 2460
gtaaaacctc tacaaatgtg gtaaaatcga atctagatcc tc 2502

<210> SEQ ID NO 42
<211> LENGTH: 2304
<212> TYPE: DNA
<213> ORGANISM: Artificial Sequence
<220> FEATURE:
<223> OTHER INFORMATION: NUCLEOTIDE SEQUENCE OF TRANSFER PLASMID EHV-4 p430 RabG (n) EXPRESSION CASSETTE

<400> SEQUENCE: 42
ctctatttga ggacccgccg agtaccccac aagagtatgt aaaaagctgt cattctcaac 60
tactgagaat aatatcaaag ctaaagataa accctgagga gtttccacgg gaaccagagt 120
ctaggctcgt gcgcggatac atcgaatacg ccagcctaga gcgtaagcca catacgcgct 180
atccttgctt ccagcgcgtg aacctacaca ttgacgggga atttttgatc cataaaatgc 240
tagcgttcaa tgctgcgatg cgcccatccg cagaagagtt gttgtcctac ccaatgttta 300
tgaatctgta ggatgactaa cagatttggg gtggagacgg cgtgggcgat actgtataaa 360
gttgtactac ttaccagccc agtcagtgtg ctgtagtgcc accacctgta aagctgtgat 420

```
aagctgcagt tggatccgcc gccaccatgg taccggttcc tcaggctctc ctgtttgtac    480

cccttctggt tttccattg tgttttggga aattccctat ttacacgata ccagacaagc    540

ttggtccctg gagcccgatt gacatacatc acctcagctg cccaaacaat ttggtagtgg    600

aggacgaagg atgcaccaac ctgtcagggt tctcctacat ggaacttaaa gttggataca    660

tctcagccat aaaaatgaac gggttcactt gcacaggcgt tgtgacggag gctgaaacct    720

acactaactt cgttggttat gtcacaacca cgttcaaaag aaagcatttc cgcccaacac    780

cagatgcatg tagagccgcg tacaactgga agatggccgg tgaccccaga tatgaagagt    840

ctctacacaa tccgtaccct gactaccact ggcttcgaac tgtaaaaacc accaaggagt    900

ctctcgttat catatctcca agtgtggcag atttggaccc atatgacaga tcccttcact    960

cgagggtctt ccctggcggg aagtgctcag gagtagcggt gtcttctacc tactgctcca   1020

ctaaccacga ttacaccatt tggatgcccg agaatccgag actagggatg tcttgtgaca   1080

tttttaccaa tagtagaggg aagagagcat ccaaagggag tgagacttgc ggctttgtag   1140

atgaaagagg cctatataag tctttaaaag gagcatgcaa actcaagtta tgtggagttc   1200

tcggacttag acttatggat ggaacatggg tctcgatgca aacatcaaat gaaaccaaat   1260

ggtgccctcc cggtcagttg atcaatttgc acgactttcg ctcagacgaa attgagcacc   1320

ttgttgtaga ggagttggtc aagaagagag aggagtgtct ggatgcacta gagtccatca   1380

tgaccaccaa gtcagtaagt ttcagacgtc tcagtcattt aagaaaactt gtccctgggt   1440

ttggaaaagc atataccata ttcaacaaga ccttgatgga agccgatgct cactacaagt   1500

cagtcagaac ttggaatgag atcatccctt caaaagggtg tttaagagtt ggggggaggt   1560

gtcatcctca tgtaaacggg gtatttttca atggtataat attaggacct gacggcaatg   1620

tcttaatccc agagatgcaa tcatccctcc tccagcaaca tatggagttg ttggtatcct   1680

cggttatccc ccttatgcac cccctggcag acccgtctac cgttttcaag aacggtgacg   1740

aggctgagga ttttgttgaa gttcaccttc ccgatgtgca cgaacggatc tcaggagttg   1800

acttgggtct cccgaactgg gggaagtatg tattactgag tgcaggggcc ctgactgcct   1860

tgatgttgat aattttcctg atgacatgct ggagaagagt caatcgatcg gaacctacac   1920

aacacaatct cagagggaca gggagggagg tgtcagtcac tccccaaagc gggaagatca   1980

tatcttcatg ggaatcatac aagagcgggg gtgagaccgg actgtgagtc gactatttcg   2040

agtacctcta gggccgcttc gagcagacat gataagatac attgatgagt ttggacaaac   2100

cacaactaga atgcagtgaa aaaaatgctt tatttgtgaa atttgtgatg ctattgcttt   2160

atttgtaacc attataagct gcaataaaca agttaacaac aacaattgca ttcattttat   2220

gtttcaggtt cagggggaga tgtgggaggt tttttaaagc aagtaaaacc tctacaaatg   2280

tggtaaaatc gaatctagat cctc                                          2304
```

<210> SEQ ID NO 43
<211> LENGTH: 2328
<212> TYPE: DNA
<213> ORGANISM: Artificial Sequence
<220> FEATURE:
<223> OTHER INFORMATION: NUCLEOTIDE SEQUENCE OF TRANSFER PLASMID EHV-4
p455 RabG (n) EXPRESSION CASSETTE

<400> SEQUENCE: 43

```
actggtggta gcatatacta ccttatttat acgctccgag ctgtttttca gcatgctagc     60

acccaacgcc gagcgagagt atataactcc catcattgcc cacaagctta tgccacttat    120
```

tagcgtccgc tctgccgttt gcttagtcat aatatctacc gccgtttacg cagcagacgc 180
tatctgcgac acaattggat ttgcgatacc gcgcatgtgg atgtgtattt taatgagatc 240
aacctccatg aagcgtaact agggggcctc ccactgaggc actaccggct tagcagctga 300
ctaacacagt ataaaacgtg agaagaaatc agtctcatgc gccattagcg ctaggctagt 360
tagcgtggag gaccggagcg ctaccgccag cagtttcatc cgcctggtta cgggtttgtt 420
aacacctacc ggtgttttac cgctaccata ggatcggatc cgccgccacc atggtaccgg 480
ttcctcaggc tctcctgttt gtacccettc tggtttttcc attgtgtttt gggaaattcc 540
ctatttacac gataccagac aagcttggtc cctggagccc gattgacata catcacctca 600
gctgcccaaa caatttggta gtggaggacg aaggatgcac caacctgtca gggttctcct 660
acatggaact taaagttgga tacatctcag ccataaaaat gaacgggttc acttgcacag 720
gcgttgtgac ggaggctgaa acctacacta acttcgttgg ttatgtcaca accacgttca 780
aaagaaagca tttccgccca acaccagatg catgtagagc cgcgtacaac tggaagatgg 840
ccggtgaccc cagatatgaa gagtctctac acaatccgta ccctgactac cactggcttc 900
gaactgtaaa aaccaccaag gagtctctcg ttatcatatc tccaagtgtg gcagatttgg 960
acccatatga cagatccctt cactcgaggg tcttccctgg cgggaagtgc tcaggagtag 1020
cggtgtcttc tacctactgc tccactaacc acgattacac catttggatg cccgagaatc 1080
cgagactagg gatgtcttgt gacattttta ccaatagtag agggaagaga gcatccaaag 1140
ggagtgagac ttgcggcttt gtagatgaaa gaggcctata taagtcttta aaaggagcat 1200
gcaaactcaa gttatgtgga gttctcggac ttagacttat ggatggaaca tgggtctcga 1260
tgcaaacatc aaatgaaacc aaatggtgcc ctcccggtca gttgatcaat ttgcacgact 1320
ttcgctcaga cgaaattgag caccttgttg tagaggagtt ggtcaagaag agagaggagt 1380
gtctggatgc actagagtcc atcatgacca ccaagtcagt aagtttcaga cgtctcagtc 1440
atttaagaaa acttgtccct gggtttggaa aagcatatac catattcaac aagaccttga 1500
tggaagccga tgctcactac aagtcagtca gaacttggaa tgagatcatc ccttcaaaag 1560
ggtgtttaag agttgggggg aggtgtcatc ctcatgtaaa cggggtattt ttcaatggta 1620
taatattagg acctgacggc aatgtcttaa tcccagagat gcaatcatcc ctcctccagc 1680
aacatatgga gttgttggta tcctcggtta tccccttat gcacccccctg gcagacccgt 1740 ctaccgtttt caagaacggt gacgaggctg aggattttgt tgaagttcac cttcccgatg 1800
tgcacgaacg gatctcagga gttgacttgg gtctcccgaa ctgggggaag tatgtattac 1860
tgagtgcagg ggccctgact gccttgatgt tgataatttt cctgatgaca tgctggagaa 1920
gagtcaatcg atcggaacct acacaacaca atctcagagg gacagggagg gaggtgtcag 1980
tcactcccca aagcgggaag atcatatctt catgggaatc atacaagagc gggggtgaga 2040
ccggactgtg agtcgactat ttcgagtacc tctagggccg cttcgagcag acatgataag 2100
atacattgat gagtttggac aaaccacaac tagaatgcag tgaaaaaaat gctttatttg 2160
tgaaatttgt gatgctattg ctttatttgt aaccattata agctgcaata aacaagttaa 2220
caacaacaat tgcattcatt ttatgtttca ggttcagggg gagatgtggg aggtttttta 2280
aagcaagtaa aacctctaca aatgtggtaa aatcgaatct agatcctc 2328

<210> SEQ ID NO 44
<211> LENGTH: 24
<212> TYPE: DNA

-continued

```
<213> ORGANISM: Artificial Sequence
<220> FEATURE:
<223> OTHER INFORMATION: PRIMER

<400> SEQUENCE: 44

ctggttttac aacccagcac ttgc                                    24


<210> SEQ ID NO 45
<211> LENGTH: 22
<212> TYPE: DNA
<213> ORGANISM: Artificial Sequence
<220> FEATURE:
<223> OTHER INFORMATION: PRIMER

<400> SEQUENCE: 45

gactcctctc cgcttgtcct gc                                      22


<210> SEQ ID NO 46
<211> LENGTH: 24
<212> TYPE: DNA
<213> ORGANISM: Artificial Sequence
<220> FEATURE:
<223> OTHER INFORMATION: PRIMER

<400> SEQUENCE: 46

ctggttttac aacccagcac ttgc                                    24


<210> SEQ ID NO 47
<211> LENGTH: 22
<212> TYPE: DNA
<213> ORGANISM: Artificial Sequence
<220> FEATURE:
<223> OTHER INFORMATION: PRIMER

<400> SEQUENCE: 47

cgatgtagcc gaagttggtg cc                                      22
```